US009662298B2

(12) United States Patent
Tamarkin et al.

(10) Patent No.: US 9,662,298 B2
(45) Date of Patent: May 30, 2017

(54) WAX FOAMABLE VEHICLE AND PHARMACEUTICAL COMPOSITIONS THEREOF

(71) Applicant: Foamix Pharmaceuticals Ltd., Rehovot (IL)

(72) Inventors: Dov Tamarkin, Macabim (IL); Rita Keynan, Rehovot (IL); David Schuz, Gimzu (IL); Tal Berman, Rishon Le Ziyyon (IL)

(73) Assignee: FOAMIX PHARMACEUTICALS LTD., Rehovot (IL)

( * ) Notice: Subject to any disclaimer, the term of this patent is extended or adjusted under 35 U.S.C. 154(b) by 0 days.

(21) Appl. No.: 14/161,134

(22) Filed: Jan. 22, 2014

(65) Prior Publication Data

US 2014/0271494 A1   Sep. 18, 2014

Related U.S. Application Data

(63) Continuation of application No. 12/187,840, filed on Aug. 7, 2008, now Pat. No. 8,636,982.

(51) Int. Cl.

| | | |
|---|---|---|
| *A61K 9/12* | (2006.01) | |
| *A61K 8/04* | (2006.01) | |
| *A61Q 5/00* | (2006.01) | |
| *A61Q 7/00* | (2006.01) | |
| *A61Q 19/02* | (2006.01) | |
| *A61Q 19/08* | (2006.01) | |
| *A61K 47/10* | (2017.01) | |
| *A61K 47/14* | (2017.01) | |
| *A61K 47/26* | (2006.01) | |
| *A61K 47/32* | (2006.01) | |
| *A61K 47/34* | (2017.01) | |
| *A61K 47/36* | (2006.01) | |
| *A61K 47/38* | (2006.01) | |
| *A61K 47/44* | (2017.01) | |
| *A61K 8/31* | (2006.01) | |
| *A61K 8/34* | (2006.01) | |
| *A61K 8/36* | (2006.01) | |
| *A61K 8/49* | (2006.01) | |
| *A61Q 19/00* | (2006.01) | |
| *A61K 8/86* | (2006.01) | |
| *A61K 9/00* | (2006.01) | |
| *A61K 9/107* | (2006.01) | |

(52) U.S. Cl.
CPC .............. *A61K 9/124* (2013.01); *A61K 8/046* (2013.01); *A61K 8/31* (2013.01); *A61K 8/342* (2013.01); *A61K 8/361* (2013.01); *A61K 8/4993* (2013.01); *A61K 8/86* (2013.01); *A61K 9/122* (2013.01); *A61K 47/10* (2013.01); *A61K 47/14* (2013.01); *A61K 47/26* (2013.01); *A61K 47/32* (2013.01); *A61K 47/34* (2013.01); *A61K 47/36* (2013.01); *A61K 47/38* (2013.01); *A61K 47/44* (2013.01); *A61Q 5/006* (2013.01); *A61Q 7/00* (2013.01); *A61Q 19/00* (2013.01); *A61Q 19/02* (2013.01); *A61Q 19/08* (2013.01); *A61K 9/0031* (2013.01); *A61K 9/0034* (2013.01); *A61K 9/0043* (2013.01); *A61K 9/0046* (2013.01); *A61K 9/1075* (2013.01)

(58) Field of Classification Search
CPC ........ A61K 47/44; A61K 9/1075; A61K 9/122
USPC .................................... 424/400, 45, 401, 47
See application file for complete search history.

(56) References Cited

U.S. PATENT DOCUMENTS

| | | | |
|---|---|---|---|
| 1,159,250 | A | 11/1915 | Moulton |
| 1,666,684 | A | 4/1928 | Carstens |
| 1,924,972 | A | 8/1933 | Beckert |
| 2,085,733 | A | 7/1937 | Bird |
| 2,390,921 | A | 12/1945 | Clark |
| 2,524,590 | A | 10/1950 | Boe |
| 2,586,287 | A | 2/1952 | Apperson |
| 2,617,754 | A | 11/1952 | Neely |
| 2,767,712 | A | 10/1956 | Waterman |
| 2,968,628 | A | 1/1961 | Reed |
| 3,004,894 | A | 10/1961 | Johnson et al. |
| 3,062,715 | A | 11/1962 | Reese et al. |
| 3,067,784 | A | 12/1962 | Gorman |
| 3,092,255 | A | 6/1963 | Hohman |
| 3,092,555 | A | 6/1963 | Horn |

(Continued)

FOREIGN PATENT DOCUMENTS

| | | |
|---|---|---|
| AU | 198780257 | 9/1986 |
| AU | 782515 | 12/2005 |

(Continued)

OTHER PUBLICATIONS orthomoleculare (Omegal-9 Fatty Acids (Oleic Acid) http://orthomolecular.org/nutrients/omega9.html Dec. 25, 2004).*
Everything but the Olive, (the Olive Oil Source 1998-2016). http://www.oliveoilsource.com/page/\ chemical-characteristics).*
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 8, 2010, Tamarkin.
U.S. Appl. No. 61/363,577, filed Jul. 12, 2010, Eini.

(Continued)

*Primary Examiner* — Anna Falkowitz
(74) *Attorney, Agent, or Firm* — Finnegan, Henderson, Farabow, Garrett & Dunner, L.L.P.

(57) ABSTRACT

Unique foamable vehicles or carriers comprising at least one wax, waxy substance, counterpart or derivative, a stabilizer, water, and a propellant are provided. In some embodiments, the wax is a liquid wax. In some embodiments, the wax includes a solid wax and a liquid wax. The compositions are substantially free of crystals. The components are selected to provide a composition that is substantially resistant to aging and to phase separation, and/or can substantially solubilize and or stabilize active ingredients. Pharmaceutical and cosmetic compositions with potentially enhanced skin delivery and their uses are also provided.

31 Claims, No Drawings

(56) References Cited

U.S. PATENT DOCUMENTS

| | | |
|---|---|---|
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,334,147 A | 8/1967 | Brunelle et al. |
| 3,342,845 A | 9/1967 | Sayigh et al. |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,383,280 A | 5/1968 | Kuehns |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,824,303 A | 7/1974 | Lanzet et al. |
| 3,841,525 A | 10/1974 | Siegel |
| 3,849,569 A | 11/1974 | Mead |
| 3,849,580 A | 11/1974 | Weinstein et al. |
| 3,865,275 A | 2/1975 | De Nunzio |
| 3,866,800 A | 2/1975 | Schmitt |
| 3,878,118 A | 4/1975 | Watson |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,912,667 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,953,591 A | 4/1976 | Snyder |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Shoemaker et al. |
| 4,019,657 A | 4/1977 | Spitzer et al. |
| 4,052,513 A | 10/1977 | Kaplan |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,278,206 A | 7/1981 | Prussin |
| 4,292,250 A | 9/1981 | DeLuca et al. |
| 4,292,326 A | 9/1981 | Nazzaro-Porro |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,338,211 A | 7/1982 | Stiros |
| 4,352,808 A | 10/1982 | Rane et al. |
| 4,363,806 A | 12/1982 | Bergström et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,607,101 A | 8/1986 | Bernstein |
| 4,612,193 A | 9/1986 | Gordon et al. |
| 4,627,973 A | 12/1986 | Moran et al. |
| 4,628,063 A | 12/1986 | Haines et al. |
| 4,661,340 A | 4/1987 | Nagy née Kricsfalussy et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |

(56) References Cited

U.S. PATENT DOCUMENTS

| | | |
|---|---|---|
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,851,154 A | 7/1989 | Grollier et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,876,083 A | 11/1989 | Knudson et al. |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,950,420 A | 8/1990 | Svarz |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,090 A | 4/1993 | Han |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,530 A | 6/1993 | Janchitraponvej et al. |
| 5,221,534 A | 6/1993 | DesLauriers et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,305 A | 2/1995 | Repinec et al. |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,558,872 A | 9/1996 | Jones et al. |
| 5,560,859 A | 10/1996 | Hartmann et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |

(56) References Cited

U.S. PATENT DOCUMENTS

| | | |
|---|---|---|
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,705,472 A | 1/1998 | Hayes et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,753,270 A | 5/1998 | Beauchamp et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,939,376 A | 8/1999 | Durbut et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,060,041 A | 5/2000 | Candau et al. |
| 6,071,536 A | 6/2000 | Suzuki et al. |
| 6,071,541 A | 6/2000 | Murad |
| 6,075,056 A | 6/2000 | Quigley, Jr. et al. |
| 6,080,394 A | 6/2000 | Lin et al. |
| 6,087,310 A | 7/2000 | Henkel |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,133,327 A | 10/2000 | Kimura et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,217,887 B1 | 4/2001 | Beerse et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,241,971 B1 | 6/2001 | Fox et al. |
| 6,251,369 B1 | 6/2001 | Stoltz |
| 6,258,374 B1 | 7/2001 | Friess et al. |
| 6,261,544 B1 | 7/2001 | Coury et al. |
| 6,270,781 B1 | 8/2001 | Gehlsen |
| 6,271,295 B1 | 8/2001 | Powell et al. |
| 6,274,150 B1 | 8/2001 | Simonnet et al. |
| 6,283,336 B1 | 9/2001 | Dwyer et al. |
| 6,284,802 B1 | 9/2001 | Bissett et al. |
| 6,287,546 B1 | 9/2001 | Reich et al. |
| 6,294,550 B1 | 9/2001 | Place et al. |

(56) References Cited

U.S. PATENT DOCUMENTS

| | | |
|---|---|---|
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,355,230 B2 | 3/2002 | Gers-Barlag et al. |
| 6,358,541 B1 | 3/2002 | Goodman |
| 6,358,924 B1 | 3/2002 | Hoffmann |
| 6,364,854 B1 | 4/2002 | Ferrer et al. |
| 6,372,234 B1 | 4/2002 | Deckers et al. |
| 6,375,936 B1 | 4/2002 | Allard et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,423,329 B1 | 7/2002 | Sine et al. |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,433,068 B1 | 8/2002 | Morrison et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,060 B1 | 11/2002 | Jones et al. |
| 6,479,532 B1 | 11/2002 | Kamimura et al. |
| 6,482,810 B1 | 11/2002 | Brem et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,551,604 B1 | 4/2003 | Beck et al. |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,607,716 B1 | 8/2003 | Smith et al. |
| 6,610,315 B2 | 8/2003 | Scholz et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,706,290 B1 | 3/2004 | Kajander et al. |
| 6,709,663 B2 | 3/2004 | Espinoza |
| 6,723,309 B1 | 4/2004 | Deane |
| 6,730,288 B1 | 5/2004 | Abram |
| 6,736,860 B2 | 5/2004 | Patel et al. |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,841,547 B2 | 1/2005 | Brown et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin et al. |
| 6,911,211 B2 | 6/2005 | Eini et al. |
| 6,914,057 B1 | 7/2005 | Ryan et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,986,883 B2 | 1/2006 | Pellico |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Mekata |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,842,791 B2 | 11/2010 | Britten et al. |
| 7,960,416 B2 | 6/2011 | Sato et al. |
| 8,114,385 B2 | 2/2012 | Tamarkin et al. |
| 8,119,106 B2 | 2/2012 | Tamarkin et al. |
| 8,119,109 B2 | 2/2012 | Tamarkin et al. |
| 8,158,109 B2 | 4/2012 | Abram et al. |
| 8,192,749 B2 | 6/2012 | Ashley |
| 8,211,874 B2 | 7/2012 | Theobald et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,374 B2 | 7/2013 | Tamarkin et al. |
| 8,486,375 B2 | 7/2013 | Tamarkin et al. |
| 8,486,376 B2 | 7/2013 | Friedman et al. |
| 8,512,718 B2 | 8/2013 | Eini et al. |
| 8,518,376 B2 | 8/2013 | Tamarkin et al. |

(56) References Cited

U.S. PATENT DOCUMENTS

| | | |
|---|---|---|
| 8,518,378 B2 | 8/2013 | Tamarkin et al. |
| 8,592,380 B2 | 11/2013 | Trumbore et al. |
| 8,617,100 B2 | 12/2013 | Eini et al. |
| 8,618,081 B2 | 12/2013 | Tamarkin et al. |
| 8,623,330 B2 | 1/2014 | Gurge et al. |
| 8,636,982 B2 * | 1/2014 | Tamarkin et al. ............. 424/45 |
| 8,652,443 B2 | 2/2014 | Varanasi et al. |
| 8,709,385 B2 | 4/2014 | Tamarkin et al. |
| 8,722,021 B2 | 5/2014 | Friedman et al. |
| 8,735,377 B1 | 5/2014 | Sipos |
| 8,741,265 B2 | 6/2014 | Tamarkin et al. |
| 8,784,780 B2 | 7/2014 | Gurge et al. |
| 8,795,693 B2 | 8/2014 | Tamarkin et al. |
| 8,846,039 B2 | 9/2014 | Chung et al. |
| 8,865,139 B1 | 10/2014 | Tamarkin et al. |
| 8,871,184 B2 | 10/2014 | Tamarkin et al. |
| 8,895,536 B2 | 11/2014 | Bannister et al. |
| 8,992,896 B2 | 3/2015 | Tamarkin et al. |
| 9,050,253 B2 | 6/2015 | Tamarkin et al. |
| 9,101,662 B2 | 8/2015 | Tamarkin et al. |
| 9,192,558 B2 | 11/2015 | Chen et al. |
| 9,572,775 B2 | 2/2017 | Tamarkin et al. |
| 2001/0006654 A1 | 7/2001 | Cannell et al. |
| 2001/0026790 A1 | 10/2001 | Gers-Barlag et al. |
| 2001/0027218 A1 | 10/2001 | Stern et al. |
| 2001/0027981 A1 | 10/2001 | Yquel |
| 2001/0033838 A1 | 10/2001 | Farmer |
| 2001/0036450 A1 | 11/2001 | Verite et al. |
| 2001/0054574 A1 | 12/2001 | Navarro |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0031478 A1 | 3/2002 | Keller et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Haslwanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0122811 A1 | 9/2002 | Stein et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0182234 A1 | 12/2002 | Riedel et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0013692 A1 | 1/2003 | Gullans et al. |
| 2003/0017181 A1 | 1/2003 | Rood et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0077301 A1 | 4/2003 | Maibach et al. |
| 2003/0078172 A1 | 4/2003 | Guiramand et al. |
| 2003/0082120 A1 | 5/2003 | Milstein |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0118527 A1 | 6/2003 | Jager et al. |
| 2003/0129259 A1 | 7/2003 | Mahalingam et al. |
| 2003/0130247 A1 | 7/2003 | Gans et al. |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0185861 A1 | 10/2003 | Hori et al. |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215418 A1 | 11/2003 | Asmus et al. |
| 2003/0215472 A1 | 11/2003 | Bonda et al. |
| 2003/0235597 A1 | 12/2003 | Witham et al. |
| 2004/0002550 A1 | 1/2004 | Mercurio |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 * | 10/2004 | Takase et al. ................. 424/47 |
| 2004/0197295 A1 | 10/2004 | Riedel et al. |
| 2004/0198706 A1 | 10/2004 | Carrara et al. |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 * | 12/2004 | Riedel et al. ................. 424/47 |
| 2004/0253275 A1 | 12/2004 | Eini et al. |
| 2004/0258627 A1 | 12/2004 | Riedel et al. |
| 2004/0258628 A1 | 12/2004 | Riedel et al. |
| 2004/0258643 A1 | 12/2004 | Yaqub et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |
| 2005/0031547 A1 | 2/2005 | Tamarkin et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0148552 A1 | 7/2005 | Ryan et al. |
| 2005/0153943 A1 | 7/2005 | Ashley |
| 2005/0164993 A1 | 7/2005 | Ashley |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |

(56) References Cited

U.S. PATENT DOCUMENTS

| | | |
|---|---|---|
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Mekata |
| 2006/0057168 A1 | 3/2006 | Larm et al. |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0015739 A1 | 1/2007 | Walker et al. |
| 2007/0017696 A1 | 1/2007 | Lin et al. |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0053943 A1 | 3/2007 | Wang et al. |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0111956 A1 | 5/2007 | Matsushima et al. |
| 2007/0134174 A1 | 6/2007 | Irwin et al. |
| 2007/0140998 A1 | 6/2007 | Kato et al. |
| 2007/0140999 A1 | 6/2007 | Puglia et al. |
| 2007/0141086 A1 | 6/2007 | Ohara et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0166274 A1 | 7/2007 | Mazur et al. |
| 2007/0224143 A1 | 9/2007 | Konis |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0050317 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0017147 A1 | 1/2009 | Lintner et al. |
| 2009/0041680 A1 | 2/2009 | Tamarkin et al. |
| 2009/0053290 A1 | 2/2009 | Sand et al. |
| 2009/0061001 A1 | 3/2009 | Hougaz |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0214628 A1 | 8/2009 | De Rijk |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0137198 A1 | 6/2010 | Eini et al. |
| 2010/0221194 A1 | 9/2010 | Loupenok |
| 2010/0221195 A1 | 9/2010 | Tamarkin et al. |
| 2010/0247449 A1 | 9/2010 | Graupe et al. |
| 2010/0266510 A1 | 10/2010 | Tamarkin et al. |
| 2010/0286417 A1 | 11/2010 | Mendes et al. |
| 2011/0002857 A1 | 1/2011 | Tamarkin et al. |
| 2011/0002969 A1 | 1/2011 | Serraima et al. |
| 2011/0008266 A1 | 1/2011 | Tamarkin et al. |
| 2011/0045037 A1 | 2/2011 | Tamarkin et al. |
| 2011/0097279 A1 | 4/2011 | Tamarkin et al. |
| 2011/0212033 A1 | 9/2011 | Tamarkin et al. |
| 2011/0262542 A1 | 10/2011 | Ashley |
| 2011/0268665 A1 | 11/2011 | Tamarkin et al. |
| 2011/0281827 A1 | 11/2011 | Tamarkin et al. |
| 2012/0064136 A1 | 3/2012 | Baker, Jr. et al. |
| 2012/0082632 A1 | 4/2012 | Phillips et al. |
| 2012/0087872 A1 | 4/2012 | Tamarkin et al. |
| 2012/0128598 A1 | 5/2012 | Trumbore et al. |
| 2012/0141384 A1 | 6/2012 | Tamarkin |
| 2012/0148503 A1 | 6/2012 | Tamarkin et al. |
| 2012/0156144 A1 | 6/2012 | Tamarkin et al. |
| 2012/0164087 A1 | 6/2012 | Carter |
| 2012/0181201 A1 | 7/2012 | Heggie |
| 2012/0195836 A1 | 8/2012 | Tamarkin et al. |
| 2012/0213709 A1 | 8/2012 | Tamarkin et al. |
| 2012/0213710 A1 | 8/2012 | Tamarkin et al. |

(56) References Cited

U.S. PATENT DOCUMENTS

| | | | |
|---|---|---|---|
| 2012/0237453 A1 | 9/2012 | Tamarkin et al. |
| 2013/0011342 A1 | 1/2013 | Tamarkin et al. |
| 2013/0028850 A1 | 1/2013 | Tamarkin et al. |
| 2013/0053353 A1 | 2/2013 | Tamarkin et al. |
| 2013/0064777 A1 | 3/2013 | Tamarkin et al. |
| 2013/0115173 A1 | 5/2013 | Trumbore et al. |
| 2013/0161351 A1 | 6/2013 | Eini et al. |
| 2013/0164225 A1 | 6/2013 | Tamarkin et al. |
| 2013/0183250 A1 | 7/2013 | Friedman et al. |
| 2013/0183251 A1 | 7/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0189196 A1 | 7/2013 | Tamarkin et al. |
| 2013/0195769 A1 | 8/2013 | Tamarkin et al. |
| 2013/0225536 A1 | 8/2013 | Tamarkin et al. |
| 2013/0251644 A1 | 9/2013 | Majhi et al. |
| 2013/0261565 A1 | 10/2013 | Wong et al. |
| 2013/0295022 A1 | 11/2013 | Friedman et al. |
| 2013/0296387 A1 | 11/2013 | Saad |
| 2014/0050673 A1 | 2/2014 | Tamarkin et al. |
| 2014/0066524 A1 | 3/2014 | Tamarkin et al. |
| 2014/0086848 A1 | 3/2014 | Tamarkin et al. |
| 2014/0121188 A1 | 5/2014 | Tamarkin et al. |
| 2014/0140937 A1 | 5/2014 | Gurge et al. |
| 2014/0147504 A1 | 5/2014 | Salman et al. |
| 2014/0182585 A1 | 7/2014 | Tamarkin et al. |
| 2014/0186269 A1 | 7/2014 | Tamarkin et al. |
| 2014/0186442 A1 | 7/2014 | Mansouri |
| 2014/0193502 A1 | 7/2014 | Tamarkin et al. |
| 2014/0221320 A1 | 8/2014 | Joks et al. |
| 2014/0227199 A1 | 8/2014 | Tamarkin et al. |
| 2014/0228355 A1 | 8/2014 | Kortagere et al. |
| 2014/0248219 A1 | 9/2014 | Tamarkin et al. |
| 2015/0025060 A1 | 1/2015 | Tamarkin et al. |
| 2015/0098907 A1 | 4/2015 | Tamarkin et al. |
| 2015/0118164 A1 | 4/2015 | Tamarkin et al. |
| 2015/0125496 A1 | 5/2015 | Yamamoto |
| 2015/0141381 A1 | 5/2015 | Levy et al. |
| 2015/0157586 A1 | 6/2015 | Tamarkin et al. |
| 2015/0164922 A1 | 6/2015 | Tamarkin et al. |
| 2015/0174144 A1 | 6/2015 | Bowser et al. |
| 2015/0190409 A1 | 7/2015 | Tamarkin et al. |
| 2015/0196570 A1 | 7/2015 | Tamarkin et al. |
| 2015/0209296 A1 | 7/2015 | Yamamoto |
| 2015/0374625 A1 | 12/2015 | Tamarkin et al. |
| 2016/0101051 A1 | 4/2016 | Tamarkin et al. |
| 2016/0101184 A1 | 4/2016 | Tamarkin et al. |
| 2016/0158261 A1 | 6/2016 | Friedman et al. |
| 2017/0014517 A1 | 1/2017 | Tamarkin |

FOREIGN PATENT DOCUMENTS

| | | |
|---|---|---|
| AU | 2010219295 | 9/2012 |
| CA | 2114537 | 2/1993 |
| CA | 2154438 | 1/1996 |
| CA | 2422244 | 9/2003 |
| CA | 2502986 | 8/2011 |
| CA | 2534372 | 1/2012 |
| CA | 2536482 | 7/2012 |
| CH | 639913 | 12/1983 |
| DE | 1 882 100 | 11/1963 |
| DE | 1926796 | 11/1965 |
| DE | 4140474 | 6/1993 |
| DE | 10009233 | 8/2000 |
| DE | 10138495 | 2/2003 |
| DE | 102004016710 | 10/2005 |
| DE | 2 608 226 | 9/2007 |
| EP | 52404 | 5/1982 |
| EP | 0 156 507 | 10/1985 |
| EP | 0 186 453 | 7/1986 |
| EP | 0 211 550 | 2/1987 |
| EP | 0 213 827 | 3/1987 |
| EP | 0 214 865 | 3/1987 |
| EP | 0 216 856 | 4/1987 |
| EP | 0 270 316 | 6/1988 |
| EP | 0 297 436 | 1/1989 |
| EP | 0 326 196 | 8/1989 |
| EP | 0 336 812 | 10/1989 |
| EP | 0 391 124 | 10/1990 |
| EP | 0 404 376 | 12/1990 |
| EP | 0 414 920 | 3/1991 |
| EP | 0 484 530 | 5/1992 |
| EP | 0 485 299 | 5/1992 |
| EP | 0 488 089 | 6/1992 |
| EP | 0 504 301 | 9/1992 |
| EP | 0 528 190 | 2/1993 |
| EP | 0 535 327 | 4/1993 |
| EP | 0 552 612 | 7/1993 |
| EP | 0 569 773 | 11/1993 |
| EP | 0 598 412 | 5/1994 |
| EP | 0 662 431 | 7/1995 |
| EP | 0 676 198 | 10/1995 |
| EP | 0 738 516 | 10/1996 |
| EP | 0 757 959 | 2/1997 |
| EP | 0 824 911 | 2/1998 |
| EP | 0 829 259 | 3/1998 |
| EP | 0 928 608 | 7/1999 |
| EP | 0 979 654 | 2/2000 |
| EP | 0 993 827 | 4/2000 |
| EP | 1 025 836 | 8/2000 |
| EP | 1 055 425 | 11/2000 |
| EP | 0 506 197 | 7/2001 |
| EP | 1 215 258 | 6/2002 |
| EP | 1 287 813 | 3/2003 |
| EP | 1 308 169 | 5/2003 |
| EP | 1 375 386 | 1/2004 |
| EP | 1 428 521 | 6/2004 |
| EP | 1 438 946 | 7/2004 |
| EP | 1 189 579 | 9/2004 |
| EP | 1 475 381 | 11/2004 |
| EP | 1 483 001 | 12/2004 |
| EP | 1 500 385 | 1/2005 |
| EP | 1 537 916 | 6/2005 |
| EP | 1 600 185 | 11/2005 |
| EP | 1 653 932 | 5/2006 |
| EP | 1 734 927 | 12/2006 |
| EP | 1 758 547 | 3/2007 |
| EP | 1 584 324 | 11/2007 |
| EP | 1 889 609 | 2/2008 |
| EP | 1 902 706 | 3/2008 |
| EP | 2 129 383 | 12/2009 |
| EP | 2422768 | 2/2012 |
| EP | 2494959 | 9/2012 |
| FR | 2 456 522 | 12/1980 |
| FR | 2 591 331 | 6/1987 |
| FR | 2 640 942 | 6/1990 |
| FR | 2 736 824 | 1/1997 |
| FR | 2 774 595 | 8/1999 |
| FR | 2 789 371 | 8/2000 |
| FR | 2 793 479 | 11/2000 |
| FR | 2 814 959 | 4/2002 |
| FR | 2 833 246 | 6/2003 |
| FR | 2 840 903 | 12/2003 |
| FR | 2 843 373 | 2/2004 |
| FR | 2 845 672 | 4/2004 |
| FR | 2 848 998 | 6/2004 |
| FR | 2 860 976 | 4/2005 |
| FR | 2 915 891 | 11/2008 |
| GB | 808 104 | 1/1959 |
| GB | 808 105 | 1/1959 |
| GB | 922 930 | 4/1963 |
| GB | 933 486 | 8/1963 |
| GB | 998 490 | 7/1965 |
| GB | 1 026 831 | 4/1966 |
| GB | 1 033 299 | 6/1966 |
| GB | 1 081 949 | 9/1967 |
| GB | 1 121 358 | 7/1968 |
| GB | 1 162 684 | 8/1969 |
| GB | 1 170 152 | 11/1969 |
| GB | 1 201 918 | 8/1970 |
| GB | 1 347 950 | 2/1974 |
| GB | 1 351 761 | 5/1974 |
| GB | 1 351 762 | 5/1974 |

(56) References Cited

FOREIGN PATENT DOCUMENTS

| | | |
|---|---|---|
| GB | 1 353 381 | 5/1974 |
| GB | 1 376 649 | 12/1974 |
| GB | 1 397 285 | 6/1975 |
| GB | 1 408 036 | 10/1975 |
| GB | 1 457 671 | 12/1976 |
| GB | 1 489 672 | 10/1977 |
| GB | 2 004 746 | 4/1979 |
| GB | 1 561 423 | 2/1980 |
| GB | 2 114 580 | 8/1983 |
| GB | 2 153 686 | 8/1985 |
| GB | 2 172 298 | 9/1986 |
| GB | 2 206 099 | 12/1988 |
| GB | 2 166 651 | 5/1996 |
| GB | 2 337 461 | 11/1999 |
| GB | 2 367 809 | 4/2002 |
| GB | 2 406 330 | 3/2005 |
| GB | 2 406 791 | 4/2005 |
| GB | 2 474 930 | 7/2012 |
| IL | 49491 | 9/1979 |
| IL | 152 486 | 5/2003 |
| JP | 60001113 | 4/1978 |
| JP | 55069682 | 5/1980 |
| JP | 57044429 | 3/1982 |
| JP | 56039815 | 4/1984 |
| JP | 61275395 | 12/1986 |
| JP | 62241701 | 10/1987 |
| JP | 63119420 | 5/1988 |
| JP | 1100111 | 4/1989 |
| JP | 1156906 | 6/1989 |
| JP | 2184614 | 7/1990 |
| JP | 2255890 | 10/1990 |
| JP | 4-51958 | 2/1992 |
| JP | 4282311 | 10/1992 |
| JP | 4312521 | 11/1992 |
| JP | 5070340 | 3/1993 |
| JP | 5213734 | 8/1993 |
| JP | 6100414 | 4/1994 |
| JP | H06-263630 | 6/1994 |
| JP | 6329532 | 11/1994 |
| JP | 2007/155667 | 6/1995 |
| JP | 7215835 | 8/1995 |
| JP | 2008/040899 | 2/1996 |
| JP | 8501529 | 2/1996 |
| JP | 8119831 | 5/1996 |
| JP | 8165218 | 6/1996 |
| JP | 8277209 | 10/1996 |
| JP | 09 084855 | 3/1997 |
| JP | 9099553 | 4/1997 |
| JP | 9110636 | 4/1997 |
| JP | 10114619 | 5/1998 |
| JP | 3050289 | 9/1998 |
| JP | 2010/332456 | 12/1998 |
| JP | 11501045 | 1/1999 |
| JP | 11250543 | 9/1999 |
| JP | 2000/017174 | 1/2000 |
| JP | 2000/080017 | 3/2000 |
| JP | 2000/128734 | 5/2000 |
| JP | 2000/191429 | 7/2000 |
| JP | 2000/239140 | 9/2000 |
| JP | 2000/351726 | 12/2000 |
| JP | 2000/354623 | 12/2000 |
| JP | 2001/002526 | 1/2001 |
| JP | 2001/019606 | 1/2001 |
| JP | 2001/072963 | 3/2001 |
| JP | 2002/012513 | 1/2002 |
| JP | 2002/047136 | 2/2002 |
| JP | 2002/524490 | 8/2002 |
| JP | 2002/302419 | 10/2002 |
| JP | 2003/012511 | 1/2003 |
| JP | 2003/055146 | 2/2003 |
| JP | 2004/047136 | 2/2004 |
| JP | 2004/250435 | 9/2004 |
| JP | 2004/348277 | 12/2004 |
| JP | 2005/314323 | 11/2005 |
| JP | 2005/350378 | 12/2005 |
| JP | 2006/008574 | 1/2006 |
| JP | 2006/036317 | 2/2006 |
| JP | 2006/103799 | 4/2006 |
| JP | 2006525145 | 11/2006 |
| JP | 2007/131539 | 5/2007 |
| JP | 2007326996 | 12/2007 |
| KR | 143232 | 7/1998 |
| KR | 2001/003063 | 1/2001 |
| NZ | 520014 | 5/2005 |
| NZ | 540166 | 6/2007 |
| RU | 2277501 | 6/2006 |
| UA | 66796 | 6/2004 |
| WO | 82/01821 | 6/1982 |
| WO | 86/05389 | 9/1986 |
| WO | 88/01502 | 3/1988 |
| WO | 88/01863 | 3/1988 |
| WO | 88/08316 | 11/1988 |
| WO | 89/06537 | 7/1989 |
| WO | 90/05774 | 5/1990 |
| WO | 91/11991 | 8/1991 |
| WO | 92/00077 | 1/1992 |
| WO | 92/05142 | 4/1992 |
| WO | 92/05763 | 4/1992 |
| WO | 92/11839 | 7/1992 |
| WO | WO 92/13602 | 8/1992 |
| WO | 93/25189 | 12/1993 |
| WO | 94/06440 | 3/1994 |
| WO | 96/03115 | 2/1996 |
| WO | 96/19921 | 7/1996 |
| WO | 96/24325 | 8/1996 |
| WO | 96/26711 | 9/1996 |
| WO | 96/27376 | 9/1996 |
| WO | 96/39119 | 12/1996 |
| WO | 97/03638 | 2/1997 |
| WO | 97/39745 | 10/1997 |
| WO | 98/17282 | 4/1998 |
| WO | 98/18472 | 5/1998 |
| WO | 98/19654 | 5/1998 |
| WO | 98/21955 | 5/1998 |
| WO | 98/23291 | 6/1998 |
| WO | WO 98/31339 | 7/1998 |
| WO | 98/36733 | 8/1998 |
| WO | 98/52536 | 11/1998 |
| WO | 99/08649 | 2/1999 |
| WO | 99/20250 | 4/1999 |
| WO | 99/37282 | 7/1999 |
| WO | 99/53923 | 10/1999 |
| WO | 00/09082 | 2/2000 |
| WO | 00/15193 | 3/2000 |
| WO | 00/23051 | 4/2000 |
| WO | WO 00/62776 | 4/2000 |
| WO | 00/33825 | 6/2000 |
| WO | 00/38731 | 7/2000 |
| WO | 00/61076 | 10/2000 |
| WO | 00/72805 | 12/2000 |
| WO | 00/76461 | 12/2000 |
| WO | 01/05366 | 1/2001 |
| WO | WO 01/01949 | 1/2001 |
| WO | 01/08681 | 2/2001 |
| WO | 01/10961 | 2/2001 |
| WO | 01/53198 | 7/2001 |
| WO | 01/54212 | 7/2001 |
| WO | 01/54679 | 8/2001 |
| WO | 01/62209 | 8/2001 |
| WO | 01/70242 | 9/2001 |
| WO | 01/82880 | 11/2001 |
| WO | 01/82890 | 11/2001 |
| WO | 01/85102 | 11/2001 |
| WO | 01/85128 | 11/2001 |
| WO | 01/95728 | 12/2001 |
| WO | 02/00820 | 1/2002 |
| WO | WO 02/07685 | 1/2002 |
| WO | 02/15860 | 2/2002 |
| WO | 02/15873 | 2/2002 |
| WO | WO 02/24161 | 3/2002 |
| WO | 02/28435 | 4/2002 |
| WO | 02/41847 | 5/2002 |
| WO | 02/43490 | 6/2002 |
| WO | 02/062324 | 8/2002 |

(56) References Cited

FOREIGN PATENT DOCUMENTS

| | | |
|---|---|---|
| WO | 02/078667 | 10/2002 |
| WO | 02/087519 | 11/2002 |
| WO | 03/000223 | 1/2003 |
| WO | 03/002082 | 1/2003 |
| WO | WO 03/005985 | 1/2003 |
| WO | 03/013984 | 2/2003 |
| WO | WO 03/015699 | 2/2003 |
| WO | 03/051294 | 6/2003 |
| WO | 03/053292 | 7/2003 |
| WO | 03/055445 | 7/2003 |
| WO | 03/055454 | 7/2003 |
| WO | 03/070301 | 8/2003 |
| WO | 03/071995 | 9/2003 |
| WO | 03/075851 | 9/2003 |
| WO | 03/092641 | 11/2003 |
| WO | 03/097002 | 11/2003 |
| WO | WO 03/094873 | 11/2003 |
| WO | 2004/017962 | 3/2004 |
| WO | 2004/037197 | 5/2004 |
| WO | 2004/037225 | 5/2004 |
| WO | 2004/003284 | 8/2004 |
| WO | 2004/064769 | 8/2004 |
| WO | 2004/064833 | 8/2004 |
| WO | 2004/071479 | 8/2004 |
| WO | 2004/078158 | 9/2004 |
| WO | 2004/078896 | 9/2004 |
| WO | 2004/093895 | 11/2004 |
| WO | 2004/112780 | 12/2004 |
| WO | 2005/011567 | 2/2005 |
| WO | 2005/018530 | 3/2005 |
| WO | 2005/032522 | 4/2005 |
| WO | 2005/044219 | 5/2005 |
| WO | 2005/063224 | 7/2005 |
| WO | 2005/065652 | 7/2005 |
| WO | 2005/076697 | 8/2005 |
| WO | 2005/097068 | 10/2005 |
| WO | 2005/102282 | 11/2005 |
| WO | 2005/102539 | 11/2005 |
| WO | 2005/117813 | 12/2005 |
| WO | 2006/003481 | 1/2006 |
| WO | 2006/010589 | 2/2006 |
| WO | 2006/011046 | 2/2006 |
| WO | 2006/020682 | 2/2006 |
| WO | 2006/028339 | 3/2006 |
| WO | 2006/031271 | 3/2006 |
| WO | 2006/045170 | 5/2006 |
| WO | 2006/079632 | 8/2006 |
| WO | 2006/081327 | 8/2006 |
| WO | 2006/091229 | 8/2006 |
| WO | 2006/100485 | 9/2006 |
| WO | 2006/120682 | 11/2006 |
| WO | 2006/121610 | 11/2006 |
| WO | 2006/122158 | 11/2006 |
| WO | 2006/129161 | 12/2006 |
| WO | 2006/131784 | 12/2006 |
| WO | 2007/007208 | 1/2007 |
| WO | 2007/010494 | 1/2007 |
| WO | 2007/012977 | 2/2007 |
| WO | 2007/023396 | 3/2007 |
| WO | 2007/031621 | 3/2007 |
| WO | 2007/039825 | 4/2007 |
| WO | 2007/050543 | 5/2007 |
| WO | 2007/054818 | 5/2007 |
| WO | 2007/072216 | 6/2007 |
| WO | 2007/082698 | 7/2007 |
| WO | 2007/085899 | 8/2007 |
| WO | 2007/085902 | 8/2007 |
| WO | 2007/099396 | 9/2007 |
| WO | 2007/111962 | 10/2007 |
| WO | 2008/008397 | 1/2008 |
| WO | 2008/010963 | 1/2008 |
| WO | 2008/038147 | 4/2008 |
| WO | 2008/041045 | 4/2008 |
| WO | 2008/075207 | 6/2008 |
| WO | 2008/087148 | 7/2008 |
| WO | 2008/110872 | 9/2008 |
| WO | WO 2008/104734 | 9/2008 |
| WO | 2008/152444 | 12/2008 |
| WO | 2009/007785 | 1/2009 |
| WO | 2009/069006 | 6/2009 |
| WO | 2009/072007 | 6/2009 |
| WO | 2009/087578 | 7/2009 |
| WO | 2009/090495 | 7/2009 |
| WO | 2009/090558 | 7/2009 |
| WO | 2009/098595 | 8/2009 |
| WO | WO 2011/006026 | 1/2011 |
| WO | WO 2011/026094 | 3/2011 |
| WO | 2011/039637 | 4/2011 |
| WO | 2011/039638 | 4/2011 |
| WO | WO 2011/064631 | 6/2011 |
| WO | WO 2011/106026 | 9/2011 |
| WO | 2011/138678 | 11/2011 |
| WO | WO 2013/136192 | 9/2013 |
| WO | WO 2014/134394 | 9/2014 |
| WO | WO 2014/134427 | 9/2014 |
| WO | WO 2014/151347 | 9/2014 |
| WO | WO 2014/201541 | 12/2014 |
| WO | WO 2005/009416 | 2/2015 |
| WO | WO 2015/075640 | 5/2015 |
| WO | WO 2015/114320 | 8/2015 |
| WO | WO 2015/153864 | 10/2015 |

OTHER PUBLICATIONS

U.S. Appl. No. 60/789,186, filed Apr. 4, 2006, Tamarkin.
"Burn patients need vitamin D supplements." May 5, 2010. Decision News Media, Jan. 23, 2004, http://www.nutraingredients.com/Research/Burn-patients-need-vitamin-D-supplements, Accessed: May 5, 2010.
"HLB Systems", http://pharmcal.tripod.com/ch17.htm, Accessed Sep. 17, 2010, pp. 1-3.
"Minocycline" accessed on Oct. 21, 2011 at en.wikipedia.org/wiki/Minocycline, 7 pages.
"Reaction Rate" Accessed at en.wikipedia.org/wiki/Reaction_rate on Dec. 18, 2011, 6 pages.
'Niram Chemicals' [online] Niram Chemicals, [retrieved on Jul. 17, 2012]. Retrieved from the Internet: <URL: http://www.indiamart.com/niramchemicals/chemicals.html>, 7 pages.
'Surfactant' [online]. Wikipedia, 2010, [retrieved on Oct. 24, 2010]. Retrieved from the Internet: <URL: http://en.wikipedia.org/wiki/Surfactant>, 7 pages.
Adachi, Shuji. "Storage and Oxidative Stability of O/W/ Nano-emulsions." Foods Food Ingredients. J. Jpn. vol. 209, No. 11. 2004. 1 page.
Alcohol SDA 40B.http://www.pharmco-prod.com/pages/MSDS/SDA.sub.--40B.sub.--200.pdf Accessed Dec. 9, 2008, 2 pages.
Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.
Anton, N. et al. "Water-in-Oil Nano-Emulsion Formation by the phase inversion Temperature Method: A Novel and General Concept, a New Template for Nanoencapsulation," *Proceedings of the 33rd Annual Meeting and Exposition of the Controlled Release Society,* Jul. 2006, Vienna, Austria, 2 pages.
Arct et al., "Common Cosmetic Hydrophilic Ingredients as Penetration Modifiers of Flavonoids", International Journal of Cosmetic Science, 24(6):357-366 (2002)—Abstract, 1 page.
Arisan, http://www.arisankimya.com/kozmetik.htm Accessed Dec. 10, 2008, 8 pages.
Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.
Austria, et al., "Stability of Vitamin C Derivatives in Solution and Topical Formulations", Journal of Pharmaceutical and Biomedical Analysis, 15:795-801 (1997).
Barry and Badal, "Stability of minocycline, doxycycline, and tetracycline stored in agar plates and microdilution trays," *Current Microbiology,* 1978, 1:33-36.

(56) References Cited

OTHER PUBLICATIONS

Barry, B.W. et al, Comparative bio-availability and activity of proprietary topical corticosteroid preparations: vasoconstrictor assays on thirty-one ointments, British Journal of Dermatology, 93, 563-571, 1975.

Benet, et al., Application of NMR for the Determination of HLB Values of Nonionic Surfactants, Journal of the American Oil Chemists Society, vol. 49, 1972, 499-500.

Bernstein, et al., Effects of the Immunomodulating Agent R837 on Acute and Latent Herpes Simplex Virus Type 2 Invections, Antimicrobial Agents and Chemotherapy, 33(9):1511-1515 (1989).

Blute, "Phase behavior of alkyl glycerol ether surfacants", Physical Chemistry Tenside Sur. Det., 35(3):207-212 (1998).

Brenes, et al., "Stability of Copigmented Anthocyanins and Asorbics Acid in a Grape Juice Model System", J. Agric Food Chem, 53(1):49-56 (2005)—Abstrace, 1 page.

Bronopol. Revtrieved online on Jun. 4, 2011. <URL:http://chemicalland21.com/specialtychem/perchem/BRONOPOL.html>. Jul. 17, 2006. 4 pages.

Buck, et al., "Treatment of Vaginal Intraephithelial Neoplasia (Primarily Low Grade) with Imiquimod 5% Cream", Journal of Lower Genetial Tract Disease, 7(3):290-293 (2003).

Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.

Bunker, et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).

Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000)—Abstract, 1 page.

Carbowax 1000MSDS; http://www.sciencelab.com/xMSDS-Polyethylene.sub.--glycol.sub.--1000-9926- 622. Accessed Dec. 13, 2008, 6 pages.

Carelli, et al., "Effect of Vehicles on Yohimbine Permeation Across Excised Hairless Mouse Skin", Pharm Acta Helv, 73(3):127-134 (1998)—Abstract, 1 page.

Chebil, et al., "Soulbility of Flavonoids in Organic Solvents", J. Chem. Eng. Data, 52(5):1552-1556 (2007)—Abstract, 1 page.

Cheshire, et al., Disorders of Sweating, www.medscape.com, Semin Neurol 23(4):399-406, 2003.

Chevrant-Breton, et al., "Etude du Traitement Capillaire <<Bioscalin>> dans les Alopecies Diffuses de la Femme", Gazette Medicale, 93(17):75-79 (1986) [English abstract].

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

Chinnian, et al., "Photostability Profiles of Minoxidil Solutions", PDA J. Pharm Sci Technol., 50(2):94-98 (1996)—Abstract, 1 page.

Chollet, et al., "Development of a Topically Active Imiquimod Formulation", Pharmaceutical Development and Technology, 4(1):35-43 (1999).

Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.

Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.

Colloidal Silica. Retrieved online on Jun. 4, 2011. <URL:http://www.grace.com/engineeredmaterials/materialsciences/colloidalsilica/default.aspx>. Copyright 2011. 4 pages.

Croda 2. Croda Cetomacrogol 1000 Product Information Sheet. 2011 (no month given). 1 page.

Croda. Aracel 165 Product Summary. 2011 (no month given). 1 page.

D.W.A. Sharp Dictionary of Chemistry, Penguin Books, 1983, 3 pages.

Dalby, "Determination of Drug Solubility in Aerosol Propellants," Pharmaceutical Research, vol. 8, No. 9, 1991, pp. 1206-1209.

Dawber, et al., "Hypertrichosis in Females Applying Minoxidil Topical Solution and in Normal Controls", JEADV, 17:271-275 (2003).

Denatonium Benzoate http://www.newdruginfo.com/pharmaceopeia/usp28/v28230/usp28nf23s0.sub.--m- 22790.htm Accessed Dec. 9, 2008, 2 pages.

Dentinger, et al., "Stability of Nifedipine in an Extemporaneously Compounded Oral Solution", American Journal of Health-System Pharmacy, 60(10):1019-1022 (2003)—Abstract, 1 page.

disorder. (2007). In the American Heritage Dictionary of the English Language. Retrieved from http://www.credoreference.com/entry/hmdictenglang/disorder. 1 page.

Draelos, Z. D. "Antiperspirants and the Hyperhidrosis Patients." Dermatologic Therapy. 2001. vol. 14. pp. 220-224.

Edens, et al., "Storage Stability and Safey of Active Vitamin C in a New Dual-Chamber Dispenser", Journal of Applied Cosmetology, 17(4):136-143 (1999)—Abstract, 1 page.

Edirisinghe, et al., "Effect of fatty acids on endothelium-dependent relaxation in the rabbit aorta", Clin Sci (Load). Aug. 2006; 111(2): 145-51.

Edwards, "Imiquimod in Clinical Practice", J. Am Acad Dermatol., 43(1, Pt 2):S12-S17 (2000)—Abstract, 1 page.

Emulsifiers with HLB values. http://www.theherbarie.com/files/resources-center/formulating/Emulsifiers-.sub.--HLB.sub.--Values.pdf accessed Aug. 5, 2009 (3 pps).

Encyclopedia of Pharmaceutical Technology, Second Edition, vol. 3, Copyright 2002, 4 pages.

Esposito, E. et al. "Nanosystems for Skin Hydration: A Comparative Study." International Journal of Cosmetic Science. 29. 2007. pp. 39-47.

Ethanol, Accessed http://www.sigmaaldrich.com/catalog/ProductDetail.do?N4=E7023SIAL&N5=SEAR-CH.sub.--CONCAT.sub.--PNOBRAND.sub.--KEY&F=SPEC Dec. 9, 2008, 2 pages.

Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.

Farahmand, et al., "Formulation and Evaluation of a Vitamin C Multiple Emulsion", Pharmaceutical Development and Technology, 11(2):255-261 (2006)—Abstract, 1 page.

Final Office Action for U.S. Appl. No. 11/430,437, Tamarkin et al., Dec. 16, 2008, 24 pages.

Flick, Cosmetic and Toiletry Formulations, vol. 5, 2nd Edition, Copyright 1996, 63 pages. Relevant pp. 251-309.

Fontana, Anthony J., "Water Activity: Why It is Important for Food Safety," International Conference on Food Safety, Nov. 16-18, 1998, pp. 177-185.

Gallarate, et al., "On the Stability of Ascorbic Acid in Emulsified Systems for Topical and Cosmetic Use", International Journal of Pharmaceutics, 188:233-241 (1999).

Galligan, John et al., "Adhesive Polyurethane Liners for Anterior Restorations," J. Dent. Res., Jul.-Aug. 1968, pp. 629-632.

Gelbard et al. "Primary Pediatric Hyperhidrosis: A Review of Current Treatment Options." Pediatric Dermatology. 2008. 25 (6). pp. 591-598.

Gill, A.M, et al., "Adverse Drug Reactions in a Paediatric Intensive Care Unit," Acta Paediatr 84:438-441, 1995.

Gladkikh, "Ascorbic Acid and Methods of Increasing its Stability in Drugs", Translated from Khimiko-Farmatsevticheskii Zhurnal, 4(12):37-42 (1970)—1 page.

Glaser, et al., Hyperhidrosis: A Comprehensive and Practical Approach to Patient Management, Expert Rev. Dermatol. 1(6), 773-775 (2006).

Graves, S. et al. "Structure of Concentrated Nanoemulsions." The Journal of Chemical Physics. 122 America Institute of Physics. Published Apr. 1, 2005. 6 pages.

(56) References Cited

OTHER PUBLICATIONS

Groveman, et al., "Lack of Efficacy of Polysorbate 60 in the Treatment of Male Pattern Baldness", Arch Intern Med, 145:1454-1458 (1985).
Gschnait, F., et al., "Topical Indomethacin Protects from UVB and UVA Irriadiation," Arch. Dermatol. Res. 276:131-132, 1984.
Hakan, et al., "The protective effect of fish oil enema in acetic acid and ethanol induced colitis," The Turkish Journal of Gasroenterology, 2000, vol. 11, No. 2, pp. 155-161.
Hall, Karla, "Diaper Area Hemangiomas: A Unique Set of Concerns," http://members.tripod.com/.about.Michelle.sub.--G/diaper.html, Dec. 1, 2008, 8 pages.
Hallstar. Retrieved online on Jun. 4, 2011. <URL:http://www.hallstar.com/pis.php?product=1H022>. 1 page.
Hargreaves, "Chemical Formulation, An Overview of Surfactant-Based Preparations Used in Everyday Life", *The Royal Society of Chemistry*, pp. 114-115 (2003).
Harrison, et al., "Effects of cytokines and R-837, a cytokine inducer, on UV-irradiation augmented recurrent genital herpes in guinea pigs", Antivial Res., 15(4):315-322 (1991).
Harrison, et al., "Modification of Immunological Responses and Clinical Disease During Topical R-837 Treatment of Genital HSV-2 Infection", Antiviral Research, 10:209-224 (1988).
Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.
Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).
Hashim, et al. "Tinea versicolor and visceral leishmaniasis," Int J Dermatol., Apr. 1994; 33(4), pp. 258-259 (abstract only).
Heart Failure, The Merck Manual, 2008 <<http://www.merck.com/mmhe/sec03/ch025/ch025a.html>> 12 pages.
Hepburn, NC., "Cutaneous leishmaniasis," Clin Exp Dermatol, Jul. 2000; 25(5), pp. 363-370 (abstract only).
Hill, Randall M. (Ed.) Silicone Surfactants, Table of Contents and Chapter 7, "Silicone Surfactants: Applicants in the Personal Care Industry," by David T. Floyd, 1999 (30 Pages).
Hormones. Http://www.greenwillowtree.com/Page.bok?file=libido.html. Jan. 2001.
http://ibabydoc.com/online/diseaseeczema.asp., Atopic Dermatitis, Copyright 2000, 6 pages.
http://web.archive.org/web/20000106225413/http://pharmacy.wilkes.edu/kibbeweb/lab7.html, Characteristics of Surfactants and Emulsions, Jan. 29, 2010, 5 pages.
http://www.agworkshop.com/p3.asp, AG&Co. Essential oil workshop. 1 page. Accessed Jan. 31, 2010.
Hubbe, Martin. Mini-Encyclopedia of Papermaking Wet-End Chemistry: Additives and Ingredients, their Composition, Functions, Strategies for Use. Retrieved online on Jun. 4, 2011. <URL:// http://www4.ncsu.edu/~hubbe/CSIL.htm>. Feb. 1, 2001. 2 pages.
hydroxyethylcellulose. Http: //terpconnect.umd.edu/-choi/MSDS/Sigma-Aldrich/HYDROXETHYL%20CELLULOSE, 5 pages, Jan. 14, 2004.
ICI Americas Inc. "The HLB System: A Time-Saving Guide to Emulsifier Selection." Mar. 1980. pp. 1-22.
Ikuta, et al., "Scanning Electron Microscopic Observation of Oil/Wax/Water/Surfacant System", Journal of SCCJ, 34(4):280-291 (2004)—Abstract, 1 page.
Indomethacin. Retrieved online on Jun. 3, 2011. <URL:http://it03.net/com/oxymatrine/down/1249534834.pdf>. Aug. 15, 2009. 3 pages.
Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.
Izquierdo, P. et al. "Formation and Stability of Nano-Emulsions Prepared Using the Phase Inversion Temperature Method." University of Barcelona. Sep. 17, 2001. 1 page.
Jan. "Troubled Times: Detergent Foam." http://zetatalk.com/health/theal17c.htm. Accessed Feb. 9, 2012. 2 pages.
Joseph, "Understanding foams & foaming," University of Minnesota (1997), at http://www.aem.umn.edu/people/faculty/joseph/archive/docs/understandingfoams.pdf, pp. 1-8.
Kalkan, et al., The Measurement of Sweat Intensity Using a New Technique, Tr. J. of Medical Sciences 28, 515-517 (1998).
Kanamoto, et al., "Pharmacokinetics of two rectal dosage forms of ketoprofen in patients after anal surgery," J Pharmacobiodyn., Mar. 1988; 11(3):141-5.
Kang,et al., "Enhancement of the Stability and Skin Penetration of Vitamin C by Polyphenol", Immune Netw., 4(4):250-254 (2004)—Abstract, 1 page.
Karasu, T.B. et al., "Treatment of Patients with Major Depressive Disorder, Second Edition," pp. 1-78, 2000.
Kathon.TM. CG (product information sheet by Rohm and Haas, Jun. 2006).
Kim, "Stability of Minoxidil in Aqueous Solution", Yakhak Hoechi, 30(5):228-231 (1986)—Abstract, 1 page.
Kinnunen, "Skin reactions to hexylene glycol," Contact Dermatitis Sep. 1989; 21(3): 154-8.
Kleber, M.D., H.D. et al., "Treatment of Patients with Substance Use Disorders, Second Edition," pp. 1-276, 2006.
Koerber, S., "Humectants and Water Activity," Water Activity News, 2000, ISSN No. 1083-3943.
Kreuter, J. "Nanoparticles and microparticles for drug and vaccine delivery," J. Anat. (1996) 189, pp. 503-505.
Kumar, J. et ak., "Application of Broad Spectrum Antiseptic Povidone Iodine as Powerful Action: A Review," Journal of Pharmaceutical Science and Technology vol. 1(2), 2009, 48-58.
Kwak et al. "Study of Complete Transparent Nano-Emulsions which Contain Oils." IFSCC Conference 2003, Seoul, Korea, Sep. 22-24, 2003. 3 pages.
Lautenschlager, Dr. Hans. "A Closer Look on Natural Agents: Facts and Future Aspects." Kosmetic Konzept. Kosmetische Praxis. 2006 (no month given). (5), 8-10. 3 pages.
Lebwohl et al. "Treatment of Psoriasis. Part 1. Topical Therapy and Phototherapy." *J. Am. Acad. Dermatol.* 45:487-498. Oct. 2001.
Lebwohl et al., "A randomized, double-blind, placebo-controlled study of clobestasol propionate 0.05% foam in the treatment of nonscalp psoriasis," *International Journal of Dermatology*, 2002, 41(5):269-274.
Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).
Leung, et al., "Bioadhesive Drug Delivery in Water-Soluble Polymers," American Chemical Society, Chapter 23, 1991, pp. 350-366.
Li, et al., "Solubility Behavior of Imiquimod in Alkanoic Acids", Abstract 3029, Pharmaceutical Research, vol. 14, No. 11 Supplemental (November), p. S475 (1997), 2 pages.
Licking Vaginal Dryness without a Prescription. Accessed http://www.estronaut.com/a/vag.sub.--dryness.htm on Dec. 14, 2008, 3 pages.
Lippacher, A. et al. "Liquid and Semisolid SLN Dispersions for Topical Application" Rheological Characterization. European Journal of Pharmaceutics and Biopharmaceutics. 58. 2004. pp. 561-567.
Lupo, "Antioxidants and Vitamins in Cosmetics", Clinics in Dermatology, 19:467-473 (2001).
Martindale, The extra pharmacopoeia [28th] edition, Eds.: Reynolds, J.E.F. and Prasad, A.B., The Pharmaceutical Press, London, pp. 862-864, 1982.
Martindale. 33 ed. London, Bath Press, 2002. pp. 1073 and 1473.
Material Safety Data Sheet, Progesterone, Apr. 26, 2006, 5 pages.
Material Safety Data Sheet, Science Lab.com, Polyethylene Glycol 1000, MSDS, Nov. 6, 2008, 6 pages.
Merck index, 10th edition, Merck & Co., Inc.: Rahway, NJ, 1983, pp. 39 (entry 242 for allantoin).
Merck index, 14th edition, O'Neill, ed., 2006, entry for p-amino benzoic acid.

(56) References Cited

OTHER PUBLICATIONS

Merck index, 14th edition, O'Neill, ed., 2006, entry for zinc oxide.
Merck Index, an Encyclopedia of Chemicals, Drugs, and Biologicals. 13th Edition. O'Neil et al eds. Entries 1058, 2350, 6143, and 8803. 2001. 7 pages.
Merck Manual Home Edition. "Excessive Sweating: Sweating Disorders." Accessed Apr. 14, 2011 at www.merckmanuals.com/home/print/sec18/ch206/ch206c.html. 2 pages.
Merriam Webster Online Dictionary [online] retrieved from http://www.merriam-webster.com/cgi-bin/dictionary?book=dictionary&va=derivative on Jul. 5, 2008; 1 page.
Merriam-Webster Online Dictionaary, 2008, "Mousse," Merriam-Webster Online, Dec. 8, 2008 http://www.merriam-webster.com/dictionary/mousse, 2 pages.
Messenger, et al., "Minoxidil: Mechanisms of Action on Hair Growth", British Journal of Dermatology, 150:186-194 (2004).
Metronidazole. www.usp.org/pdf/EN/veterinary/metronidazole.pdf. accessed Sep. 10, 2009, 4 pages.
Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3-4):147-153 (1985)—Abstract, 1 page.
MMP Inc. International Development and Manufacturing, "Formulating specialities," http://mmpinc.com, 3 pages. Feb. 2, 2010.
Molan, Peter Clark, "World Wide Wounds," Dec. 2001, 13 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
Neutrogena. Http://www.cosmetoscope.com/2010/04/neutrogea-clinical-with-johnson-johnsons-cytomimic-techology/. Published Apr. 28, 2010. Accessed Sep. 11, 2010, 5 pages.
Nietz, "Molecular orientation at surfaces of solids," *J. Phys. Chem.*, 1928, 32(2): 255-269.
No Author Listed. "Opitmization of Nano-Emulsions Production by Microfluidization." European Food Research and Technology. vol. 225, No. 5-6. Sep. 2007. Abstract. 1 page.
Office Action for U.S. Appl. No. 11/430,437, Tamarkin et al., May 9, 2008, 27 pages.
Office Action received from the U.S. Patent Office, U.S. Appl. No. 11/430,599, Jul. 28, 2008 (59 pages).
Oil. Dictionary of Chemistry. Editor: DWA Sharp. Copyright 1990.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
OM Cinnamate. http://www.makingcosmetics.com/sunscreens/OM-Cinnamate-p102.html accessed Sep. 26, 2009, 1 page.
Padhi et al., "Phospho-olicines as positive-electrode materials for rechargeable lithium batteries," *J. Electrochemical Soc.*, 1997, 144(4): 1188-1194.
Pakpayat, et al., "Formulation of Ascorbic Acid Microemulstions with Alkyl Polyglycosides", European Journal of Pharmaceutics and Biopharmaceutics, 72:444-452 (2009).
Paula. http://ww.cosmeticscop.com/cosmetic-ingredient-dictionary/definition/259/c12-15-alkyl-benzoate.aspx. Printed Oct. 24, 2010. 1 page.
Pendergrass, "The shape and dimension of the human vagina as seen in three-dimensional vinyl polysiloxane casts," Gynecol Obstet. Invest. 1996:42(3):178-82.
Prescription Information for Aldara, Mar. 2007 (29 pages).
prevent. (2007). In the American Heritage Dictionary of the English Language. Retrieved from http://www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural Jojoba Oil Versus Dryness and Free Radicals." Cosmetics and Toiletries Manufacture Worldwide. 1988. 4 pages.

Raschke, et al., "Topical Activity of Ascorbic Acid: From In Vitro Optimization to In Vivo Efficacy", Skin Pharmacology and Physiology, 17(4):200-206 (2004)—Abstract, 1 page.
Ravet et al., "Electroactivity of natural 503-507 and synthetic triphylite," *J. of Power Sources*, 2001, 97-98: 503-507.
Raymond, Iodine as an Aerial Disinfectant, Journal of Hygiene, vol. 44, No. 5 (May 1946), pp. 359-361.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Rosacea, http://clinuvel.com/skin-conditions/common-skin-conditions/rosacea#h0-6-prevention. Accessed Sep. 9, 2010, 5 pages.
Savin, et al., "Tinea versicolor treated with terbinafine 1% solution," Int J. Dermatol, Nov. 1999; 38(11), pp. 863-865.
Schmidt A., "Malassezia furfur: a fungus belonging to the physiological skin flora and its relevance in skin disorders," Curtis., Jan. 1997; 59(1), pp. 21-4 (abstract).
Schutze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Scott as Published in Pharmaceutical Dosage Forms; Disperse Systems, vol. 3, Copyright 1998, 120 pages.
Seborrheic Dermatitis, http://www.cumc.columbia.edu/student/health/pdf/R-S/Seborrhea%20Dermatitis.pdf. Access Sep. 9, 2010, 2 pages.
Shear, et al., "Pharmacoeconomic analysis of topical treatments for tinea infections," Pharmacoeconomics. Mar. 1995; 7(3); pp. 251-267 (abstract only).
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Shrestha et al., Forming properties of monoglycerol fatty acid esters in nonpolar oil systems, *Langmuir*, 2006, 22: 8337-8345.
Sigma Aldrich, "HLB-Numbers In Lithography Nanopatterning," http://www.sigmaaldrich.com/materials-science/micro-and-nanoelectronics/1-ithography-nanopatterning/hlb-numbers.html, accessed: Feb. 2, 2009, pp. 1-3.
Sigma-Aldrich, Material Safety Data Sheet, Hydroxyethyl Cellulose, Mar. 3, 2004, 5 pages.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen OTR-2NF)," International Journal of Cosmetic Science, vol. 2(2): abstract only. Dec. 24, 2001, 1 page.
Skin Biology, CP Serum—Copper-Peptide Serum for Skin Regeneration and Reducing Wrinkles, Skin Biology, http;//web.archive.org/web/20030810230608/http://www.skinbio.com/cpserum.-html, Dec. 1, 2008, 21 pages.
Skin Deep Cosmetics. PPG-40-PEG-60 Lanolin Oil http://www.cosmeticsdatabase.com/ingredient/722972/PPG-40-PEG-60_Lanolin_Oil/?ingred06=722972. 2010, 3 pages.
Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.
Sonneville-Aubrun, O. et al. "Nanoemulsions: A New Vehicle for Skincare Products." Advances in Colloid and Interface Science. 108-109.. 2004. pp. 145-149.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment ofdandruff/seborrhoeic dermatitis," Dermatolog Treat. Jun. 2002;13(2):51-60 (abstract only).

(56) References Cited

OTHER PUBLICATIONS

Sreenivasa, et al., "Preparation and Evaluation of Minoxidil Gels for Topical Application in Alopecia", Indian Journal of Pharmaceutical Sciences, 68(4):432-436 (2006), 11 pages.
Stehle et al., Uptake of minoxidil from a new foam formulation devoid of propylene glycol to hamster ear hair follicles, *J. Invest. Dermatol.*, 2005, 124(4), A101.
Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.
Surfactant. Chemistry Glossary. Http://chemistry.about.com/od/chemistryglossary/g/surfactant.htm, 2012, 1 page.
Sweetman, Sean C. Martindale: The Complete Drug Reference. 33rd Edition. London. Pharmaceutical Press. Jun. 21, 2002. pp. 1073 and 1473. 5 pages.
Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.
Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.
Tanhehco, "Potassium Channel Modulators as Anti-Inflammatory Agents", Expert Opinion on Therapeutic Patents, 11(7):1137-1145 (2001)—Abstract, 3 pages.
Tarumoto, et al., Studies on toxicity of hydrocortisone 17-butyrate 21-propionate -1. Accute toxicity of hydrocortisone 17-butyrate 21-propionate and its analogues in mice, rats and dogs (author's trans), J Toxicol Sci., Jul. 1981; 6 Suppl: 1-16 (Abstract only).
Tata, et al., "Penetration of Minoxidil from Ethanol Propylene Glycol Solutions: Effect of Application Volume on Occlusion", Journal of Pharmaceutical Sciences, 84(6):688-691 (1995).
Tata, et al., "Relative Influence of Ethanol and Propylene Glycol Cosolvents on Deposition of Minoxidil into the Skin", Journal of Pharmaceutical Sciences, 83(10):1508-1510 (1994).
Third Party Submission for U.S. Appl. No. 12/014,088, Feb. 4, 2009, 4 pages, cited by other.
Tones-Rodriguez, JM., "New topical antifungal drugs," Arch Med Res. 1993 Winter; 24(4), pp. 371-375 (abstract).
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.
Trofatter, "imiquimod in clinical Practice", European Journal of Dermatology, 8(7 Supp.):17-19 (1998)—Abstract, 1 page.
Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.
Tsai, et al., "Effect of Minoxidil Concentration on the Deposition of Drug and Vehicle into the Skin", International Journal of Pharmaceutics, 96(1-3):111-117 (1993)—Abstract, 1 page.
Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).
Tyring, "Immune-Response Modifiers: A New Paradigm in the Treatment of Human Papillomavirus", Current Therapeutic Research, 61(9):584-596 (2000)—Abstract, 1 page.
Tzen, Jason T.C. et al. "Surface Structure and Properties of Plant Seed Oil Bodies." Department of Botany and Plant Sciences, University of California, Riverside, California 92521. Apr. 15, 1992. 9 pages.
Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.
Veron, et al., "Stability of Minoxidil Topical Formulations", Ciencia Pharmaceutica, 2(6):411-414 (1992), Abstract, 1 page.
Wermuth, C.G. "Similarity in drugs: reflections on analogue design," Drug Discovery Today, vol. 11, Nos. 7/8, Apr. 2006, pp. 348-354.
Williams, "Scale up of an olive/water cream containing 40% diethylene glycol momoethyl ether", Dev. Ind. Pharm., 26(1):71-77 (2000).
Wormser et al., Protective effect of povidone-iodine ointment against skin lesions induced by sulphur and nitrogen mustards and by non-mustard vesicants, Arch. Toxicol., 1997, 71, 165-170.
Wormser, Early topical treatment with providone-iodine ointment reduces, and sometimes prevents, skin damage following heat stimulus, Letter to the Editor, Burns 24, pp. 383, 1998.
Yamada and Chung, "Crystal Chemistry of the Olivine-Type Li($Mn_yFe_{1-y}$)$PO_4$ and ($Mn_yFe_{1-y}$)$PO_4$ as Possible 4 V Cathode Materials for Lithium Batteries," *J. Electrochemical Soc.*, 2001, 148(8): A960-967.
"Coal tars and coal-tar pitches," *Report on Carcinogens, Twelfth Edition*, 2011, 3 pages.
Adisen et al. "Topical tetracycline in the 7:953-5 treatment of acne vulgaris," *J Drugs Dermatol.*, 2008, 7:953-5.
Baskaran et al., "Poloxamer-188 improves capillary blood flow and tissue viability in a cutaneous burn wound," *J. Surg. Res.*, 2001, 101(1):56-61.
Bell-Syer et al. "A systematic review of oral treatments for fungal infections of the skin of the feet," *J. Dermatolog. Treat.*, 2001, 12:69-74.
Boehm et al. 1994, "Synthesis of high specific activity [.sup.3 H]-9-cis-retinoic acid and its application for identifying retinoids with unusual binding properties," *J. Med. Chem.*, 37:408-414.
Carapeti et al., "Topical diltiazem and bethanechol decrease anal sphincter pressure and heal anal fissures without side effects," *Dis Colon Rectum*, 2000, 43(10):1359-62.
Cook and Mortensen, "Nifedipine for treatment of anal fissures," *Dis Colon Rectum*, 2000, 43(3):430-1.
Dumortier et al., "A review of poloxamer 407 pharmaceutical and pharmacological characteristics," *Pharmaceutical Res.*, 2006, 23(12):2709-2728.
Ebadi et al., "Healing effect of topical nifedipine on skin wounds of diabetic rats," *Daru*, 2003, 11(1):19-22.
Effendy and Maibach. "Surfactants and Experimental Irritant Contact Dermatitis." *Contact Dermatol.*, 1995, 33:217-225
Elias and Ghadially, "The aged epidermal permeability barrier," *Clinical Geriatric Medicine*, Feb. 2002, pp. 103-120.
Fantin et al., "Critical influence of resistance to streptogramin B-type antibiotics on activity of RP 59500 (Quinupristin-dalfopristin) in experimental endocarditis due to *Staphylococcus aureus*," *Antimicrob Agents and Chemothery*, 1999, 39:400-405.
Fluter et al., "Glycerol accelerates recovery of barrier function in vivo," *Acta Derm. Venereol.*, 1999, 79:418-21.
Garti et al. "Sucrose Esters microemulsions," *J. Molec. Liquids*, 1999, 80:253-296.
Hammer et al. "Anti-Microbial Activity of Essential Oils and other Plant extracts," *J. Applied Microbiology*, 1999, 86:985-990
Hwang et al. "Isolation and identification of mosquito repellents in *Artemisia vulgaris*," *J. Chem. Ecol.*, 11: 1297-1306, 1985
Knight et al., "Topical diltiazem ointment in the treatment of chronic anal fissure," *Br. J. Surg.*, 2001, 88(4):553-6.
Kucharekova et al., "Effect of a lipid-rich emollient containing ceramide 3 in experimentally induced skin barrier dysfunction," *Contact Dermatitis*, Jun. 2002, pp. 331-338.
Leive et al, "Tetracyclines of various hydrophobicities as a probe for permeability of *Escherichia coli* outer membrane," *Antimicrobial Agents and Chemotherapy*, 1984, 25:539-544.
Luepke and Kemper, "The HET-CAM Test: An Alternative to the Draize Eye Test," *FD Chem. Toxic.*, 1986, 24:495-196
Osborne and Henke, "Skin Penetration Enhancers Cited in the Technical Literature," *Pharm. Technology*, Nov. 1997, pp. 58-86
Padi. "Minocycline prevents the development of neuropathic pain, but not acute pain: possible anti-inflammatory and antioxidant mechanisms," *Eur J. Pharmacol*, 2008, 601:79-87.
Palamaras and Kyriakis, "Calcium antagonists in dermatology: a review of the evidence and research-based studies," *Derm. Online Journal*, 2005, 11(2):8.

(56) References Cited

OTHER PUBLICATIONS

Passi et al., Lipophilic antioxidants in human sebum and aging, *Free Radical Research*, 2002, pp. 471-477.
Perrotti et al., "Topical Nifedipine With Lidocaine Ointment vs. Active Control for Treatment of Chronic Anal Fissure," *Dis Colon Rectum*, 2002, 45(11):1468-1475.
Repa et al. "All-trans-retinol is a ligand for the retinoic acid receptors," *Proc. Natl. Acad Sci, USA*, 90: 7293-7297, 1993.
Ruledge, "Some corrections to the record on insect repellents and attractants," *J. Am. Mosquito Control Assoc*, 1988, 4(4): 414-425.
Sakai et al., "Characterization of the physical properties of the stratum corneum by a new tactile sensor," *Skin Research and Technology*, Aug. 2000, pp. 128-134.
Schaefer, "Silicone Surfactants," *Tenside, Surfactants, Deterg.*, 1990, 27(3): 154-158.
Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.
Smith, "Hydroxy acids and skin again," *Soap Cosmetics Chemical Specialties*, 1993, pp. 54-59.
Solans et al. "Overview of basic aspects of microemulsions," Industrial Applications of Microemulsions, Solans et al Eds, New York, 1997, 66:1-17.
Squillante et al., "Codiffusion of propylene glycol and dimethyl isosorbide in hairless mouse skin," *European J. Pharm. Biopharm.*, 1998, 46(3):265-71.
Todd et al. "Volatile Silicone Fluids for Cosmetics," *91 Cosmetics and Toiletries*, 1976, 27-32.
Torma et al., "Biologic activities of retinoic acid and 3,4-dehydroretinoic acid in human keratinoacytes are similar and correlate with receptor affinities and transactivation properties," *J. Invest. Dermatology*, 1994, 102: 49-54.
USP23/NF 18 The United States Pharmacopeia: The National Formulary, US Pharmacopoeia, 1995, p. 10-14.
Van Slyke, "On the measurement of buffer values and on the relationship of buffer value to the dissociation constant of the buffer and the concentration and reaction of the buffer solution," *J. Biol. Chem.*, 1922, 52:525-570.
Van Cutsem et al., "The antiinflammatory efects of ketoconazole," *J. Am. ACAD. Dermatol.*,1991, 25(2 pt 1):257-261.
Wang and Chen, "Preparation and surface active properties of biodegradable dextrin derivative surfactants," *Colloids and Surfaces A: Physicochemical and Engineering Aspects*, 2006, 281(1-3): 190-193.
Weindl et al., "Hyaluronic acid in the treatment and prevention of skin diseases: molecular biological, pharmaceutical and clinical aspects," *Skin Pharmacology and Physiology*, 2004, 17: 207-213.
Xynos et al., "Effect of nifedipine on rectoanal motility," *Dis Colon Rectum*, 1996, 39(2):212-216.
Yamada et al., "Candesartan, an angiotensin II receptor antagonist, suppresses pancreatic inflammation and fibrosis in rats," *J. Pharmacol. Exp. Ther.*, 2003, 307(1)17-23.
Paragraph E.3.1 of regulation (EC) No 2003 (See Directive 67/548/EEC OJ 196, 16.8, 1967, p. 1.
Tzen et al., Lipids, proteins and structure of seed oil bodies from diverse species; *Plant Physiol.*, 1993, 101:267-276.
Brown et al. "Structural dependence of flavonoid interactions with Cu2+ inos: implications for their antioxidant properties," *Biochem. J.*, 1998, 330:1173-1178.
Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol*, 2003, 15:233-40.
"Mineral oil USP," Chemical Abstracts Service Registry No. 8012-95-1, 2011, 7 pages.
"Tea tree oil," Chemical Abstract No. 68647-73-4, 2012, 2 pages.
Lin et al., "Ferulic acid stabilizes a solution of vitamins c and e and doubles its photoprotection of skin," *J Invest Dermatol*, 2005, 125:826-32.

"New Nanomaterials to deliver anticancer drugs to cells developed," *Science Daily*, Jun. 2007, retrieved on Oct. 14, 2013, <URL: http://www.sciencedaily.com/releases/2007/06/070607112931.htm>, 3 pages.
"Drug Index (Professional)—Dacarbazine," *BC Cancer Agency*, Jun. 2004, retrieved on Oct. 18, 2013, <URL:http://www.bccancer.bc.ca/HPI/DrugDatabase/DrugIndexPro/Dacarbazine.htm>, 6 pages.
"Dacarbazine," *Chemical Book*, 2010, retrieved on Oct. 18, 2013, <URL: http://www.chemicalbook.com/ChemicalProductProperty_EN_CB7710656.htm>, 2 pages.
Chuna, "Minocycline versus Doxycycline in the treatment of Lyme Neuroborreliosis," *Clin. Infect. Diseases*, 2000, 30: 237-238.
"Product Data Sheet for Meclocycline," *bioaustralis fine chemicals*, Jun. 28, 2013, 1 page.
"Minocycline (DB01017)," *DrugBank*, Feb. 8, 2013, retrieved on Aug. 15, 2013, <http://www.drugbank.ca/drugs/DB01017>, 10 pages.
Google search strategy for minocycline solubility, retrieved on Aug. 15, 2013, <http://www.googl.com/search?rls=com.microsoft%3Aen-us%3AIE-SearchBox&q-melocycline+solubility>, 1 page.
"Fully refined paraffin waxes (FRP Wax)," *Industrial Raw Materials LLC*, Feb. 21, 2008, retrieved on Aug. 22, 2013, <http://irmwax.com/Wax/Paraffin/fully_refined.asp> 1 page.
Harry, "Skin Penetration," *The British Journal of Dermatology and Syphillis*, 1941, 53:65-82.
Abrams et al., "Ciclopirox gel treatment of scalp seborrheic dermatitis," *Hydroxy-Piridones as Antifungal Agents with Special Emphasis on Onychomycosis*, 1999, Chapter 8, 45-50.
Purdy et al., "Transfusion-transmitted malaria: unpreventable by current donor exclusion guidelines?" *Transfusion*, Mar. 2004, 44:464.
*Reregistration Eligibility Decision for Pyrethrins*, EPA, Jun. 7, 2006, 108 pages.
"Arquad HTL8-MS," *AkzoNobel Functional Applications*, retrieved on Mar. 18, 2013, Retrieved from the Internet: <URL: http://sc.akzonobel.com/en/fa/Pages/product-detail.aspx?prodID=8764>, 1 page.
Blaney and Cook, "Topical use of tetracycline in the treatment of acne," *Arch Dermatol*, Jul. 1976, 112:971-973.
"View of NCT01362010 on Jun. 9, 2011," ClinicalTrials.gov_, Jun. 9, 2011, retrieved on Sep. 9, 2013, <http://clinicaltrials.gov/archive/NCT01362010/2011_06_09>, 3 pages.
"View of NCT01171326 on Dec. 7, 2010," ClinicalTrials.gov_ archive, Dec. 7, 2010, retrieved on Sep. 9, 2013, <http://clinicaltrials.gov/archive/NCT01171326/2010_12_07>, 4 pages.
Durian et al., "Scaling behavior in shaving cream," *The Americal Physical Society*, Dec. 1991, 44(12):R7902-7905.
Livingstone and Hubel, "Segregation of form, color, movement, and depth: Anatomy, physiology, and perception," *Science*, May 1988, 240:740-749.
Lee et al., "Historical review of melanoma treatment and outcomes," *Clinics in Dermatology*, 2013, 31: 141-147.
Scully et al., "Cancers of the oral mucosa treatment and management," *Medscape Drugs, Diseases and Procedures*, Apr. 20, 2012, retrieved on Oct. 12, 2013, <http://emedicine.medscape.com/article/1075729-treatment>, 10 pages.
"What is TSC?," *Tuberous Sclerosis Alliance*, Jan. 1, 2005, retrieved on Feb. 6, 2014, <URL: http://www.tsalliance.org.pages.aspx?content=2>, 3 pages.
"Can tuberous sclerosis be prevented?," *Sharecare*, 2002, retrieved on Aug. 29, 2013, <URL: http://www.sharecare.com/health/autosomal-dominant-genetic-disorders/can-tuberous-sclerosis-be-prevented;jsessionid=850579B60520A907DE75930E061E60E6>, 2 pages.
Prud'homme et al., *Foams: theory, measurements and applications*, Marcel Dekker, Inc., 1996, 327-328.
Schmolka, "A review of block polymer surfactants," *Journal of the American Oil Chemists Society*, Mar. 1977, 54: 110-116.
"Shear," Vocabulary.com, retrieved on Aug. 23, 2013, <URL: https://www.vocabulary.com/dictionary/shear>, 3 pages.

(56) References Cited

OTHER PUBLICATIONS

"Sheer," Vocabulary.com, retrieved on Aug. 23, 2013, <URL: https://www.vocabulary.com/dictionary/sheer>, 3 pages.
*Sun Pharmaceutical Industried Ltd. v. Eli Lilly and Co.*, 611 F.3d 1381, 95 USPQ2d 1797 (Fed. Cir. 2010),7 pages.
*Molins PLC v. Textron Inc.*, 48 F.3d 1172, 33 USPQ2d 1823 (Fed. Cir. 1995), 19 pages.
"Crohn's Disease," *Merch Manual Home Edition*, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
"Gas Gangrene," Merch Manual Home Edition, 2008, retrieved on Jan. 16, 2013, <http://www.merckmanuals.com/home/infections/bacterial_infections/gas_gangrene.html?qt=gas gangrene&alt=sh>1 page.
"Human Immunodeficiency Virus Infection," Merch Manual Home Edition, 2008, retrieved on Jan. 16, 2013, <http://www.merckmanuals.com/home/infections/human_immunodeficiency_virus_hiv_infection/human_immunodeficiency_virus_infection.html?qt=human immunodeficiency virus infection&alt=sh>, 11 pages.
Schott, "Rheology," *Remington's Pharmaceutical Sciences*, 17th Edition, 1985, 330-345.
Cetearyl Alcohol, Natural Wellbeing, Copyright 2001-2012, retrieved on Apr. 10, 2014, http://www.naturalwellbeing.com/learning-center/Cetearyl_Alcohol, 3 pages.
Cole and Gazewood, "Diagnosis and Treatment of Impetigo," Am Fam Physician, Mar. 15, 2007, 75(6):859-864.
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neves et al., "Rheological Properties of Vaginal Hydrophilic Polymer Gels," Current Drug Delivery, 2009, 6:83-92.
Oranje et al., "Topical retapamulin ointment, 1%, versus sodium fusidate ointment, 2%, for impetigo: a randomized, observer-blinded, noninferiority study," Dermatology, 2007, 215(4):331-340.
Sciarra, "Aerosol Technology," Kirk-Othmer Encyclopedia of Chemical Technology, Jul. 2012, 20 pages.
Sehgal, "Ciclopirox: a new topical pyrodonium antimycotic agent: A double-blind study in superficial dermatomycoses," British Journal of Dermatology, 1976, 95:83-88.
Softemul-165: Product Data Sheet, Mohini Organics PVT LTD, retrieved Apr. 10, 2014, http://www.mohiniorganics.com/Softemull65.html#, 1 page.
Tayss et al., "Anionic detergent-induced skin irritation and anionic detergent-induced pH rise of bovine serum albumin," J. Soc. Cosmet. Chem., Jul./Aug. 1988, 39:267-272.
Tirmula et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.
Alcohol, Wikipedia, the free encyclopedia, retrieved on May 17, 2014, http://en.wikipedia.org/wiki/Alcohol, 17 pages.
Clobetasol Propionate Cream and Ointment, Apr. 2006, retrieved Jul. 3, 2014, http://dailymed.nlm.nih.gov/dailymed/archives/fdaDrugInfo.cfm?archiveid=994, 7 pages.
Ellis et al., "The Treatment of Psoriasis with Liquor Carbonis Detergens," J. Invest Dermatology, 1948, 10:455-459.
Gels, UNC, The Pharmaceutics and Compounding Laboratory, retrieved on Aug. 25, 2014, http://pharmlabs.unc.edu/labs/gels/agents/htm, 4 pages.
Griffin, "Calculation of HLB Values of Non-Ionic Surfactants," Journal of the Society of Cosmetic Chemists, May 14, 1954, 249-256.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Le Vine et al., "Components of the Goeckerman Regimen," Journal of Investigative Dermatology, 1979, 73:170-173.
Material Safety Data Sheet, Liquor carbonis detergens, Caelo, Nov. 28, 2013, 5 pages.
Omega-9 Fatty Acids (Oleic Acid), Orthomolecular.org, Dec. 2004, retrieved on Aug. 15, 2014, http://orthomolecular.org/nutrients/omega9.html. 1 page.
Polystyrene, Wikipedia the free encyclopedia, retrieved Apr. 21, 2014, http://web.archive.org/web/20060312210423/http://en.wikipedia.org/wiki/Polystyrene, 4 pages.
Vera et al., "Scattering optics of Foam," Applied Optics, Aug. 20, 2001, 40(24):4210-4214.
Communication of a Notice of Opposition in European Application No. 03772600.7, dated Jan. 13, 2015, 36 pages.
Cremophor a Grades, BASF The Chemical Company, Jan. 2008, 6 pages.
Luviquat Polymer Grades, BASF The Chemical Company, May 2012, 32 pages.
Material Safety Data Sheet, Mineral Oil, Macron Fine Chemicals, Oct. 24, 2011, 6 pages.
Material Safety Data Sheet, Luvitol EHO, Caelo, Nov. 28, 2013, 4 pages.
Rohstoffinformationen, Hoffmann Mineral, 2008, 8 pages (with English translation).
Ziolkowsky, "Moderne Aerosolschaume in der Kosmetik (Modern Aerosol Foams in Chemical and Marketing Aspects),", Seifen-Ole-Fette-Wachse, Aug. 1986, 112(13): 427-429 (with English translation).
Al-Mughrabi et al., "Effectiveness of Essential Oils and Their Combinations with Aluminum Starch Octenylsuccinate on Potato Storage Pathogens," TEOP, 2013, 16(1):23-31.
Beauty Banter, "Interesting list of comedogenic ingredients!!!!!!!!!!!" QVC blog, Interesting list of comedogenic ingredients, 2014, 1-14.
Chemical Characteristics, The Olive Oil Source, © 1998-2015, retrieved on Jun. 12, 2015, http://www.oliveoilsource.com/page/chemical-characteristics, 10 pages.
Codex Standard for Olive Oils and Olive Pomace Oils Codex Stan 33/1981, Adopted in 1981, recently amended 2013, 8 pages.
Devos and Miller, "Antisense Oligonucleotides: Treating neurodegeneration at the Level of RNA," Neurotherapeutics, 2013, 10:486-497.
Mailer, "Chemistry and quality of olive oil," NSW Dept. of Primary Industries, Aug. 2006, Primefact 227, 1-4.
Oh et al., "Antimicrobial activity of ethanol, glycerol monolaurate or lactic acid against Listeria moncylogenes,"Int. J. Food Microbiology, 1993, 20:239-246.
Permethrin (Insecticide), Wildpro, retrieved on Jun. 4, 2015, http://wildpro.twycrosszoo.org/S/00Chem/ChComplex/perm.htm, 5 pages.
Refina, "Viscosity Guide for Paints, Petroleum & Food Products," accessed Mar. 4, 2015, http://www.refina.co.uk/webpdfs/info_docs/Viscosity_guide_chart.pdf, 2 pages.
Thorgeirsdottir et al., "Antimicrobial activity of monocaprin: a monoglyceride with potential use as a denture disinfectant," Acta Odontologica Scandinavica, Feb. 2006, 64:21-26 (Abstract only).
United States Standards for Grades of Olive Oil and Olive-Pomace Oil, United States Dept. of Agriculture, Oct. 25, 2010, 21 pages.
WebMD, "Psoriasis Health Center," 2014, retrieved Apr. 13, 2015, http://www.webmd.com/skin-problems-and-treatments/psoriasis/psoriasis-symptoms, 3 pages.
WebMD, "Understanding Rosacea—the Basics," 2014, retrieved Apr. 13, 2015, http://www.webmd.com/skin-problems-and-treatments/understanding-rosacea-basics, 5 pages.
Williams et al., "Acne vulgaris," Lancet, 2012, 379:361-372.
Haw, "The HLB System: A Time Saving Guide to Surfactant Selection," Presentation to the Midwest Chapter of the Society of Cosmetic Chemists, Mar. 9, 2004, 39 pages.
Mead, "Electrostatic Mechanisms Underlie Neomycin Block of the Cardiac Ryanodine Receptor Channel (RyR2)," Biophysical Journal, 2004, (87): 3814-3825.
RSES (Oil in Refrigerator Systems, Service Application Manual, 2009).
Sigma-Aldrich. http://www.sigmaaldrich.com/catalog/product/sial/p1754?lang=en® ion=. Published:Mar. 5, 2014.

(56) References Cited

OTHER PUBLICATIONS

Wenninger et al., "International Cosmetic Ingredient Dictionary and Handbook," The Cosmetic, Toiletry, and Fragrance Association, Washington, DC., 1997, vol. 1, 4 pages.
Wu et al., "Interaction of Fatty Acid Monolayers with Cobalt Nanoparticles," Nano Letters, 2004, 4(2): 383-386.
Allantoin, Rompp Online, retrieved on Sep. 23, 2015, https://roempp.thieme.de/roempp4.0/do/data/RD-O 1-01552, 5 pages.
Coconut Oil, Wikipedia, the free encyclopedia, retrieved on Jul. 3, 2015, https://en.wikipedia.org/wiki/Coconut_oil, 8 pages.
Communication of a Notice of Opposition in European Application No. 03772600.7, dated Sep. 23, 2015, 42 pages.
Communication of a Notice of Opposition in European Application No. 03772600.7, dated Sep. 24, 2015, 30 pages.
Diethyltoluamid, Wikipedia, the free encyclopedia, retrieved on Sep. 11, 2015, https://de.wikipedia.org/wiki/Diethyltoluamid, 12 pages.
Dimethylphthalate, Wikipedia, the free encyclopedia, retrieved on Sep. 11, 2015, http://de.wikipedia.org/wiki/Dimethylphthalat, 8 pages.
Healy, "Gelled Emollient Systems for Controlled Fragrance Release and Enhanced Product Performance," Cosmetics and toiletries, 2002, 117(2): 47-54.
Kaur et al., "Formulation Development of Self Nanoemulsifying Drug Delivery System (SNEDDS) of Celecoxib for Improvement of Oral Bioavailability," Pharmacophore, 2013, 4(4):120-133.
Lamisil, Lamisil.http://www.fda.gov/downloads/Drugs/DrugSafety/PostmarketDrugSafetyInformationforPatientsandProviders/ucm052213.pdf, Published: Apr. 2001.
Leunapon-F, Leuna-Tenside, Screenshot, retrieved on Sep. 18, 2015, http://www.leuna-tenside.de/2006_7_14_3143/2006_8_7 5750/2006_8_7 24 l/cas-68439-49-6, 1 page.
Rowe et al., "Glyceryl Monooleate," Handbook of Pharmaceutical Excipients, 2011, pp. 1-5, retrieved on Dec. 19, 2011, http://www.medicinescomplete.com/mc/excipients/current/1001938996.htm?q=glyceryl%20monooleate&t=search&ss=text&p=1# hit.
Rowe et al., "Octyldodecanol," Handbook of Pharmaceutical Excipients, 2011, pp. 1-4, retrieved on Dec. 19, 2011, URL :http://www.medicinescomplete.com/mc/excipients/current/1001942450.htm?q=octyldodecanol&t=search&ss=text&p=1# hit.
Rowe et al., "Sucrose Palmitate," Handbook of Pharmaceutical Excipients, 2011, pp. 1-5, retrieved on Dec. 19, 2011, URL:http://www.medicinescomplete.com/mc/excipients/current/EXP-TD-c46-mn0001.htm?q=sucrose%20stearate&t=search&ss=text&p=1# hit.
Rowe et al., "Sucrose Stearate," Handbook of Pharmaceutical Excipients, 2011, pp. 1-4, retrieved on Dec. 19, 2011, URL:http://www.medicinescomplete.com/mc/excipients/current/EXP-TD-cll-mnOOO1-mnOOO1.htm?q=sucrose%20stearate&t=search&ss=text&p=3# hit.
Sanders et al., "Stabilization of Aerosol Emulsions and Foams," J. Soc. Cosmet. Chem., 1970, 21:377-391.
Security Datasheet, Luvitol EHO, Cetearyloctanoat, Nov. 27, 2013, 10 pages.
Suppositories?, CareCure, http://sci.rutgers.edu/forum/showthread.php?4176-Suppositories. Published: Apr. 16, 2002.
Triethanolamin, haute.de, retrieved on Sep. 14, 2015, http://www.haut.de/service/inci/anzeige&id=16384&query=Triethanolamine&funktio . . . , 3 pages.
Valenta, "Effects of Penetration Enhancers on the In-vitro Percutaneous Absorption of Progesterone," J. Phann. Pharrnacol., 1997, 49: 955-959.
Williams et al., "Urea analogues in propylene glycol as penetration enhancers in human skin," International Journal of Pharmaceutics, 1989, 36, 43-50.
Albrecht et al., "Topical minocycline foam for moderate to severe acne vulgaris: Phase 2 randomized double-blind, vehicle-controlled study results," J. Am. Acad. Dermatol., 2016, 74(6):1251-1252.
Chapter 1 Meaning of HLB Advantages and Limitations 1980; 4 pages.
Material Safety Data Sheet, Squalane, TCI America, 5 pages, https://www.spectrumchemical.com/MSDS/TC1-H0096.pdf. Published: Oct. 6, 2014.
Sorbitan Esters, [online] retrieved on Jul. 1, 2016 from: http://www.drugfuture.com/chemdata/sorbitan-esters.html 2 pages.
Sreenivasan et al., "Studies on Castor Oil. I. Fatty Acid Composition of Castor Oil," Journal of the American Oil Chemists Society. 1956, 33:61 -66.
Material Safety Data Sheet, Butane, Gas Innovations, Sep. 7, 2007, 3 pages.
Material Safety Data Sheet, Carbon Dioxide, Airgas, Feb. 11, 2016, 11 pages.
Material Erial Safety Data Sheet, Dimethyl Ether, Airgas, May 14, 2015, 12 pages.
Material Safety Data Sheet, N-Butane, Airgas, May 7, 2015, 13 pages.
Material Safety Data Sheet, Nitrous Oxide, Airgas, Feb. 11, 2016, 11 pages.
Material Safety Data Sheet, Propane, Airgas, Oct. 20, 2015, 12 pages.
Australian Pharmaceutical Benefits Advisory Committee (PBAC), *PBAC Public Summary Document* -Nov. 2014 Meeting (5 pages).
European Patent Application No. 03772600.7 (Patent No. 1556009): Interlocutory Decision in Opposition Proceedings, dated Feb. 3, 2017, 54 pages.
European Patent Application No. 03772600.7 (Patent No. 1556009): Minutes of Oral Proceedings, dated Feb. 3, 2017, 6 pages.
European Patent Application No. 03772600.7 (Patent No. 1556009): Reply of the Patent Proprietor to the Notices of Opposition, dated May 9, 2016, 134 pages.
European Patent Application No. 03772600.7 (Patent No. 1556009): Summons to Attend Oral Proceedings, dated Jun. 30, 2016, 19 pages.
Foamix Pharmaceuticals Statement: Use of Luviquat FC 370, Approved by Yohan Hazot, May 3, 2016, 3 pages.
Frankel, A.J. et al. (2010) "Coal Tar 2% Foam in Combination with a Superpotent Corticosteroid Foam for Plaque Psoriasis. Case Report and Clinical Implications" *J Clin Aesthet Dermatol*, 3(10):42-45.
Kircik, L.H. and S. Kumar (Aug. 2010) "Scalp Psoriasis" *J Drugs Dermatol*, 9(8 Suppl):s101-s137.
Penreco, "Intelligent Gel Technology Product Specifications," Rev. 06/16 (2 pages).
Promius™ Pharma LLC (2012) *Scytera*™ *(coal tar) Foam, 2%*. Product Information Sheet, 1 page.
Water Jel Technologies, "Material Safety Data Sheet for Neomycin Antibiotic Ointment," Dec. 1, 2004 (7 pages).
WebMD (2017) "User Reviews & Ratings—Scytera topical" [online]. Retrieved Mar. 1, 2017; retrieved from the Internet: http://www.webmd.com/drugs/drugreview-151502-Scytera+topical.aspx?drugid=151502&drugname=Scytera+topical&sortby=3 (2 pages).
Zeichner, J.A. (2010) "Use of Topical Coal Tar Foam for the Treatment of Psoriasis in Difficult-to-treat Areas" *J Clin Aesthet Dermatol*, 3(9):37-40.

* cited by examiner

WAX FOAMABLE VEHICLE AND PHARMACEUTICAL COMPOSITIONS THEREOF

This application is a continuation of and claims the benefit of priority to U.S. application Ser. No. 12/187,840 filed Aug. 7, 2008, which claims the benefit of priority under 35 U.S.C. §119(e) to U.S. Provisional Application No. 60/954,525 filed Aug. 7, 2007, entitled "Wax Foamable Vehicle And Pharmaceutical Compositions Thereof", which is incorporated in its entirety by reference.

BACKGROUND

This invention relates to foamable pharmaceutical and cosmetic compositions.

External topical administration is an important route for the administration of drugs in disease treatment. Many groups of drugs, including, for example, antibiotic, antifungal, anti-inflammatory, anesthetic, analgesic, antiallergic, corticosteroid, retinoid and anti-proliferative medications are preferably administered in hydrophobic media, namely ointment. However, ointments often form an impermeable barrier, so that metabolic products and excreta from the wounds to which they are applied are not easily removed or drained away. Furthermore, it is difficult for the active drug dissolved in the carrier to pass through the white petrolatum barrier layer into the wound tissue, so the efficacy of the drug is reduced. In addition, ointments and creams often do not create an environment for promoting respiration of the wound tissue and it is not favorable to the normal respiration of the skin. An additional disadvantage of petroleum jelly-based ointments and creams relates to the greasy feeling left following their topical application onto the skin, mucosal membranes and wounds.

Foams are considered a more convenient vehicle for topical delivery of active agents. There are several types of topical foams, including aqueous foams, such as commonly available shaving foams; hydroalcoholic foams, emulsion-based foams, comprising oil and water components, and oleaginous foams, which consist of high oil content. In skin therapy, oil containing foams are preferred, since oil contributes to skin protection and moisturization, which improve the therapeutic effect of the formulation.

Fatty acids and fatty alcohols counterparts and derivatives have been used in foamable formulations as foam adjuvants usually in low amounts of up to about 5% and may possibly have a therapeutic effect in the treatment of a variety of skin disorders and/or conditions. Some are waxy solids while others are liquid at room temperature and pressure. For example, in the case where the carbon backbone chain is 18C, stearic acid and stearyl alcohol are waxy solids whilst isostearic acid, oleic acid and oleyl alcohol are liquids. The significance of this difference in liquidity of molecules having the same or similar backbone chain on foamable compositions is investigated herein.

Jojoba oil has been used in foamable formulations usually in relatively low amounts of up to about 10% and may possibly have a therapeutic effect in the treatment of a variety of skin disorders and/or conditions.

Branched (i.e., non-straight chain) waxes like oleic acid are known to contribute to the skin penetration of an active agent.

Aldara, a commercially available topical cream containing imiquimod as active agent, uses 25% isostearic acid as a solubilizing agent.

Formulations comprising micronized imiquimod with fatty acids and fatty alcohols are known. The level of fatty acid in such formulations, however, is minimized to avoid idiosyncrasy. As such, these formulations are essentially free of isostearic acid. Moreover, such formulations are cream formulations and foam compositions of such formulations have not been specifically disclosed.

Emulsion based foam formulations comprising imiquimod and fatty acids in sufficient amount to solubilize imiquimod have been disclosed. These formulations are limited in the amount of isostearic acid that can be present in the formulation (typically 25% or less).

Aqueous foam compositions comprising partially neutralized fatty acids as organic solvents have been generally disclosed in the art. However, specific compositions containing additional components, such as polymers, surfactants, and liquid fatty acids have not been disclosed. The stability of such foams relies upon the presence of a component such as triethanolamine, as well as basic active components (such as imiquimod) to neutralize fatty acid and water foams.

Foam using very high amounts of anionic surfactants 20% to 95% with C10:0 (e.g., 1-decanol) fatty alcohol has been described in the art. The large amounts of surfactant result in a mesomorphic phase which solubilizes the propellant. The use of high levels of anionic surfactants and C10:0 fatty alcohol, which are irritants, renders these compositions unsuitable for use on the skin and eyes, and, in some cases, harmful, particularly in the eyes.

There remains an unmet need for improved, easy to use, vehicles and foam formulations, comprising wax, waxy substances, counterparts and derivatives thereof in preferably in substantial or higher concentrations which can effectively deliver and/or deposit various active agents into and onto the skin and/or other target sites and are relatively non-irritating and thus suitable for use by people having sensitive skin, body cavities and mucosal surfaces. Significantly there remains an unmet need for such vehicles and foam formulations that are substantially free from crystals. Accordingly, in some embodiments, the formulations described herein are free from crystals. In some embodiments, the formulations are free from an insoluble phase or, in some embodiments, free from insoluble matter. The presence of crystals indicates that one or more ingredients are not solubilized. In consequence amongst other things the formulation may be unstable, may be variable, may deliver unreliable amounts of active ingredients and may cause irritation and thus be unsuitable for therapeutic use. Additionally substantial crystal formation in a foamable formulation may interfere with foam release. In some embodiments, the formulations are free from crystals yet still include a suspension of solid matter or particles. In some embodiments, the solid matter or particles are not crystalline. Examples of such solid matter include, without limitation, microsponges, ground seed, metallic particles and active agents in particle form (e.g., benzyl peroxide).

There is a need for such vehicles and foam formulations in which there is a relatively low level of surfactants. Surfactants can be irritants particularly at higher levels. Repeated use of formulations with higher levels of surfactants on the skin can result in depletion of hydrophobic substances and dry skin.

High levels of surfactant can result in the formation of a mesomorphic phase. The mesomorphic phase can absorb propellant and may increase irritation, depletion of fats and dry skin. There is a need for such vehicles and foam formulations in which there is no mesomorphic phase

SUMMARY

The present invention relates to aqueous wax emulsion compositions.

In one aspect, foamable compositions are provided which include (a) a wax, (b) a stabilizer component, (c) water, and (d) a propellant. In some embodiments, the wax is a liquid wax. In other embodiments, the wax is a combination of a solid wax and a liquid wax. In some embodiments, the wax, for example the liquid wax or the solid wax, includes at least one fatty acid or at least one fatty alcohol. In some embodiments, when the liquid wax includes at least one fatty acid, the fatty acid is present in the composition at a concentration of at least about 35% by weight. In some embodiments, when the liquid wax includes at least one fatty alcohol, the fatty alcohol is present in the composition at a concentration of at least about 12% by weight. In some embodiments, when the composition includes a solid wax, the solid wax is present in the composition at a concentration of at least about 7% by weight. In one or more embodiments all the ingredients are dissolved. In further embodiments the composition is substantially free from crystals, e.g., free of an insoluble phase. Assessing whether a composition is free from crystals or free of an insoluble phase is performed by techniques known to those of skill in the art. One exemplary technique for assessing the presence of crystals or an insoluble phase in the compositions described herein is by visual inspection, e.g., using light microscopy, as described in further detail herein. In some embodiments the composition includes at least one active agent. In certain embodiments the active agent is soluble in the composition.

In one aspect, foamable compositions are provided which include (a) jojoba oil, (b) a stabilizer component, (c) water, and (d) a propellant. In some embodiments, the jojoba oil is present in the composition at a concentration of at least about 10% by weight.

In some embodiments, the stabilizer component includes a non-ionic surface active agent, a polymeric agent or a mixture of a non-ionic surface active agent and a polymeric agent. Exemplary polymeric agents include, without limitation a bioadhesive agent, a gelling agent, a film forming agent and a phase change agent. In some embodiments, the polymeric agent is present in the composition at a concentration of about 0.01% to about 5% by weight.

In some embodiments, the propellant is a liquefied hydrocarbon gas propellant. In some embodiments, the ratio of the combination of the wax, the stabilizer component and the water to the propellant is about 100:3 by weight to about 100:35 by weight.

In some embodiments, the composition is substantially free from crystals and is substantially flowable.

In some embodiments, the foamable composition is stored in a pressurized container. Upon release from the pressurized container, the resulting foam is breakable.

In one aspect, a foamable composition is provided that includes:
  a. a liquid wax including at least one fatty acid or at least one fatty alcohol;
  b. a stabilizer component including a non ionic surface-active agent, a polymeric agent or a mixture thereof;
  c. water; and
  d. a liquefied hydrocarbon gas propellant, wherein the ratio of the liquid wax, the stabilizer and water to the gas propellant is about 100:3 by weight to about 100:35 by weight.

When the liquid wax includes at least one fatty acid, the fatty acid is present in the composition at a concentration of at least about 35% by weight. When the liquid wax includes at least one fatty alcohol, the fatty alcohol is present in the composition at a concentration of at least about 12% by weight. The composition is substantially free from crystals and is substantially flowable. When the stabilizer component includes a polymeric agent, the polymeric agent is present in the vehicle composition at a concentration of about 0.01% to about 5% by weight. The polymeric agent is a bioadhesive agent, a gelling agent, a film forming agent or a phase change agent. Upon release from a pressurized container, the foam produced is breakable.

In an embodiment the composition further includes a solid wax.

In another aspect, a foamable composition is provided that includes
  a. at least about 7% by weight of a solid wax;
  b. a liquid wax wherein the liquid wax includes at least one fatty acid or at least one fatty alcohol
  c. a stabilizer including a non ionic surface-active agent, a polymeric agent or a mixture thereof;
  d. water; and
  e. a liquefied hydrocarbon gas propellant, wherein the ratio of the solid wax, the liquid wax, the stabilizer and water to the gas propellant is about 100:3 by weight to about 100:35 by weight.

The composition is substantially free from crystals and is substantially flowable. When the stabilizer component includes a polymeric agent, the polymeric agent is present in the vehicle composition at a concentration of about 0.01% to about 5% by weight. The polymeric agent is a bioadhesive agent, a gelling agent, a film forming agent or a phase change agent. Upon release from a pressurized container, the foam produced is breakable.

In some embodiments, the composition includes at least one liquid fatty acid. The liquid fatty acid is present in the composition at a concentration of at least about 35% by weight. In some embodiments, the composition includes at least one liquid fatty alcohol. The liquid fatty alcohol is present in the composition at a concentration at least about 12% by weight.

In one or more embodiments the wax foamable compositions further include an active agent.

In a further aspect, a foamable composition is provided that includes:
  a. at least about 10% by weight jojoba oil;
  b. a stabilizer component including a surface-active agent, a polymeric agent or a mixture thereof;
  c. water; and
  d. a liquefied hydrocarbon gas propellant, wherein the ratio of the component, the stabilizer and water to the gas propellant is about 100:3 by weight to about 100:35 by weight.

The composition is substantially free from crystals and is substantially flowable. When the stabilizer component includes a polymeric agent, the polymeric agent is present in the vehicle composition at a concentration of about 0.01% to about 5% by weight. The polymeric agent is a bioadhesive agent, a gelling agent, a film forming agent or a phase change agent. Upon release from a pressurized container, the foam produced is breakable.

In one or more embodiments the jojoba foamable composition further includes an active agent.

In some embodiments, there are provided vehicles and foam formulations in which the hydrophobic wax is liquid wax. In particular, in some embodiments, there are provided formulations where the wax includes a liquid fatty acid. Similarly there are provided in some embodiments formulations where the wax includes a liquid fatty alcohol. In other embodiments, there are further provided formulations where the liquid wax includes at least one fatty acid and at least one fatty alcohol. The fatty wax is present in the composition at a concentration of at least about 30 wt %; at least about 35 wt %; at least about 40 wt %; at least about 50 wt %; or at least about 60 wt %. The fatty alcohol is present in the composition at a concentration of at least about 7.5 wt %; at least about 10 wt %; at least about 20 wt %; at least about 30 wt %; at least about 40 wt %; at least about 50 wt %; or at least about 60 wt %.

In some embodiments, there are provided vehicles and foam formulations in which the hydrophobic wax is a combination of liquid wax and solid wax where the solid wax is at least about 7 wt %; at least about 10 wt %; at least about 20 wt %; at least about 30 wt %; or at least about 40 wt %.

In some embodiments, there are provided vehicles and foam formulations in which there is a high level of fatty acids. For example, in some embodiments the fatty acids are in excess of about 30%; in excess of about 40%; in excess of about 50%; or in excess of about 60% by weight of the formulation.

In some embodiments, there are provided vehicles and foam formulations in which there is a high level of fatty acids and fatty alcohols combined. For example, in some embodiments, the fatty acids and fatty alcohols are in excess of about 35%; in excess of about 37%; in excess of about 40% in excess of about 50%; and in excess of about 60%; by weight of the formulation.

In some embodiments, there are provided vehicles and foam formulations in which there is a high level of fatty acids and or fatty acids and fatty alcohols combined together with a non basic active agent (e.g., a neutral active agent or an acidic active agent). For example, in some embodiments, the fatty acids alone or combined with fatty alcohols are in excess of about 30%; in excess of about 35%; in excess of about 40%; in excess of about 50%; and in excess of about 60%; by weight of the formulation. By "non basic active agent" is meant an active agent that when present in a therapeutically effective amount does not cause a significant amount of neutralization of an acid formulation. By significant is intended to be about 20% or more neutralization.

In some embodiments, there are provided vehicles and foam formulations in which there is a high level of fatty acids alone or fatty acids and fatty alcohols combined wherein one of the fatty acids is solid and the presence of liquid wax enables the solid wax to solubilize at high concentrations. For example, in some embodiments, the fatty acids and fatty alcohols are in excess of about 37%; in excess of about 40%; in excess of about 50%; or in excess of about 60% by weight of the formulation.

In some embodiments, there are provided vehicles and foam formulations in which the amount of jojoba oil is more than 10% by weight of the formulation.

In some embodiments, there are provided vehicles and foam formulations in which the wax, stabilizer and water and amounts thereof generate an emulsion that is substantially resistant to phase reversal.

In some embodiments, there are provided vehicles and foam formulations in which the polymer or the polymeric agent is a polymeric surfactant.

In one or more embodiments any of the vehicles and foam formulations described herein also include an active agent. In some embodiments the formulations include at least one other active agent (i.e., two or more active agents in the composition).

In some embodiments, there is also provided a formulation of any of the compositions described above wherein the composition is in a non foam state.

In some embodiments, there is also provided a formulation of any of the compositions described above for use in the manufacture of a medicament.

In one aspect, a method of treating, ameliorating or preventing a disorder of a mammalian subject is provided. The method includes administering any of the compositions described herein to a target site.

DETAILED DESCRIPTION

The present invention relates to an aqueous composition comprising wax for use as vehicle, therapeutic, cosmetic or pharmaceutical composition.

According to one or more embodiments, the composition includes: a pharmaceutical or cosmetic vehicle composition comprising:
  a. at least one hydrophobic wax selected from the group consisting of a liquid wax, a solid wax and mixtures thereof;
  b. at least one stabilizer selected from the group consisting of a surface-active agent, a polymeric agent and mixtures thereof; and
  c. water,
wherein the vehicle is substantially free from crystals and is substantially flowable.

According to one or more embodiments, the hydrophobic wax comprises a liquid wax and a solid wax, wherein the liquid wax concentration in relation to the solid wax concentration is effective to dissolve any solid wax crystals in the composition. In an embodiment the composition further comprises a liquefied hydrocarbon gas propellant, wherein the ratio of the wax, the stabilizer and water to the gas propellant is about 100:3 by weight to about 100:35 by weight, wherein upon release from a pressurized container the composition expands to form a breakable foam.

According to one or more embodiments, the composition includes: a foamable composition comprising:
a. a liquid wax comprising at least one fatty acid or at least one fatty alcohol;
b. a stabilizer component comprising a non ionic surface-active agent, a polymeric agent or a mixture thereof;
c. water; and
d. a liquefied hydrocarbon gas propellant, wherein the ratio of the liquid wax, the stabilizer and water to the gas propellant is about 100:3 by weight to about 100:35 by weight;
wherein, when the liquid wax comprises at least one fatty acid, the fatty acid is present in the composition at a concentration of at least about 35% by weight and wherein, when the liquid wax comprises at least one fatty alcohol, the fatty alcohol is present in the composition at a concentration of at least about 12% by weight;
wherein the composition is substantially free from crystals and is substantially flowable;
wherein, when the stabilizer component comprises a polymeric agent, the polymeric agent is present in the vehicle composition at a concentration of about 0.01% to about 5% by weight and includes a bioadhesive agent, a gelling agent, a film forming agent and a phase change agent; and
wherein, upon release from a pressurized container, the foam produced is breakable.

In an embodiment the composition further comprises a solid wax.

According to one or more embodiments, the composition includes: a foamable composition comprising
a. at least about 7% by weight of a solid wax;
b. a liquid wax wherein the liquid wax comprises at least one fatty acid or at least one fatty alcohol
c. a stabilizer comprising a non ionic surface-active agent, a polymeric agent or a mixture thereof;
d. water; and
e. a liquefied hydrocarbon gas propellant, wherein the ratio of the solid wax, the liquid wax, the stabilizer and water to the gas propellant is about 100:3 by weight to about 100:35 by weight;
wherein the composition is substantially free from crystals and is substantially flowable;
wherein, when the stabilizer component comprises a polymeric agent, the polymeric agent is present in the vehicle composition at a concentration of about 0.01% to about 5% by weight and includes a bioadhesive agent, a gelling agent, a film forming agent and a phase change agent; and
wherein, upon release from a pressurized container, the foam produced is breakable.

In one or more embodiments when the composition comprises at least one liquid fatty acid, the liquid fatty acid is present in the composition at a concentration of at least about 35% by weight and when the composition comprises at least one liquid fatty alcohol, the liquid fatty alcohol is present in the composition at a concentration at least about 12% by weight.

According to one or more embodiments, the polymeric agent is about 0.01% to about 5% by weight and is selected from the group consisting of a bioadhesive agent, a gelling agent, a film forming agent and a phase change agent;

According to one or more embodiments, the wax, stabilizer and water are selected to provide a composition that satisfies one, two, three, four or all of the following
 a) substantially resistant to aging;
 b) substantially resistant to phase separation;
 c) substantially resistant to phase reversal;
 d) can substantially stabilize or solubilize active ingredients; or
 e) can improve skin penetration.

In one embodiment a) to e) above are satisfied.

In one or more embodiments the composition is contained in a pressurized container and further comprises a liquefied hydrocarbon gas propellant. In one or more embodiments, the composition provides a foam upon release. In one or more embodiments, the composition and/or the foam is substantially flowable. In some embodiments, the wax, stabilizer, solvent and propellant are selected to generate a breakable foam of good to excellent quality.

In one embodiment the propellant is added to the total amount of composition, wherein the ratio of the components comprising hydrophobic component, the stabilizer and water to the gas propellant is about 100:3 by weight to about 100:35 by weight. In another embodiment the ratio of the components comprising hydrophobic component, the stabilizer and water to the gas propellant is about 100:5 by weight to about 100:25 by weight; or about 100:7 by weight to about 100:20 by weight.

In one or more embodiments there is provided a composition wherein the hydrophobic wax is at a concentration of at least about 30 wt %; 35 wt % 37 wt %; 40 wt %; 45 wt %; 50 wt %; 55 wt %; or 60 wt %.

In one or more embodiments there is provided a composition in which the hydrophobic wax includes at least one liquid wax present at a concentration of at least about 20 wt % and the composition is substantially free of crystals, wherein the at least one liquid wax comprises a fatty alcohol. In some embodiments, the fatty alcohol is at least about 7.5 wt %; 10 wt %; 12 wt %; or 15 wt % of the composition.

In one or more embodiments there is provided a composition in which the hydrophobic wax includes at least one liquid wax present at a concentration of at least about 30 wt % and the composition is substantially free of crystals, wherein the at least one liquid wax comprises a fatty alcohol. In an alternative embodiment the at least one liquid wax comprises a fatty acid. In some embodiments, the fatty alcohol is at least about 7.5 wt %; 10 wt %; 12 wt %; 15 wt %; 20 wt %; or 25 wt % of the composition.

In one or more embodiments there is provided a composition in which the hydrophobic wax includes at least one liquid wax present at a concentration of at least about 35 wt % and the composition is substantially free of crystals, wherein the at least one liquid wax comprises a fatty alcohol. In an alternative embodiment the at least one liquid wax comprises a fatty acid. In some embodiments, the fatty alcohol is at least about 7.5 wt %; 10 wt %; 12 wt %; 15 wt %; 20 wt %; 25 wt %; or 30 wt %. of the composition In one or more embodiments there is provided a composition in which the hydrophobic wax includes at least one liquid wax present at a concentration of at least about 40 wt % by weight and the composition is substantially free of crystals wherein the at least one liquid wax comprises a fatty alcohol. In an alternative embodiment the at least one liquid wax comprises a fatty acid. In some embodiments, the fatty alcohol is at least about 7.5 wt %; 10 wt %; 12 wt %; 15 wt %; 20 wt %; 25 wt %; 30 wt % or 35 wt % of the composition.

In one or more further embodiments the liquid wax is at least about 45 wt %; and the fatty alcohol comprises at least about 7.5 wt %; 10 wt %; 15 wt %; 20 wt %; 25 wt %; 30 wt %; 35 wt % or 40 wt %; or the liquid wax is at least about 50 wt %; and the fatty alcohol comprises at least about 7.5 wt %; 10 wt %; 15 wt %; 20 wt %; 25 wt %; 30 wt %; 35 wt %; 40 wt %; or 45 wt % or the liquid wax is at least about 55 wt %; and the fatty alcohol comprises at least about 7.5 wt %; 10 wt %; 15 wt %; 20 wt %; 25 wt %; 30 wt %; 35 wt %; 40 wt %; 45 wt %; 50 wt % or the liquid wax comprises at least about 60 wt %; and the fatty alcohol comprises at least about 7.5 wt %; 10 wt %; 12 wt %; 15 wt %; 20 wt %; 25 wt %; 30 wt %; 35 wt %; 40 wt %; 45 wt %; 50 wt %; or 55 wt %.

In one or more embodiments there is provided a composition in which the hydrophobic wax includes at least one liquid wax present at a concentration of at least about 30%, about 35% about 40% or about 45% by weight and the composition is substantially free of crystals and is substantially flowable.

In one or more embodiments there is provided a composition in which the hydrophobic wax present in the composition includes at least one solid wax and at least one liquid wax, wherein the liquid wax is at a concentration of at least about 20 wt %; 25 wt %; 30 wt %; 35 wt % 37 wt %; 40 wt %; 45 wt %; 50 wt %; 55 wt %; or 60 wt % by weight and the composition is substantially free of crystals.

In one or more embodiments there is provided a composition in which the hydrophobic wax present in the composition is at a concentration of at least about 40% by weight and comprises at least one solid wax and the composition is substantially free of crystals.

In one or more embodiments there is provided a composition in which the hydrophobic wax comprises at least one liquid wax and at least one solid wax present at a concentration of at least about 40% by weight and the composition is substantially free of crystals, wherein the liquid wax is a fatty acid.

In one or more embodiments there is provided a composition in which the hydrophobic wax present in the composition comprises at least about 7 wt % of at least one solid wax and at least one liquid wax, and the composition is substantially free of crystals. In some embodiments, the solid wax is at a concentration of at least about 7.5 wt %; 10 wt %; 15 wt %; 20 wt %; 25 wt %; 30 wt %; 35 wt % or 40 wt %. In a further embodiment where the solid wax is at least about 7% or more the liquid wax is at a concentration of at least about 7.5 wt %; 10 wt %; 15 wt %; 20 wt %; 25 wt %; 30 wt %; 35 wt % or 40 wt %.

In one or more embodiments there is provided a composition substantially free of crystals, wherein the hydrophobic wax comprises at least one liquid wax and at least one solid wax present at a concentration of at least about 36% by weight, wherein the amount of solid wax is at least about 8% or wherein the ratio of liquid wax to solid wax is between about 9:2 to about 1:6. For example, in one embodiment, the amount of hydrophobic wax is about 36% and the amount of solid wax is at least about 8% and the amount of liquid wax is about 28%. Similarly, in one embodiment the amount of solid wax is about 10% and the amount of liquid wax is 26%. Likewise, if the amount of hydrophobic wax is about 38% and the amount of solid wax is about at least 8% then the liquid wax is about 30%. Similarly, if the amount of solid wax is about 10% the amount of liquid wax is 28% and so on. More particularly the ratio of liquid wax to solid was is about 9:2; about 4:1; about 3:1; about 2:1; about 1:1; about 1:2; about 1:3; about 1:4 about 1:5 or about 1:6 or anything in between these ratios.

In one or more embodiments the ratio of fatty alcohol to fatty acid is between about 10:9 to about 8:1

In one or more embodiments the ratio of liquid wax to solid wax is between about 10:1 to about 1:10. In one or more other embodiments the ratio of liquid wax to solid wax is between about 5:1 to about 1:5. In one or more further embodiments the ratio of liquid wax to solid wax is between about 1:1 to about 3:1. Alternatively in one or more embodiments the ratio of liquid wax to solid wax is between about 3:1 to about 1:1.

In one or more embodiments there is provided a composition in which the hydrophobic wax includes at least one liquid wax, wherein the liquid wax comprises at least about 10% jojoba oil.

In one or more embodiments there is provided a composition in which the hydrophobic wax comprises at least one liquid wax present at a concentration of at least about 20% by weight, wherein the liquid wax comprises at least about 10% jojoba oil;

In one or more embodiments there is provided a composition in which the hydrophobic wax comprises at least one liquid wax present at a concentration of at least about 30% by weight, wherein the liquid wax comprises at least about 20% jojoba oil.

In one or more embodiments there is provided a composition in which the hydrophobic wax comprises at least about 20% jojoba oil; at least about 30% jojoba oil; at least about 40% jojoba oil; at least about 50% jojoba oil; at least about 60% jojoba oil; or at least about 70% jojoba oil;

In one or more embodiments there is provided a composition in which the hydrophobic wax combination comprises solid wax at a concentration of about 30 wt % or more and the composition is substantially free of crystals.

In one or more embodiments there is provided a composition in which the solid wax is at a concentration of about or less than 37 wt %. In one or more embodiments the compositions described herein further include an active agent.

In an embodiment the active agent is soluble in the composition at an acidic pH. In another embodiment the active agent is non basic or does not cause significant neutralization of the composition. In an embodiment the active agent is solubilized by first dissolving the active agent directly in organic hydrophobic liquid wax or an organic wax or a combination thereof.

In one or more embodiments the compositions described herein include a solvent. Exemplary solvents include, without limitation an organic carrier, a hydrophilic solvent; a hydrophobic solvent; a potent solvent; a polar solvent, a silicone, an emollient, and mixtures thereof.

In one or more embodiments there is provided a composition, wherein the wax, stabilizer and water are selected to generate a surfactant layer or interphase with substantially organized chaos.

In one or more embodiments there is provided a composition, wherein the breakable foam comprises a micro or nano emulsion.

In one or more embodiments there is provided a composition, which is substantially resistant to one or more Freeze-Thaw cycles (FTC).

In one or more embodiments the surface-active agent is a solid, a liquid or a mixture thereof.

Exemplary surface active agents for use in the compositions described herein include a polysorbate, polyoxyethylene (20) sorbitan monostearate, polyoxyethylene (20) sorbitan monooleate, a polyoxyethylene fatty acid ester, Myrj 45, Myrj 49, Myrj 52, Myrj 59, a polyoxyethylene alkynyl ether, polyoxyethylene cetyl ether, polyoxyethylene palmityl ether, polyethylene oxide hexadecyl ether, polyethylene glycol cetyl ether, brij 38, brij 52, brij 56 and brij W1, a sucrose ester, a partial ester of sorbitol, sorbitan monolaurate, sorbitan monolaurate a monoglyceride, a diglyceride, isoceteth-20, a sucrose ester, steareth 2, glyceryl monostearate/PEG 100 stearate, Glyceryl Stearate, Steareth-21, peg 40 stearate, polysorbate 60, polysorbate 80, sorbitan stearate, laureth 4, Sorbitan monooleate, ceteareth 20, steareth 20, ceteth 20, Macrogol Cetostearyl Ether, ceteth 2, PEG-30 Dipolyhydroxystearate, sucrose distearate, polyoxyethylene (100) stearate, PEG 100 stearate, PEG 40 stearate, laureth 4, cetomacrogol ether, Cetearyl alcohol, Cetearyl glucoside, Oleyl alcohol, Steareth-2, Diisopropyl adipate, Capric/caprilic triglicerides, Polysorbate 20; Montanov 68 (CETEARYL ALCOHOL (and) CETEARYL GLUCOSIDE.), Sharonmix 824 (a liquid blend of methyl paraben, ethyl paraben and propyl paraben—in phenoxyethanol), Simusol 165 (Glyceryl stearate and PEG-100 stearate). Methyl glucose sequistearate, Peg 30 dipolyhydroxystearate, sucrose stearic acid esters, sorbitan laureth, sorbitan stearate and mixtures thereof.

In one or more embodiments there is provided a composition, wherein the surface active agent comprises a polysorbate.

In one or more embodiments there is provided a composition, wherein the surface active agent comprises PEG 30 dipolyhydroxysearate.

In one or more embodiments there is provided a composition, wherein the surface active agent also functions as a solvent.

In one or more embodiments there is provided a composition, wherein the polymeric agent is selected from the group consisting of carbopol 934, pemulen TR2, klucel EF, xanthan gum, methocel A4M, and carboxy methyl cellulose or selected from the group consisting of locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, an amine-bearing polymer, chitosan, alginic acid, hyaluronic acid, a chemically modified starch, a carboxyvinyl polymer, polyvinylpyrrolidone, polyvinyl alcohol, a polyacrylic acid polymer, a polymethacrylic acid polymer, polyvinyl acetate, a polyvinyl chloride polymer, a polyvinylidene chloride polymer, methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, a cationic cellulose, aluminum starch octenylsuccinate (ASOS), sodium starch octenylsuccinate, PEG 1000, PEG 4000, PEG 6000 and PEG 8000.

In one or more embodiments there is provided a composition, wherein the polymeric agent is a derivatized polymeric emulsifier. In one or other embodiments the polymer is a polymeric surfactant. Non limiting examples are a poloxamer or a pemulen.

The foamable composition can be an emulsion, or microemulsion, including an aqueous phase and an organic carrier phase, which comprises at least one hydrophobic solvent, which is a wax, selected from the group consisting of (1) a fatty alcohol; (2) a fatty acid; and (3) certain naturally occurring waxes. The wax, according to the present invention is hydrophobic. A "hydrophobic solvent" as used herein refers to a material having solubility in distilled water at ambient temperature of less than about 1 gm per 100 mL, in some embodiments less than about 0.5 gm per 100 mL, and in other embodiments less than about 0.1 gm per 100 mL. It is semi-solid or liquid at ambient temperature. The identification of a "hydrophobic solvent", as used herein, is not intended to characterize the solubilization capabilities of such solvent for any specific active agent or any other component of the foamable composition. Rather, such information is provided to aid in the identification of materials suitable for use as a hydrophobic component in the foamable compositions described herein.

Examples of waxes, suitable as hydrophobic solvents in accordance to the present invention include, but are not limited, to the following:

In one or more embodiments there is provided a composition, wherein the wax is a C8 to C22 fatty acid or fatty alcohol.

In one or more embodiments there is provided a composition, wherein the wax is a C16 to C20 fatty acid or fatty alcohol.

In one or more embodiments there is provided a composition, wherein the wax is a branched chain fatty acid or fatty alcohol.

In one or more embodiments there is provided a composition, wherein the wax is a straight chain fatty acid or fatty alcohol.

In one or more embodiments there is provided a composition, wherein the wax is a saturated fatty acid or fatty alcohol.

In one or more embodiments there is provided a composition, wherein the wax is an unsaturated fatty acid or fatty alcohol.

In one or more embodiments there is provided a composition, wherein the wax is selected from the group consisting of isostearic acid, oleic acid, oleyl alcohol, stearic acid, cetyl alcohol, stearyl alcohol, erucic acid, linoleic acid, arachidonic acid and linolenic acid.

In one or more embodiments there is provided a composition, wherein the wax is selected from the group consisting of: lauric acid, myristic acid, palmitic acid, stearic acid, behenic acid, oleic acid, 12-hydroxystearic acid, undecylenic acid, tall acid, isostearic acid, linoleic acid, linolenic acid, eicosapentaenoic acid (EPA), docosahexaenoic acid (DHA), and an equivalent fatty alcohol thereof.

In one or more embodiments there is provided a composition, wherein the wax is selected from the group consisting of animal waxes, spermaceti, lanolin (wool wax), insect waxes, beeswax, chinese wax, vegetable waxes, candelilla wax, castor wax, jojoba oil, rice bran wax; petroleum waxes, paraffin waxes, microcrystalline wax; synthetic waxes, polyethylene waxes, Fischer-Tropsch waxes, chemically modified and substituted waxes; and mineral waxes.

In one or more embodiments there is provided a composition, wherein the wax is selected from the group consisting of coconut oil, palm oil, tallow and jojoba oil.

In one or more embodiments there is provided a composition, wherein the wax is jojoba oil.

In one or more embodiments there is provided a composition further comprising an additional active agent.

In one or more embodiments there is provided a composition, further containing a foam adjuvant. In one or more embodiments certain hydrophobic waxes can function as a foam adjuvant. Solid hydrophobic waxes are preferred. Thus, In addition to the hydrophobic wax acting as the main "oil" phase it can contribute to the foam stability and quality. Mixtures of solid wax with liquid wax can be ideal where for example, depending on the actual ingredients used, a solid wax primarily acts as the adjuvant and a liquid wax as the solvent and co adjuvant.

In one or more embodiments there is provided a composition further containing at least one organic carrier (other than wax) selected from the group consisting of a hydrophobic organic carrier, an emollient and mixtures thereof, at a concentration of about 2% to about 50% by weight.

In one or more embodiments there is provided a composition, wherein the organic carrier is selected from the group consisting of mineral oil, triglycerides, medium chain triglyceride (MCT) oil, capric/caprylic triglyceride, alkyl esters of fatty acids such as isopropyl palmitate, isopropyl myristate, isopropyl isostearate, poly propylene glycol 15-stearly ether, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, maleated soybean oil, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; essential oils; and silicone oils, such as dimethicone, cyclomethicone, polyalkyl siloxane, polyaryl siloxane, polyalkylaryl siloxane, a polyether siloxane copolymer and a poly(dimethylsiloxane)-(diphenyl-siloxane) copolymer and a polypropylene glycol alkyl ether.

In one or more embodiments there is provided a composition further containing at least one polar solvent.

In one or more embodiments there is provided a composition, wherein the polar solvent is selected from the group consisting of dimethyl isosorbide, glycerol, propylene glycol, hexylene glycol, diethylene glycol, propylene glycol n-alkanols, terpenes, di-terpenes, tri-terpenes, limonene, terpene-ol, 1-menthol, dioxolane, ethylene glycol, other glycols, oleyl alcohol, alpha-hydroxy acids, such as lactic acid and glycolic acid, sulfoxides, such as dimethylsulfoxide (DMSO), dimethylformanide, methyl dodecyl sulfoxide, dimethylacetamide, azone (1-dodecylazacycloheptan-2-one), 2-(n-nonyl)-1,3-dioxolane, alkanols, such as dialkylamino acetates, and admixtures thereof.

In one or more embodiments there is provided a composition, wherein the organic carrier is capric/caprylic triglyceride.

In one or more embodiments there is provided a composition, wherein the wax, stabilizer and water are selected to generate an emulsion that can produce a substantially strong and closed packed barrier between the oil and the water phases whilst maintaining a fluid constitution and a surfactant layer or interphase with substantially organized chaos.

In one or more embodiments there is provided a composition, further comprising an additional component selected from the group consisting of a modulating agent, a polar solvent, an anti perspirant, an anti-static agent, a buffering agent, a bulking agent, a chelating agent, a colorant, a conditioner, a deodorant, a diluent, a dye, an emollient, fragrance, a humectant, an occlusive agent, a penetration enhancer, a perfuming agent, a permeation enhancer, a pH-adjusting agent, a preservative, a skin penetration enhancer, a sunscreen, a sun blocking agent, a sunless tanning agent, and a vitamin.

In one or more embodiments there is provided a therapeutic or pharmaceutical composition comprising:
  i. at least one hydrophobic wax selected from the group consisting of a liquid wax, a solid wax and mixtures thereof;
  ii. at least one stabilizer selected from the group consisting of a surface-active agent, a polymeric agent and mixtures thereof;
  iii. water;
  iv. an active agent; and
  v. a liquefied hydrocarbon gas propellant, wherein the ratio of the solid wax, the liquid wax, the stabilizer and water to the gas propellant is about 100:3 by weight to about 100:35 by weight;
  wherein the vehicle is substantially free from crystals, is substantially flowable and upon release from a pressurized container provides a breakable foam.

The term therapeutic composition includes pharmaceutical composition and both these terms can be used interchangeably.

In an embodiment where the pharmaceutical composition comprises a liquid wax and a solid wax, the stabilizer comprises about 1% to about 5% of at least one surface-active agent and about 1% to about 5% of at least one polymeric agent.

In one or more embodiments there is provided a therapeutic composition, wherein the active agent is selected from the group consisting of active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, antiyeast agents, antiwart agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, steroids, non-steroidal anti-inflammatory agents, oxidizing agents, pediculicides, photodynamic therapy agents, retinoids, sanatives, scabicides, self tanning agents, skin whitening agents, vasoconstrictors, vasodilators, vitamins, vitamin D derivatives, wound healing agents and wart removers as well as agents having activity against superficial basal cell carcinomas, actinic keratoses, Bowen's disease and or other squamous cell carcinomas and molluscum contagiosum.

In one or more embodiments there is provided a therapeutic composition, wherein the wax is present in the composition in an amount sufficient to solubilize the active agent.

In one or more embodiments there is provided a therapeutic composition, wherein the active agent is selected from the group consisting of at least one of imiquimod, resiquimod, gardiquimod, an interferon, an immunomodulator, podophyllin (anti-mitotic), podofilox, 5-fluorouracil (5-FU), and trichloroacetic acid (TCA), fluorouracil, afovirsen, inosine pranobex, podophyllum, trichloroacetic acid, thiotep, diclofenac, 5-aminolevulinic acid and derivatives, tretinoin, a cyclic peptide, cyclosporine, tacrolimus, tresperimus, pimecrolimus, sirolimus, verolimus, laflunimus and laquinimod.

In one or more embodiments there is provided a therapeutic composition, wherein the active agent is imiquimod.

In one or more embodiments there is provided a therapeutic composition, wherein the active agent is used against herpes simplex virus infections, other viral infections and eczema and as a vaccine adjuvant.

In one or more embodiments there is provided a therapeutic composition, wherein imiquimod is used in combination with at least one of the group consisting of meglumine antimoniate; cryotherapy; acyclovir; 5-aminolevulinic acid; fluorouracil; salicylic acid a COX inhibitor and sulindac.

In one or more embodiments there is provided a therapeutic composition, wherein the active agent is a steroid.

In one or more embodiments there is provided a therapeutic composition, wherein the steroid is selected from the group consisting of hydrocortisone, hydroxyltriamcinolone, alpha-methyl dexamethasone, dexamethasone-phosphate, beclomethsone dipropionate, clobetasol valemate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortmate, mepreddisone, paramethasone, prednisolone, prednisone, beclomethasone dipropionate, and triamcinolone.

In one or more embodiments there is provided a therapeutic composition, wherein the active agent is an immunomodulator.

In one or more embodiments there is provided a therapeutic composition, wherein the immunomodulator is selected from the group consisting of a cyclic peptide, cyclosporine, tacrolimus, tresperimus, pimecrolimus, sirolimus, verolimus, laflunimus, laquinimod and imiquimod.

In one or more embodiments there is provided a therapeutic composition, wherein the wax is present in the composition in an amount sufficient to solubilize the immunomodulator.

In one or more embodiments there is provided a therapeutic composition, wherein the composition further comprises a solvent selected from the group consisting of an organic carrier, a hydrophilic solvent; a hydrophobic solvent; a potent solvent; a polar solvent, a silicone, an emollient, and mixtures thereof.

In one or more embodiments there is provided a therapeutic composition, wherein the wax, stabilizer and water are selected to generate an emulsion that is substantially resistant to phase reversal.

In one or more embodiments there is provided a therapeutic composition, wherein the wax, stabilizer and water are selected to generate a surfactant layer or interphase with substantially organized chaos.

In one or more embodiments there is provided a method of treating, ameliorating or preventing a disorder of a mammalian subject, comprising: administering a foamable therapeutic composition to a target site, the composition comprising:
a. a therapeutically effective amount of an active agent;
b. at least one hydrophobic wax selected from the group consisting of a liquid wax, a solid wax and mixtures thereof;
c. at least one stabilizer selected from the group consisting of a surface-active agent, a polymeric agent and mixtures thereof; and
d. water;
e. a liquefied hydrocarbon gas propellant, wherein the ratio of the solid wax, the liquid wax, the stabilizer and water to the gas propellant is about 100:3 by weight to about 100:35 by weight;
wherein the vehicle is substantially free from crystals, is substantially flowable and upon release from a pressurized container provides a breakable foam.

In one or more embodiments there is provided a method of treating, wherein the composition is contained in a pressurized container and further comprises a liquefied hydrocarbon gas propellant at a concentration of about 3% to about 35% by weight of the total composition, is substantially flowable and provides a foam upon release and wherein the wax, stabilizer and water are selected to generate a breakable foam of good to excellent quality.

In one or more embodiments there is provided a method of treating, wherein the target site is selected from the group consisting of the skin, a body cavity, a mucosal surface, the nose, the mouth, the ear canal, the vagina and the rectum.

In one or more embodiments there is provided a method of treating, wherein the disorder is selected from the group consisting of dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, eethyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo; and wherein the active agent is suitable for treating said disorderm or is selected from the group consisting of chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranuloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum; warts; herpes simplex virus infections, other viral infections, superficial basal cell carcinomas, actinic keratoses, Bowen's disease and/or other squamous cell carcinomas, molluscum contagiosum and eczema, and wherein the active agent is suitable for treating said disorder.

In one or more embodiments there is provided a method of treating, wherein the disorder is a dermatological disorder, which can be treated, ameliorated or prevented by a topical steroid, an immunomodulator or an anti-infective agent.

In one or more embodiments there is provided a method of treating, wherein the active agent is selected from the group consisting of imiquimod, resiquimod, gardiquimod, an interferon, an immunomodulator, podophyllin (anti-mitotic), podofilox, 5-fluorouracil (5-FU), and trichloroacetic acid (TCA), fluorouracil, afovirsen, inosine pranobex, podophyllum, trichloroacetic acid, thiotep, diclofenac, 5-aminolevulinic acid and derivatives, tretinoin, a cyclic peptide, cyclosporine, tacrolimus, tresperimus, pimecrolimus, sirolimus, verolimus, laflunimus and laquinimod.

In one or more embodiments there is provided a pharmaceutical composition, further comprising an additional component selected from the group consisting of a modulating agent, a polar solvent, an anti perspirant, an anti-static agent, a buffering agent, a bulking agent, a chelating agent, a colorant, a conditioner, a deodorant, a diluent, a dye, an emollient, fragrance, a humectant, a moisturizer, an occlusive agent, a penetration enhancer, a perfuming agent, a permeation enhancer, a pH-adjusting agent, a preservative, a skin penetration enhancer, a sunscreen, a sun blocking agent, a sunless tanning agent, In one or more embodiments there is provided a pharmaceutical composition comprising:
  i. a liquid wax selected from the group consisting of isostearic acid, oleyl alcohol, octyldodecanol, isostearyl alcohol and jojoba oil;
  ii. a stabilizer comprising about 1% to about 5% of at least one surface-active agent comprising a liquid surfactant and about 0.1% to about 5% of at least one polymeric agent;
  iii. water; and
  iv. an active agent,
wherein the composition is substantially free from crystals, is substantially flowable and upon release from a pressurized container provides a breakable foam;
wherein the liquid wax is about 7% to about 70% by weight of the composition.

In one or more embodiments there is provided a pharmaceutical composition comprising:
  i. a liquid wax selected from the group consisting of isostearic acid, oleyl alcohol, octyldodecanol, isostearyl alcohol, and jojoba oil and a solid wax selected from the group consisting of stearic acid, cetyl alcohol and stearyl alcohol;
  ii. a stabilizer comprising about 1% to about 5% of at least one surface-active agent comprising a liquid surfactant and about 0.1% to about 5% of at least one polymeric agent;
  iii. water; and
  iv. an active agent,
wherein the vehicle is substantially free from crystals, is substantially flowable and upon release from a pressurized container provides a breakable foam.

In one or more embodiments the ranges of an ingredient can be between any two figures mentioned for that ingredient.

In one or more embodiments the ranges of a ratio between two substances A:B can be between any two sets of figures mentioned for that ratio.

In one or more embodiments there is provided a vehicle or a therapeutic or a pharmaceutical composition in a non foam state.

In one or more embodiments there is also provided a formulation of any of the compositions described herein for use in the manufacture of a medicament.

In one aspect, a method of treating, ameliorating or preventing a disorder of a mammalian subject is provided. The method includes administering any of the compositions described herein to a target site.

All % values are provided on a weight (w/w) basis.

Wax

In an embodiment, the organic carrier comprises a wax. By wax is meant in the wider sense, waxes, waxy substances, counterparts and derivatives thereof. Waxes may be natural such as beeswax, carnauba and paraffin or artificial. Some artificial materials that exhibit similar properties are also described as wax or waxy. Chemically, a wax may be an ester of ethylene glycol (ethan-1,2-diol) and two fatty acids, as opposed to a fat which is an ester of glycerin (propan-1,2,3-triol) and three fatty acids. It may also be a combination of other fatty alcohols with fatty acids. Non limiting examples of: animal waxes are spermaceti and lanolin (wool wax); insect waxes are beeswax and chinese wax; vegetable waxes are candelilla wax, castor wax, jojoba oil and rice bran wax; petroleum waxes are paraffin waxes and microcrystalline wax; synthetic waxes are polyethylene waxes Fischer-Tropsch waxes, chemically modified and substituted waxes; and mineral waxes. Formerly waxes were fatty acid esters with monohydric fatty alcohols having wax like properties, however, the category has been widely extended to include any organic material having wax-like properties. Some typical characteristics of waxes are water repellency being hydrophobic, relatively low viscosity when liquid, and plasticity. In the context herein, a wax can be a solid wax or a liquid wax and includes waxy substances, like fatty acids and their fatty alcohol counterparts, which can be short, medium and long chain. The fatty acid or alcohol backbone may be straight, branched, saturated, unsaturated, or hydrogenated, unhydrogenated, natural, or synthetic. Where one type of backbone produces a waxy substance then molecules with the substantially the same backbone are also deemed as being part of the wax family or being a waxy substance counterpart or derivative thereof. For example, stearic acid and stearyl alcohol are waxy solids with a C18 backbone. In other cases, however, where the carbon backbone chain is also C18, such as isostearic acid, oleic acid and oleyl alcohol, they are liquids but are likewise considered to be waxy substances, having a commonality with regards to the number of carbon atoms in the formula. Also considered within the scope is where hydrogenation would form a wax or waxy substance. The significance of this difference in liquidity of molecules having the same or similar backbone chain on foamable compositions is investigated herein. Other non limiting examples of fatty acids and fatty alcohols having a commonality of formula of backbone C chain are shown in Table 1:

TABLE 1

| Saturated Acid | Solid = S Liquid = L | C Formula Backbone | Unsaturated Acid | Solid = S Liquid = L | C Formula Backbone | Fatty Alcohol | Solid = S Liquid = L | C Formula Backbone |
|---|---|---|---|---|---|---|---|---|
| Butyric | L | C4:0* | | | | | | |
| Caproic | L | C6:0 | | | | | | |
| Caprylic | L | C8:0 | | | | capryl | L | C8:0 |
| Capric | S | C10:0 | | | | 1-nonanol | L | C9:0 |
| | | | | | | Capric (strong skin irritant can be harmful) | L | C10:0 |
| | | | | | | undecanol | L | C11:0 |

TABLE 1-continued

| Saturated Acid | Solid = S Liquid = L | C Formula Backbone | Unsaturated Acid | Solid = S Liquid = L | C Formula Backbone | Fatty Alcohol | Solid = S Liquid = L | C Formula Backbone |
|---|---|---|---|---|---|---|---|---|
| Lauric | S | C12:0 | | | | 1 dodecanol | S | C12:0 |
| Myristic | S | C14:0 | Myristoleic acid: | S | C14:1 | myristyl | S | C14:0 |
| Palmitic | S | C16:0 | | | | cetyl | S | C16:0 |
| | | | Palmitoleic acid: | L | C16:1 | palmitoleyl | | C16:1 |
| Stearic | S | C18:0 | Oleic acid: | L | C18:1 | stearyl | S | C18:0 |
| Isostearic | L | C18:B | | | | isostearyl | L | C18:B |
| | | | | | | oleyl | L | C18:1 |
| | | | Linoleic acid: | L | C18:2 | | | |
| | | | Alpha-linolenic acid: | L | C18:3 | | | |
| Arachidic | S | C20:0 | Arachidonic acid | L | C20:4 | arachidyl | S | C20:0 |
| Behenic | S | C22:0 | Eicosapentaenoic acid | S | C20:5 | behenyl | S | C22:0 |
| | | | Erucic acid: | S | C22:1 | | | |
| | | | Docosahexaenoic acid | S | C22:6 | | | |

*The carbon backbone formula is interpreted as follows: the first number is the number of carbons in the backbone, while the second number is the degree of unsaturation (i.e., number of double bonds). Accordingly, C18:0 refers to a 18-carbon straight chain, while C18:1 refers to 18-carbon straight chain with one double bond and C18:2 refers to 18-carbon straight chain with two double bonds. "B" refers to a branched chain (i.e., C18:B refers to 18-carbon branced chain).

As will be appreciated only those fatty acids and fatty alcohols that are suitable for application to the skin, eyes or body cavity may be used in a pharmaceutical or cosmetic formulation. Capric alcohol for example is known to cause high irritability to skin and eyes and if splashed into the eyes it can cause permanent damage and its use can be harmful. Accordingly, it is excluded from the scope herein.

In selecting a wax in order to make a foamable formulation careful thought must be given not only to whether it is liquid or solid, but also to its length, its shape and its usability in a therapeutic composition. Usability should be looked at both from the aspect of the suitability for the target to which the formulation is to be applied and also from the aspect of whether it can act as a destabiliser or defoamer in the proposed formulation.

In an embodiment, one or both of the fatty alcohol and fatty acid are a straight-chain molecules. In another embodiment one or both are branched. In a further embodiment one or both are saturated and in another embodiment one or both are unsaturated. When unsaturated one or both may be cis or trans unsaturated. Further one or both may be polyunsaturated. In an additional embodiment one or both are hydrogenated and in a different embodiment one or both are unhydrogenated. In an embodiment mixtures of two or more types may be combined.

Additional members are derived from natural products or from synthesis.

As can been seen from Table 1, long, straight chain saturated fatty acids (C10:0 and higher) are solid at room temperature, which does not make them suitable as solvents and makes them difficult to use in higher concentrations for foamable formulations and foam despite their useful properties. The unsaturated long chain fatty acids like e.g. oleic acid are liquid at room temperature, so they are potentially suitable as solvents and easier to use at higher concentrations, but are potentially unstable because of the existence of double bond(s). Branched fatty acids mimic the properties of the straight chain unsaturated fatty acids in many respects. However, they do not have the disadvantage of being unstable. For example branched C18:0 fatty acid (commercially known as isostearic acid) is liquid at room temperature, but is not as unstable as its C18:1 unsaturated counterpart, since unsaturated bonds are absent in branched C18:0. Therefore, branched fatty acids are for many applications more desirable than straight chain fatty acids. (The term "branched fatty acids" is herein to be understood to comprise fatty acids which contain one or more alkyl side groups, which can be attached to the carbon chain at any position. Such alkyl groups are generally short (e.g., having 1-6 carbon atoms, 1-5 carbon atoms, 1-4 carbon atoms, or 1-3 carbon atoms). Branched fatty acids (and similarly branched fatty alcohols) due to their irregular shape can be more chaotic than their straight chain counterparts as is explained in more detail below.

In one or more embodiments the wax, waxy substance, counterpart or derivative thereof is a saturated branched fatty acid or fatty alcohol.

In one embodiment fatty acids which may be used in the fatty acid waxy substances, counterparts or derivatives include those having an alkyl or alkenyl group having 12 or more carbon atoms, in some embodiments 14 to 22 carbon atoms, and in other embodiments 16-22 carbon atoms. Examples of such fatty acid waxes are fatty acids such as lauric acid, myristic acid, palmitic acid, stearic acid, behenic acid, oleic acid, 12-hydroxystearic acid, undecylenic acid, tall acid, isostearic acid, linoleic acid, linolenic acid, eicosapentaenoic acid (EPA), docosahexaenoic acid (DHA), or the equivalent fatty alcohols.

In another embodiment composite fatty acids such as from coconut oil, palm oil, tallow and jojoba oil may be used.

In one or more embodiments, the waxes can be solid substances and in one or more embodiments they may be liquid. In other embodiments a combination of liquid and solid molecules is used.

In an embodiment a saturated fatty acid such as isostearic acid or stearic acid, is preferable due to the stability and the easy overlapping application. These fatty acids may be used alone or in any mixture thereof. For example, for higher concentrations isostearic acid can be used alone or in combination with stearic acid. Indeed, skin feeling can be improved when two or more fatty acids such as stearic acid and isostearic acid are used in combination. The same reasoning is applicable with appropriate changes to fatty alcohols.

In one or more embodiments, the waxes can act as a solvent.

In one or more embodiments, the waxes can act as an emollient.

In one or more embodiments, the waxes can act as a penetration enhancer.

In one or more embodiments, where they are branched or unsaturated they can provide some substantially organized chaos by virtue of their non linear shape enabling both shakability and flowability of the wax formulation and potentially enhanced skin penetration.

Nature moves or tends towards chaos although passing through certain stable states on the way. In a foamable formulation comprising an oil phase and a water phase it is desirable to form a stable emulsion by use of surfactants. Where the surfactant comprises for example, fatty acid or alcohol chains it can form a reasonably tightly packed layer where the said fatty acid or alcohol chains are straight chain and saturated. Relatively speaking such a layer can be considered organised. If unsaturated chains or branched are introduced or used then the molecules are not straight and the backbone can have a mild "v" shape like in oleic acid or in erucic acid or a more pronounced "v" as in linoleic acid or a "u" shape as in arachidonic acid or a half "w" shape as in linolenic acid or a "t" shape in isostearic acid. Without being bound by any theory by using such non linear molecules in forming a foamable composition the surfactant layer or interphase is likely to be less packed and more disrupted making the surfactant layer or interphase in very general terms more fluid and fluidizing, which in turn may improve the flowability of the formulation and or also skin or mucosal membrane penetration. The presence of fatty acids or fatty alcohols in the formulation can interfere with the packing of the surfactant layer or interphase and depending on the surfactants and fatty acids and or alcohols used can improve or disrupt the packing and intern the oil/water interphase. By substantially organized with reference to a surfactant layer of an oil and water or wax and water emulsion is meant a relatively organised well packed layer holding the oil and water or wax and water phases together. By substantially organized chaos it is meant to refer to and to describe a surfactant layer or interphase where comparatively it is to some extent being disrupted and tending towards some chaos or increased liquidity and fluidization or being less tightly packed, due to the selected use of such non linear molecules in the composition. The effect of this substantially organised chaos may vary from formulation to formulation and may be influenced by surface and interfacial tensions. In other words whilst there is an overall structuring effect in the formulation due to the stabiliser and or the fatty acids and or fatty alcohols the effect can be modulated or partially or temporarily disrupted by introducing a non linear molecule which facilitates for example liquidity, fluidization and or penetration. In addition this phenomenon can have an effect on the solubility of certain active agents both in the formulation and or in the interphase.

In one or more embodiments, certain waxes can act as a foam adjuvant.

In one or more embodiments, the fatty alcohol is oleyl alcohol.

Oleyl alcohol occurs as a pale yellow oily liquid and is sometimes used as an antifoaming agent; solubilizing agent/ dissolution enhancer; emollient; emulsifying agent; skin penetrant; and sustained-release agent. Oleyl alcohol is mainly used in topical pharmaceutical formulations and has been used in transdermal delivery formulations. It has been utilized in aerosol formulations of insulin and albuterol. Therapeutically, it has been suggested that oleyl alcohol may exhibit antitumor properties via transmembrane permeation. Oleyl alcohol is soluble in ethanol (95%), and ether but practically insoluble in water and should be stored in a well-closed container in a cool, dry, place. Oleyl alcohol is mainly used in topical pharmaceutical formulations and is generally regarded as a nontoxic and nonirritant material at the levels employed as an excipient although contact dermatitis due to oleyl alcohol has been reported. Oleyl alcohol and propylene glycol are miscible although they are hydrophobic and hydrophilic and therefore it is predicted that it should be possible to make waterless waxy or waxy substances foamable compositions and foam. To the extent that isostearic acid and propylene glycol or stearic acid and propylene glycol are likewise miscible the same will apply to them.

In one or more embodiments, the fatty acid is isostearic acid.

Isostearic acid is a naturally occurring fatty acid, primarily comprising methyl branched isomers of octadecanoic acid. It main uses in the cosmetic and pharmaceutical industries are as a binding agent as an emulsifier/surfactant and as a lubricant It is a nearly water-white liquid with a very low odor. Isostearic acid is an emollient that can form a lipid film on the skin that is permeable to water vapor, oxygen, and carbon dioxide. Isostearic acid is recommended for use in moisturizing cosmetics and is similar to waxes secreted by birds for feather maintenance. Isostearic acid, provides a combination of the properties (from the $C_{18}$ chain length) including retaining the stability of stearic acid the with the liquidity, solubility and physical properties conferred by oleic acid but without the disadvantage of the unsaturation.

In one or more embodiments, the fatty acid is oleic acid.

Oleic acid is a yellowish to pale brown, oily liquid that has been used as an emulsifying agent in topical pharmaceutical formulations. It has also been used as a penetration enhancer in transdermal formulations. It is miscible with ethanol (95%), ether, hexane, and fixed and volatile oils; but practically insoluble in water. On exposure to air, oleic acid gradually absorbs oxygen and darkens in color. At atmospheric pressure, it decomposes when heated at 80-100° C. Oleic acid should be stored in a well-filled, well-closed container, protected from light, in a cool, dry place. Oleic acid is incompatible with aluminum, calcium, heavy metals, iodine solutions, perchloric acid, and oxidizing agents and also reacts with alkalis to form soaps.

In one or more embodiments, the fatty acid is stearic acid.

Stearic acid (octadecanoic acid) is a straight chain fatty acid and may contain palmitic acid. Stearic acid is widely used in oral and topical pharmaceutical formulations and in cosmetics It has been used as an emulsifying agent and solubilizing agent; as a foam adjuvant, a lubricant, and binder. Stearic acid has also been suggested as a sustained-release drug carrier. When partially neutralized with alkalis or triethanolamine, stearic acid is used in the preparation of creams. It is soluble in ethanol (95%), hexane, and propylene glycol but is practically insoluble in water. Stearic acid is incompatible with most metal hydroxides and may be incompatible with oxidizing agents. Studies have suggested possible drug incompatibilities, e.g. with naproxen. Nevertheless, it is generally regarded as a nontoxic and nonirritant material, although it is combustible.

In one or more embodiments, isostearic acid and stearic acid are used in combination.

In one or more embodiments, oleyl alcohol and stearic acid are used in combination.

In one or more embodiments, oleyl alcohol and stearic acid are used in combination.

In one or more embodiments, at least any two from the group consisting of caprilic acid, capryl alcohol, capric acid, capric alcohol, palmitic acid, cetyl alcohol, stearic acid, isostearic acid, stearyl alcohol, and oleyl alcohol are used in combination.

In one or more embodiments, a fatty alcohol is used in combination with a fatty acid. In an embodiment the amount of fatty alcohol is in excess of the amount of fatty acid. In an embodiment the ratio of fatty alcohol to fatty acid is about 10:9, about 5:4, about 4:3, about 3:2, about 2:1, about 3:1, about 4:1, about 5:1, about 8:1, about 10:1, about 20:1, about 40:1, about 80:1, or is any ratio between these ratios.

In one or more embodiments, a liquid wax is used in combination with a solid wax. In an embodiment the amount of liquid wax is in excess of the amount of solid wax. In an embodiment the ratio of liquid wax to solid wax is about 5:4, about 4:3, about 3:2, about 2:1, about 3:1, about 4:1, about 5:1, about 10:1, about 20:1, about 40:1, about 80:1, or is any ratio between these ratios. In another embodiment the amount of solid wax is in excess of the amount of liquid wax. In an embodiment the ratio of solid wax to liquid wax is about 5:4, about 4:3, about 3:2, about 2:1, about 3:1, about 4:1, about 5:1, about 6:1, about 7:1, about 8:1, about 10:1, or is any ratio between these ratios.

In one or more embodiments, the fatty acid and the fatty alcohol can be linked by a linker. A natural example is found in jojoba oil.

Jojoba oil (pronounced "ho-HO-bah") is the liquid wax produced in the seed of the Jojoba (*Simmondsia chinensis*) plant. Jojoba oil is a straight chain wax ester, 36 to 46 carbon atoms in length. Each molecule consists of a fatty acid and a fatty alcohol joined by an ester bond. Each molecule has two points of cis-unsaturation, both located at the 9th carbon atom from either end of the molecule. Jojoba oil comprises approximately 66-71% eicosenoic acid, 14-20% docosenoic acid and 10-13% oleic acid. Refined jojoba oil is colorless and odorless. The melting point of jojoba oil is approximately 10° C. Jojoba oil is relatively shelf-stable when compared with other vegetable oils. Unlike common vegetable oils, jojoba oil is chemically very similar to human sebum. Most jojoba oil is used as an ingredient in cosmetics and personal care products, especially skin care and hair care. Therapeutically it can aid in the healing process.

Sebum acts to protect and waterproof hair and skin, and keep them from becoming dry, brittle and cracked. It can also inhibit the growth of microorganisms on skin. It is thought that likewise, formulations with substances such as waxes that can mimic sebum for example like jojoba oil, stearic acid, isostearic acid, oleyl alcohol and the like including combinations thereof and especially in higher concentrations can provide protection to the hair and skin.

In one embodiment a foamable composition as described herein includes (a) at least about 10% by weight jojoba oil; (b) a stabilizer component comprising a surface-active agent, a polymeric agent or a mixture thereof; (c) water; and (d) a liquefied hydrocarbon gas propellant.

In one embodiment a foamable composition as described herein includes (a) at least about 10% by weight jojoba oil; (b) a stabilizer component comprising a surface-active agent, a polymeric agent or a mixture thereof; (c) water; and (d) a liquefied hydrocarbon gas propellant, in which the ratio of the component, the stabilizer and water to the gas propellant is about 100:3 by weight to about 100:35 by weight;

wherein the composition is substantially free from crystals and is substantially flowable; and in which, when the stabilizer component comprises a polymeric agent, the polymeric agent is present in the vehicle composition at a concentration of about 0.01% to about 5% by weight and includes a bioadhesive agent, a gelling agent, a film forming agent and a phase change agent; and wherein, upon release from a pressurized container, the foam produced is breakable.

In another embodiment the jojoba foamable composition further includes a solid wax. In an alternative embodiment the jojoba foamable composition includes another liquid wax. In a further embodiment the jojoba foamable composition includes another liquid wax and a solid wax In further embodiment the jojoba composition includes a liquid wax, wherein the concentration of the liquid wax and the jojoba oil together in the composition is at least about 20% by weight. In one or more further embodiments the concentration is at least about 25% by weight; 30% by weight; 35% by weight; or 40% by weight.

In a still further embodiment the jojoba composition comprises a liquid wax and a solid wax wherein the concentration of the liquid wax, the solid wax and the jojoba oil together in the composition is at least about 20% by weight. In one or more further embodiments the concentration is at least about 25% by weight; 30% by weight; 35% by weight; or 40% by weight.

In one or more embodiments, the fatty acid or alcohol is a biologically active. For example, benhenyl alcohol has some antiviral properties. In an embodiment, biologically active fatty acid or alcohol possesses keratolytic activities.

In an embodiment, the waxy substance is incorporated in the foamable composition in a safe and effective amount. The term "safe and effective" means an amount of an active agent that exerts a therapeutic effect on a specific disorder, without causing adverse effects that may prohibit the use of said active agent in the treatment of said disorder.

Although the presence of fatty acids and or fatty alcohol in the formulations may be high the formulations are substantially non irritating for one or more of the following reasons. By providing and applying the wax formulations in a low density foam preparation only relatively small amounts may be needed to cover a target surface when compared to a cream. Low levels of surfactants preferably non ionic are used. Non or low irritant waxes are selected that are safe and effective. By providing formulations in which the waxes and any active ingredients are dissolved the formulations are substantially free from crystals or particles which can irritate the skin.

In one or more embodiments, the wax, waxy substance, counterpart or derivative thereof contributes to the foam structure.

In one or more embodiments, the fatty acid is present in the composition in an ionized state.

In one or more embodiments, the ratio of wax to water is about 1:50; about 1:25; about 1:10; about 1:9; about 1:5; about 1:3; about 2:5; about 1:2; about; 3:5; about 2:3; about 1:1; about 3:2; about 5:3 about 2:1 about 3:1; about 4:1; about 5:1; about 9:1; or about 10:1.

The sensory properties of foams containing a waxy substance are favorable.

Foam Adjuvant

Optionally, the foamable vehicle further includes a foam adjuvant selected from the group consisting of a fatty alcohol having 15 or more carbons in their carbon chain; a fatty acid having 16 or more carbons in their carbon chain; fatty alcohols, derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid and a fatty acid substituted with a hydroxyl group and mixtures thereof and wherein the foam adjuvant is solid or waxy at room temperature or if a mixture at least one of the mixture is solid or waxy at room temperature.

In one or more embodiments the foam adjuvant is a wax, waxy substance, counterparts or derivative thereof.

Additional Organic Carrier

Optionally, the foamable vehicle further includes at least one additional organic carrier selected from the group consisting of a hydrophobic organic carrier, an emollient and mixtures thereof, at a concentration of about 2% to about 50% by weight. The hydrophobic solvent and/or the emollient can be selected from the group consisting of mineral oil, triglycerides, capric/caprylic triglyceride, alkyl esters of fatty acids such as isopropyl palmitate, isopropyl isostearate, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, maleated soybean oil, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; essential oils; and silicone oils, such as dimethicone, cyclomethicone, polyalkyl siloxane, polyaryl siloxane, polyalkylaryl siloxane, a polyether siloxane copolymer and a poly(dimethylsiloxane)-(diphenyl-siloxane) copolymer.

In an embodiment, the organic carrier is a polypropylene glycol alkyl ether (PPG alkyl ether). PPG alkyl ethers are liquid, water-insoluble propoxylated fatty alcohols, having the molecular formula of $RO(CH_2CHOCH_3)_n$; wherein "R" is a straight-chained or branched $C_4$ to $C_{22}$ alkyl group; and "n" is in the range between 4 and about 50. They are organic liquids that function as skin-conditioning agent in pharmaceutical and cosmetic formulations. Non-limiting exemplary PPG alkyl ethers include PPG stearyl ethers and PPG Butyl Ether. Preferred PPG alky ethers according to the present invention include PPG-15 Stearyl Ether, PPG-2 Butyl Ether, PPG-9-13 Butyl Ether and PPG-40 Butyl Ether.

In an embodiment, the organic carrier is a paraffin, glycerin or a petrolatum, which is also termed "white petrolatum" and "Vaseline". Preferably, one or more of paraffin, glycerin or petroleum used at between about 1% to about 5%.

Polymeric Agent

In some embodiments, the composition contains a polymeric agent selected from the group consisting of a bioadhesive agent, a gelling agent, a film forming agent and a phase change agent. A polymeric agent enhances the creation of foam having fine bubble structure, which does not readily collapse upon release from the pressurized aerosol can. The polymeric agent serves to stabilize the foam composition and to control drug residence in the target organ.

Exemplary polymeric agents include, in a non-limiting manner, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Additional exemplary polymeric agents include semi-synthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, and cationic celluloses, carbomer (homopolymer of acrylic acid is crosslinked with an allyl ether pentaerythritol, an allyl ether of sucrose, or an allyl ether of propylene, such as Carbopol® 934, Carbopol® 940, Carbopol® 941, Carbopol® 980 and Carbopol® 981, pemulen, klucel, and aluminum starch octenylsuccinate (ASOS) or other derivatized polymers. Polyethylene glycol, having molecular weight of 1000 or more (e.g., PEG 1,000, PEG 4,000, PEG 6,000 and PEG 10,000) also have gelling capacity and while they are considered herein as "secondary polar solvents", as detailed herein, they are also considered polymeric agents.

In one or more embodiments the polymeric agents have emulsifying properties. In certain preferred embodiments the polymeric agent is a derivatized hydrophilic polymer with hydrophobic alkyl moieties Other types that may also a similar stabilizing effect are silicone copolymers and derivatized starch aluminum starch octenyl succinate (ASOS).

In an embodiment the polymeric agent is a polymeric surfactant Poloxamer. Poloxamer is a synthetic block copolymer of ethylene oxide and propylene, having the general formula of:

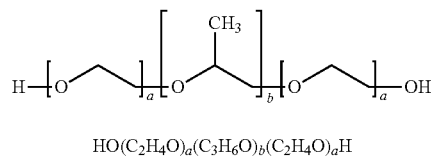

$HO(C_2H_4O)_a(C_3H_6O)_b(C_2H_4O)_aH$

For the generic term "Poloxamer", these copolymers are commonly named with the letter "P" (for Poloxamer) followed by three digits, the first two digits×100 give the approximate molecular mass of the polyoxypropylene core, and the last digit×10 gives the percentage polyoxyethylene content. For example, P407 is a Poloxamer with a polyoxypropylene molecular mass of 4,000 g/mol and a 70% polyoxyethylene content. A non limiting list is 124, 181, 182, 183, 184, 185, 188, 212, 215, 217, 231, 234, 235, 237, 238, 331, 333, 334, 3338, 335, 401, 402, 403 and 407.

Mixtures of the above polymeric agents are contemplated.

The concentration of the polymeric agent should be selected so that the composition, after filling into aerosol canisters, is flowable, and can be shaken in the canister. In one or more embodiments, the concentration of the polymeric agent is selected such that the viscosity of the composition, prior to filling of the composition into aerosol canisters, is about or less than 12,000 CPs, and more preferably, less than 10,000 CPs. Nevertheless where waxy substances are used in the composition especially in higher concentrations the viscosity may substantially exceed these figures.

In one or more embodiments the polymeric agent is a water miscible polymeric agent.

In one or more embodiments the polymeric agent is selected from at least one of the group consisting of pemulen, carboxymethyl cellulose (CMC), carbomer, klucel, hydroxyl propyl methyl cellulose and xantham gum.

Surface Active Agent

In some embodiments, the composition contains a surface-active agent. Surface-active agents (also termed "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). In many cases a single surfactant may suffice. In other cases a combination of two or more surfactants is desired. Reference to a surfactant in the specification can also apply to a combination of surfactants or a surfactant system. As will be appreciated by a person skilled in the art which surfactant or surfactant system is more appropriate is related to the vehicle and intended purpose. In general terms a combination of surfactants is usually preferable where the vehicle is an emulsion. In an emulsion environment a combination of surfactants can be significant in producing breakable forms of good quality. It has been further discovered that the generally thought considerations for HLB values for selecting a surfactant or surfactant combination are not always binding for emulsions and that good quality foams can be produced with a surfactant or surfactant combination both where the HLB values are in or towards the lipophilic side of the scale and where the HLB values are in or towards the hydrophilic side of the scale. Surfactants also play a role in foam formation where the foamable formulation is a single phase composition.

According to one or more embodiments the composition contains a single surface active agent having an HLB value between about 2 and 9, or more than one surface active agent and the weighted average of their HLB values is between about 2 and about 9. Lower HLB values may in certain embodiments be more applicable to water in oil emulsions.

According to one or more embodiments the composition contains a single surface active agent having an HLB value between about 7 and 14, or more than one surface active agent and the weighted average of their HLB values is between about 7 and about 14. Mid range HLB values may in certain embodiments be more suitable for oil in water emulsions.

According to one or more other embodiments the composition contains a single surface active agent having an HLB value between about 9 and about 19, or more than one surface active agent and the weighted average of their HLB values is between about 9 and about 19.

Preferably, the composition contains a non-ionic surfactant. Nonlimiting examples of possible non-ionic surfactants include a polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkyl ether, polyoxyethylene cetyl ether, polyoxyethylene palmityl ether, polyethylene oxide hexadecyl ether, polyethylene glycol cetyl ether, steareths such as steareth 2, brij 21, brij 721, brij 38, brij 52, brij 56 and brij W1, a sucrose ester, a partial ester of sorbitol and its anhydrides, sorbitan monolaurate, sorbitan monolaurate, a monoglyceride, a diglyceride, isoceteth-20 and mono-, di- and tri-esters of sucrose with fatty acids. In certain embodiments, suitable sucrose esters include those having high monoester content, which have higher HLB values. In an embodiment the alkyl or fatty acid polyoxyalkylene ether or ester respectively is not less than C14.

In certain embodiments with wax as emollient, surfactants are selected which can provide a close packed surfactant layer separating the oil and water phases. To achieve such objectives combinations of at least two surfactants are selected. Preferably, they should be complex emulgators and more preferably they should both be of a similar molecular type. For example, a pair of ethers, like steareth 2 and steareth 21, or a pair of esters, such as, PEG-40 stearate and polysorbate 80 may be used. In Certain circumstances POE esters cannot be used and a combination of sorbitan laurate and sorbitan stearate or a combination of sucrose stearic acid ester mixtures and sodium laurate may be used. All these combinations due to their versatility and strength may also be used satisfactorily and effectively with wax formulations, although the amounts and proportion may be varied according to the formulation and its objectives as will be appreciated by a man of the art.

It has been discovered also that by using a derivatized hydrophilic polymer with hydrophobic alkyl moieties as a polymeric emulsifier such as pemulen it is possible to stabilize the emulsion better about or at the region of phase reversal tension. Other types of derivatized polymers like silicone copolymers, derivatized starch [Aluminum Starch Octenylsuccinate (ASOS)]/[DRY-FLO AF Starch], and derivatized dexrin may also a similar stabilizing effect.

A series of dextrin derivative surfactants prepared by the reaction of the propylene glycol polyglucosides with a hydrophobic oxirane-containing material of the glycidyl ether are highly biodegradable. [Hong-Rong Wang and Keng-Ming Chen, Colloids and Surfaces A: Physicochemical and Engineering Aspects Volume 281, Issues 1-3, 15 Jun. 2006, Pages 190-193].

Non-limiting examples of non-ionic surfactants that have HLB of about 7 to about 12 include steareth 2 (HLB~4.9); glyceryl monostearate/PEG 100 stearate (Av HLB~11.2); stearate Laureth 4 (HLB~9.7) and cetomacrogol ether (e.g., polyethylene glycol 1000 monocetyl ether).

Non-limiting examples of preferred surfactants, which have a HLB of 4-19 are set out in the Table below:

| Surfactant | HLB |
| --- | --- |
| steareth 2 | ~4.9 |
| glyceryl monostearate/PEG 100 stearate | Av ~11.2 |
| Glyceryl Stearate | ~4 |
| Steareth-21 | ~15.5 |
| peg 40 stearate | ~16.9 |
| polysorbate 80 | ~15 |
| sorbitan stearate | ~4.7 |
| laureth 4 | ~9.7 |

| Surfactant | HLB |
| --- | --- |
| Sorbitan monooleate (span 80) | ~4.3 |
| ceteareth 20 | ~15.7 |
| steareth 20 | ~15.3 |
| ceteth 20 | ~15.7 |
| Macrogol Cetostearyl Ether | ~15.7 |
| ceteth 2 (Lipocol C-2) | ~5.3 |
| PEG-30 Dipolyhydroxystearate | ~5.5 |
| sucrose distearate (Sisterna SP30) | ~6 |
| polyoxyethylene (100) stearate | ~18.8 |

More exemplary stabilizing surfactants which may be suitable for use in the present invention are found below.

PEG-Fatty Acid Monoester Surfactants

| Chemical name | Product example name | HLB |
| --- | --- | --- |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-45 stearate | Nikkol MYS-45 (Nikko) | 18 |
| PEG-50 stearate | Myrj 53 | >10 |
| PEG-100 stearate | Myrj 59, Arlacel 165 (ICI) | 19 |

PEG-Fatty Acid Diester Surfactants:

| Chemical name | Product example name | HLB |
| --- | --- | --- |
| PEG-4 dilaurate | Mapeg .RTM. 200 DL (PPG), Kessco .RTM.PEG 200 DL (Stepan), LIPOPEG 2-DL (Lipo Chem.) | 7 |
| PEG-4 | distearate Kessco .RTM. 200 DS (Stepan.sub.) | 5 |
| PEG-32 dioleate | Kessco .RTM. PEG 1540 DO (Stepan) | 15 |
| PEG-400 dioleate | Cithrol 4DO series (Croda) | >10 |
| PEG-400 disterate | Cithrol 4DS series (Croda) | >10 |
| PEG-20 glyceryl oleate | Tagat .RTM. O (Goldschmidt) | >10 |

Transesterification Products of Oils and Alcohols

| Chemical name | Product example name | HLB |
| --- | --- | --- |
| PEG-30 castor oil | Emalex C-30 (Nihon Emulsion) | 11 |
| PEG-40 hydrogenated castor oil | Cremophor RH 40 (BASF), Croduret (Croda), Emulgin HRE 40 (Henkel) | 13 |

Polyglycerized Fatty Acids, Such as:

| Chemical name | Product example name | LB |
| --- | --- | --- |
| Polyglyceryl-6 dioleate | Caprol .RTM. 6G20 (ABITEC); PGO-62 (Calgene), PLUROL OLEIQUE CC 497 (Gattefosse)Hodag | 8.5 |

PEG-Sorbitan Fatty Acid Esters

| Chemical name | Product example name | HLB |
| --- | --- | --- |
| PEG-20 sorbitan monolaurate | Tween-20 (Atlas/ICI), Crillet 1 (Croda), DACOL MLS 20 (Condea) | 17 |
| PEG-20 sorbitan Monopalmitate | Tween 40 (Atlas/ICI), Crillet 2 (Croda) | 16 |
| PEG-20 sorbitan monostearate | Tween-60 (Atlas/ICI), Crillet 3 (Croda) | 15 |
| PEG-20 sorbitan monooleate | Tween-80 (Atlas/ICI), Crillet 4 (Croda) | 15 |

Polyethylene Glycol Alkyl Ethers

| Chemical name | Product example name | HLB |
| --- | --- | --- |
| PEG-2 oleyl ether | oleth-2 Brij 92/93 (Atlas/ICI) | 4.9 |
| PEG-3 oleyl ether | oleth-3 Volpo 3 (Croda) | <10 |
| PEG-5 oleyl ether | oleth-5 Volpo 5 (Croda) | <10 |
| PEG-10 oleyl ether | oleth-10 Volpo 10 (Croda), Brij 96/97 (Atlas/ICI) | 12 |
| PEG-20 oleyl ether | oleth-20 Volpo 20 (Croda), Brij 98/99 (Atlas/ICI) | 15 |
| PEG-4 lauryl ether | laureth-4Brij 30 (Atlas/ICI) | 9.7 |
| PEG-23 lauryl ether | laureth-23Brij 35 (Atlas/ICI) | 17 |
| PEG-10 stearyl ether | Brij 76 (ICI) | 12 |
| PEG-2 cetyl ether | Brij 52 (ICI) | 5.3 |

Sugar Ester Surfactants

| Chemical name | Product example name | HLB |
| --- | --- | --- |
| Sucrose distearate | Sisterna SP50, Surfope 1811 | 11 |

Sorbitan Fatty Acid Ester Surfactants

| Chemical name | Product example name | HLB |
| --- | --- | --- |
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |

In one or more embodiments the surface active agent is a combination of two or more surface active agents that can be more effective than a single surfactant and provides a more stable emulsion or improved foam quality than a single surfactant. For example and by way of non-limiting explanation it has been found that by choosing say two surfactants, one hydrophobic and the other hydrophilic the combination can produce a more stable emulsion than a single surfactant. Preferably, the complex emulgator comprises a combination of surfactants wherein there is a difference of about 4 or more units between the HLB values of the two surfactants or there is a significant difference in the chemical nature or structure of the two or more surfactants. Without being bound by any theory by appropriate selection of a liquid wax and or a solid wax to use with a surfactant pair (and vice versa) the packing of the surfactant layer or interphase can be effected and may result in a less packed and more disrupted layer or interphase by choosing a branched and or unsaturated wax or a more packed less disrupted layer or interphase by selecting straight chain saturated waxes. Nevertheless, an appropriate single surfactant with a liquid wax or a solid wax or mixtures thereof can also have a similar effect on the surfactant layer or interphase.

Specific non limiting examples of surfactant systems are, combinations of polyoxyethylene alkyl ethers, such as Brij 59/Brij 10; Brij 52/Brij 10; Steareth 2/Steareth 20; Steareth 2/Steareth 21 (Brij 72/Brij 721); combinations of polyoxyethylene stearates such as Myrj 52/Myrj 59; combinations of sucrose esters, such as Surphope 1816/Surphope 1807; combinations of sorbitan esters, such as Span 20/Span 80; Span 20/Span 60; combinations of sucrose esters and sorbitan esters, such as Surphope 1811 and Span 60; combinations of liquid polysorbate detergents and PEG compounds, such as Tween 80/PEG-40 stearate; methyl glucaso sequistearate; polymeric emulsifiers, such as Permulen (TRI or TR2); liquid crystal systems, such as Arlatone (2121), Stepan (Mild RM1), Nikomulese (41) and Montanov (68) and the like.

In certain embodiments the surfactant is preferably one or more of the following: a combination of steareth-2 and steareth-21 on their own or in combination with glyceryl monostearate (GMS); in certain other embodiments the surfactant is a combination of polysorbate 80 and PEG-40 stearate. In certain other embodiments the surfactant is a combination of glyceryl monostearate/PEG 100 stearate. In certain other embodiments the surfactant is a combination of two or more of stearate 21, PEG 40 stearate, and polysorbate 80. In certain other embodiments the surfactant is a combination of two or more of laureth 4, span80, and polysorbate 80. In certain other embodiments the surfactant is a combination of two or more of GMS and ceteareth. In certain other embodiments the surfactant is a combination of two or more of steareth 21, ceteareth 20, ceteth 2 and laureth 4 In certain other embodiments the surfactant is a combination of ceteareth 20 and polysorbate 40 stearate. In certain other embodiments the surfactant is a combination of span 60 and GMS. In certain other embodiments the surfactant is a combination of two or all of PEG 40 stearate, sorbitan stearate and polysorbate 60

In certain other embodiments the surfactant is one or more of sucrose stearic acid esters, sorbitan laureth, and sorbitan stearate.

Without being bound by any particular theory or mode of operation, it is believed that the use of non-ionic surfactants with significant hydrophobic and hydrophilic components, increase the emulsifier or foam stabilization characteristics of the composition. Similarly, without being bound by any particular theory or mode of operation, using combinations of surfactants with high and low HLB's to provide a relatively close packed surfactant layer may strengthen the emulsion.

In one or more embodiments the stability of the composition can be improved when a combination of at least one non-ionic surfactant having HLB of less than 9 and at least one non-ionic surfactant having HLB of equal or more than 9 is employed. The ratio between the at least one non-ionic surfactant having HLB of less than 9 and the at least one non-ionic surfactant having HLB of equal or more than 9, is between 1:8 and 8:1, or at a ratio of 4:1 to 1:4. The resultant HLB of such a blend of at least two emulsifiers is preferably between about 9 and about 14.

Thus, in an exemplary embodiment, a combination of at least one non-ionic surfactant having HLB of less than 9 and at least one non-ionic surfactant having HLB of equal or more than 9 is employed, at a ratio of between 1:8 and 8:1, or at a ratio of 4:1 to 1:4, wherein the HLB of the combination of emulsifiers is preferably between about 5 and about 18.

In certain cases, the surface active agent is selected from the group of cationic, zwitterionic, amphoteric and ampholytic surfactants, such as sodium methyl cocoyl taurate, sodium methyl oleoyl taurate, sodium lauryl sulfate, triethanolamine lauryl sulfate and betaines.

Many amphiphilic molecules can show lyotropic liquid-crystalline phase sequences depending on the volume balances between the hydrophilic part and hydrophobic part. These structures are formed through the micro-phase segregation of two incompatible components on a nanometer scale. Soap is an everyday example of a lyotropic liquid crystal. Certain types of surfactants tend to form lyotropic liquid crystals in emulsions interface (oil-in-water) and exert a stabilizing effect In one or more embodiments the surfactant is a surfactant or surfactant combination is capable of or which tends to form liquid crystals. Surfactants which tend to form liquid crystals may improve the quality of foams. Non limiting examples of surfactants with postulated tendency to form interfacial liquid crystals are: phospholipids, alkyl glucosides, sucrose esters, sorbitan esters.

In one or more embodiments the at least one surface active agent is liquid.

In one or more embodiments the liquid surfactant is a polysorbate, preferably polysorbate 80 or 60.

In one or more embodiments the at least one surface active agent is solid, semi solid or waxy.

In one or more embodiments the surfactant can be, a surfactant system comprising of a surfactant and a co surfactant, a waxy emulsifier, a liquid crystal emulsifier, an emulsifier which is solid or semi solid at room temperature and pressure, or combinations of two or more agents in an appropriate proportion as will be appreciated a person skilled in the art. Where a solid or semi solid emulsifier combination is used it can also comprise a solid or semi solid emulsifier and a liquid emulsifier.

In one or more embodiments, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. Non-ionic surfactants alone can provide formulations and foams of good or excellent quality in the carriers and compositions.

Thus, in some embodiments, the composition contains a non-ionic surfactant. In other embodiments the composition includes a mixture of non-ionic surfactants as the sole surface active agent. Yet, in additional embodiments, the foamable composition includes a mixture of at least one non-ionic surfactant and at least one ionic surfactant in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1. In further embodiments, surface active agent comprises a combination of a non-ionic surfactant and an ionic surfactant, at a ratio of between 1:1 and 20:1.

In one or more embodiments, a combination of a non-ionic surfactant and an ionic surfactant (such as sodium lauryl sulphate and cocamidopropylbetaine) is employed, at a ratio of between 1:1 and 20:1, or at a ratio of 4:1 to 10:1; for example, about 1:1, about 4:1, about 8:1, about 12:1, about 16:1 and about 20:1 or at a ratio of 4:1 to 10:1, for example, about 4:1, about 6:1, about 8:1 and about 10:1.

In selecting a suitable surfactant or combination thereof it should be borne in mind that the upper amount of surfactant that may be used may be limited by the shakability of the composition. If the surfactant is non liquid, it can make the formulation to viscous or solid. This can be particularly significant if the formulation has high molecular weight, e.g., a high molecular weight PEG or polymeric agents or petroleum or if the surfactants are large. Solvents and polymeric agents which have high molecular weight and are very viscous or solid or waxy (e.g., Peg 1500, 2000, etc. or petrolatum) can exacerbate the effect of a waxy or solid surfactant on shakability or flowability. In general terms, as the amount of non-liquid surfactant is increased the shakability of the formulation reduces until a limitation point is reached where the formulation becomes non shakable and unsuitable. Thus in one embodiment, an effective amount of surfactant may be used provided the formulation remains shakable. In other certain exceptional embodiments the upper limit may be determined by flowability such as in circumstances where the composition is marginally or apparently non-shakable. The formulation is sufficiently flowable to be able to flow through an actuator valve and be released and still expand to form a good quality foam.

In certain embodiments the amount of surfactant or combination of surfactants may be between about 0.05% to less than about 20%; between about 0.05% to about 15%. or between about 0.05% to about 10%. Although these higher amounts of surfactants may be used nevertheless the amount of surfactants should be reduced or kept low to avoid potential irritation; depletion of fatty substances from the skin; and dry skin from repeated use of the formulations. Thus in some embodiments the concentration of surface active agent is lower, e.g., between about 0.2% and about 8%. In a further embodiment the concentration of surface active agent is between about 1% and about 5%. By selecting hydrophobic waxes which can also function as a foam adjuvant in the formulation or as a co surfactant giving support to the surfactant in stabilizing the emulsion and or in producing better foam it is possible to use a smaller amount of surfactant. In a preferred embodiment the hydrophobic waxes are a mixture of a liquid and a solid hydrophobic wax at least one of which can function as a foam adjuvant. In a more preferred embodiment the formulation comprises a liquid and a solid wax both of which can also function as a foam adjuvant.

High levels of surfactants which can form a mesomorphic phase should be avoided. Thus, in an embodiment the amount of surfactant or combination of surfactants is less than that needed to form a mesomorphic phase.

In some embodiments, it is desirable that the surface active agent does not contain a polyoxyethylene (POE) moiety, such as polysorbate surfactants, POE fatty acid esters, and POE alkyl ethers, because the active agent is incompatible with such surface active agents. For example, the active agent pimecrolimus is not stable the presence of POE moieties, yet benefits greatly from the use of dicarboxylic esters as penetration enhancers. In such cases, alternative surface active agents are employed. In an exemplary manner, POE—free surfactants include non-ethoxylated sorbitan esters, such as sorbitan monopalmitate, sorbitan monostearate, sorbitan tristearate, sorbitan monooleate, sorbitan trioleate, sorbitan monolaurate and sorbitan sesquioleate; glycerol fatty acid esters, such as glycerol monostearate and glycerol monooleate; mono-, di- and tri-esters of sucrose with fatty acids (sucrose esters), sucrose stearate, sucrose distearate sucrose palmitate and sucrose laurate; and alkyl polyglycosides, such as lauryl diglucoside. In an embodiment the surfactant is not a polyoxyethylene fatty acid ester. In an embodiment the surfactant is not a polyoxyethylene alkyl ether. In an embodiment the surfactant is not a polyoxyethylene lauryl ether.

If the composition as formulated is a substantially non shakable composition it is nevertheless possible as an exception in the scope for the formulation to be flowable to a sufficient degree to be able to flow through an actuator valve and be released and still expand to form a good quality foam. This surprising and unusual exception may be due one or more of a number of factors such as the high viscosity, the softness, the lack of crystals, the pseudoplastic or semi pseudo plastic nature of the composition and the dissolution of the propellant into the composition.

In one or more embodiments, the surface-active agent includes mono-, di- and tri-esters of sucrose with fatty acids (sucrose esters), prepared from sucrose and esters of fatty acids or by extraction from sucro-glycerides. Suitable sucrose esters include those having high monoester content, which have higher HLB values.

Phase Inversion and Tension

Phase inversion is a factor in the preparation and stabilization of emulsions and can be both an aid and a detriment. Phase inversion involves the change of emulsion type from o/w to w/o or vice versa. Prior to phase inversion occurring there is a tension in the emulsion which if destabilized or driven will lead to phase inversion and if controlled or ameliorated or dissipated will result in a more stable emulsion. The occurrence of phase inversion during preparation can be a sign of instability. If controlled, it can result in a finer product but if due to other factors after the emulsion was prepared it can cause problems. Inversion can occur by for example adding calcium chloride to an o/w emulsion stabilized with sodium stearate to form calcium stearate. Inversion can also occur as the product of changes to the phase-volume ratio. For example if a small amount of water is added to surfactant mixed with oil and agitated a w/o emulsion is formed. As the amount of water added is gradually increased a point will be reached where the water and emulsifier envelop the oil as small droplets to form an o/w emulsion. The amount of each ingredient including the surfactants will have their part to play in the phenomenon.

Substantially Alcohol-Free

According to one or more embodiments, the foamable composition is substantially alcohol-free, i.e., free of short chain alcohols. Short chain alcohols, having up to 5 carbon atoms in their carbon chain skeleton and one hydroxyl group, such as ethanol, propanol, isopropanol, butaneol, iso-butaneol, t-butaneol and pentanol, are considered less desirable solvents or polar solvents due to their skin-irritating effect. Thus, the composition is substantially alcohol-free and includes less than about 5% final concentration of lower alcohols, preferably less than about 2%, more preferably less than about 1%.

Substantially Non Aqueous

In certain cases, the active agent degrades in the presence of water, and therefore, in such cases the present of water in the composition is not desirable. Thus, in certain preferred embodiments, the composition is substantially non-aqueous. The term "substantially non-aqueous" or "substantially waterless" is intended to indicate that the composition has a water content below about 25%.

Shakability

'Shakability' means that the composition contains some or sufficient flow to allow the composition to be mixed or remixed on shaking. That is, it has fluid or semi fluid properties. In some very limited cases it may exceptionally be possible to have a foamable composition which is flowable but not apparently shakable.

Breakability

A breakable foam is one that is thermally stable, yet breaks under sheer force.

The breakable foam is not "quick breaking", i.e., it does not readily collapse upon exposure to body temperature environment. Sheer-force breakability of the foam is clearly advantageous over thermally induced breakability, since it allows comfortable application and well directed administration to the target area.

Modulating Agent

The term modulating agent is used to describe an agent which can improve the stability of or stabilize a foamable carrier or composition and or an active agent by modulating the effect of a substance or residue present in the carrier or composition.

In one or more embodiments the modulating agent is used in a water in oil or oil in water emulsion In certain embodiments the substance or residue may for example be acidic or basic and potentially alter pH in an emulsion environment or it may be one or more metal ions which may act as a potential catalyst in an emulsion environment.

In one or more embodiments the modulating agent is used to describe an agent which can affect pH in an aqueous solution. The agent can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound.

In one or more further embodiments the modulating agent is used to describe an agent, which is a chelating or sequestering or complexing agent that is sufficiently soluble or functional in the solvent to enable it to "mop up" or "lock" metal ions.

In an embodiment modulating agent is used to describe an agent which can effect pH in an aqueous solution the term modulating agent more particularly means an acid or base or buffer system or combinations thereof, which is introduced into or is present in and acts to modulate the ionic or polar characteristics and any acidity or basesity balance of an emulsion carrier, composition, foamable carrier or foamable composition or resultant foam.

In one or more embodiments the composition does not contain a modulating agent. In other embodiments the composition does not contain a neutralizing agent. In further embodiments the composition is not partially neutralized.

In one or more embodiments the modulating agent comprises an organic compound.

In one or more embodiments the modulating agent is used to acidify the formulation. In one embodiment it is used to provide an acidic pH, which is similar to or within the pH range found in healthy skin or in a healthy body cavity.

In an embodiment the vehicles and foam formulations are further acidified with an organic acid, preferably a liquid organic acid, more preferably an alpha hydroxy acid.

In one or more embodiments the chelating agent is selected from the group consisting of ethylenediaminetetraacetic acid (EDTA), diethylenetriaminepentaacetic acid (DTPA), hydroxyethylenediaminetriacetic acid (HEDTA), nitrilotriacetic acid (NTA), O,O'-bis(2-aminoethyl)ethyleneglycol-N,N,N',N'-tetraacetic acid (EGTA), trans-1,2-diaminocyclohexane-N,N,N',N'-tetraacetic acid (CyDTA) or a pharmaceutically acceptable salt thereof (normally as a sodium salt), more preferably EDTA, HEDTA and their salts; most preferably EDTA and its salts.

In one or more embodiments a non limiting example of the chelating agent is EDTA. Typically, the chelating and sequestering agent is present in the composition at a level of up to about 5.0%, preferably 1.0 percent, by weight, of the composition.

In one or more embodiments the modulating agent may also be a preservative or an antioxidant or an ionization agent. Any preservative, antioxidant or ionization agents suitable for pharmaceutical or cosmetic application may be used. Non limiting examples of antioxidants are tocopherol succinate, propyl galate, butylated hydroxy toluene and butyl hydroxy anisol. Ionization agents may be positive or may be negative depending on the environment and the active agent or composition that is to be protected. Ionization agents may for example act to protect or reduce sensitivity of active agents. Non limiting examples of positive ionization agents are benzyl conium chloride, and cetyl pyridium chloride. Non limiting examples of negative ionization agents are sodium lauryl sulphate, sodium lauryl lactylate and phospholipids.

Humectant

A humectant is a substance that helps retain moisture and also prevents rapid evaporation. Non limiting examples are propylene glycol, propylene glycol derivatives, glycerin, hydrogenated starch hydrosylate, hydrogenated lanolin, lanolin wax, D mannitol, sorbitol, sodium 2-pyrrolidone-5-carboxylate, sodium lactate, sodium PCA, soluble collagen, dibutyl phthalate, and gelatin. Other examples may be found in the Handbook of Pharmaceutical Additives published by Gower.

Moisturizers

A moisturizer, is a substance that helps retain moisture or add back moisture to the skin. Examples include, without limitation, allantoin, petrolatum, urea, lactic acid, sodium PCV, glycerin, shea butter, caprylic/capric/stearic triglyceride, candelilla wax, propylene glycol, lanolin, hydrogenated oils, squalene, sodium hyaluronate and lysine PCA. Other examples may be found in the *Handbook of Pharmaceutical Additives* published by Gower.

Pharmaceutical compositions may in one or more embodiments usefully comprise in addition a humectant or a moisturizer or combinations thereof.

Polar Solvent

Optionally, the foamable vehicle further includes at least one polar solvent.

A "polar solvent" is an organic solvent, typically soluble in both water and oil. Certain polar solvents, for example propylene glycol and glycerin, possess the beneficial property of a humectant.

In one or more embodiments, the polar solvent is a humectant.

In one or more embodiments, the polar solvent is a polyol. Polyols are organic substances that contain at least two hydroxy groups in their molecular structure.

In one or more embodiments, the polar solvent contains an diol (a compound that contains two hydroxy groups in its molecular structure), such as propylene glycol (e.g., 1,2-propylene glycol and 1,3-propylene glycol), butanediol (e.g., 1,4-butaneediol), butanediol (e.g., 1,3-butaneediol and 1,4-butenediol), butynediol, pentanediol (e.g., 1,5-pentanediol), hexanediol (e.g., 1,6-hexanediol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the polar solvent contains a triol (a compound that contains three hydroxy groups in its molecular structure), such as glycerin and 1,2,6-Hexanetriol.

Other non-limiting examples of polar solvents include pyrrolidones, (such as N-methyl-2-pyrrolidone and 1-methyl-2-pyrrolidinone), dimethyl isosorbide, 1,2,6-hexapetriol, dimethyl sulfoxide (DMSO), ethyl proxitol, dimethylacetamide (DMAc) and alpha hydroxy acids, such as lactic acid and glycolic acid.

According to still other embodiments, the polar solvent is a polyethylene glycol (PEG) or PEG derivative that is liquid at ambient temperature, including PEG200 (MW (molecular weight) about 190-210 kD), PEG300 (MW about 285-315 kD), PEG400 (MW about 380-420 kD), PEG600 (MW about 570-630 kD) and higher MW PEGs such as PEG 4000, PEG 6000 and PEG 10000 and mixtures thereof.

Polar solvents are known to enhance the penetration of active agent into the skin and through the skin, and therefore, their inclusion in the composition can be desirable, despite their undesirable skin drying and irritation potential. There is at one level a commonality between the different polar solvents and their penetration enhancement properties. Lower molecular weight alcohols can sometimes be more potent as a solvent, for example by extracting lipids from the skin layers more effectively, which characteristic can adversely affect the skin structure and cause dryness and irritation. Therefore the selection of lower molecular weight alcohols is ideally avoided.

Polar solvents, such as detailed below possess high solubilizing capacity and contribute to the skin penetration of an active agent. Non limiting examples include dimethyl isosorbide polyols, such as glycerol (glycerin), propylene glycol, hexylene glycol, diethylene glycol, propylene glycol n-alkanols, terpenes, di-terpenes, tri-terpenes, limonene, terpene-ol, 1-menthol, dioxolane, ethylene glycol, other glycols, oleyl alcohol, alpha-hydroxy acids, such as lactic acid and glycolic acid, sulfoxides, such as dimethylsulfoxide (DMSO), dimethylformanide, methyl dodecyl sulfoxide, dimethylacetamide, azone (1-dodecylazacycloheptan-2-one), 2-(n-nonyl)-1,3-dioxolane, alkanols, such as dialkylamino acetates, and admixtures thereof. In certain preferred embodiments, the polar solvent is selected from the group consisting of dimethyl isosorbide glycerol (glycerin), propylene glycol, hexylene glycol, terpene-ol, oleyl alcohol, lactic acid and glycolic acid.

Skin Penetration Enhancer

In some embodiments, the compositions described herein include one or more skin penetration enhancers. A "skin penetration enhancer", also termed herein "penetration enhancer," is an organic solvent, typically soluble in both water and oil. Examples of penetration enhancer include polyols, such as glycerol (glycerin), propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, hexylene glycol, other glycols, sulfoxides, such as dimethylsulfoxide (DMSO), dimethylformanide, methyl dodecyl sulfoxide, dimethylacetamide, dimethylisosorbide, monooleate of ethoxylated glycerides (with 8 to 10 ethylene oxide units), azone (1-dodecylazacycloheptan-2-one), 2-(n-nonyl)-1,3-dioxolane, esters, such as isopropyl myristate/palmitate, ethyl acetate, butyl acetate, methyl proprionate, capric/caprylic triglycerides, octylmyristate, dodecyl-myristate; myristyl alcohol, lauryl alcohol, lauric acid, lauryl lactate ketones; amides, such as acetamide oleates such as triolein; various alkanoic acids such as caprylic acid; lactam compounds, such as azone; alkanols, such as dialkylamino acetates, and admixtures thereof.

According to one or more embodiments, the penetration enhancer is a polyethylene glycol (PEG) or PEG derivative that is liquid at ambient temperature Potent Solvent In one or more embodiments, the foamable composition includes a potent solvent, in addition to or in place of one of the hydrophobic solvents, polar solvents or emollients of the composition. A potent solvent is a solvent other than mineral oil that solubilizes a specific active agent substantially better than a hydrocarbon solvent such as mineral oil or petrolatum. For example, a potent solvent solubilizes the active agent 5 fold better than a hydrocarbon solvent; or even solubilizes the active agent 10-fold better than a hydrocarbon solvent.

In one or more embodiments, the composition includes at least one active agent in a therapeutically effective concentration; and at least one potent solvent in a sufficient amount to substantially solubilize the at least one active agent in the composition. The term "substantially soluble" means that at least 95% of the active agent has been solubilized, i.e., 5% or less of the active agent is present in a solid state. In one or more embodiments, the concentration of the at least one potent solvent is more than about 40% of the at least one solvent of the composition; or even more than about 60%.

Non-limiting examples of pairs of active agent and potent solvent include: Betamethasone valerate: Practically insoluble in mineral oil (<0.01%); soluble more than 1% in glycofurol; Hydrocortisone butyrate: Practically insoluble in mineral oil (<0.01%); soluble more than 1% in glycofurol; Metronidazole: Practically insoluble in mineral oil (<0.01%); soluble more than 1% in dimethyl isosorbide; Ketoconazole: Practically insoluble in mineral oil (<0.01%); soluble more than 1% in glycofurol, propylene glycol and dimethyl isosorbide; Mupirocin: Practically insoluble in mineral oil (<0.01%); soluble more than 1% in glycofurol, hexylene glycol, dimethyl isosorbide, propylene glycol and polyethylene glycol 400 (PEG 400); Meloxicam, a non-steroidal anti-inflammatory agent: Practically insoluble in mineral oil (<0.001%); soluble in propylene glycol: 0.3 mg/mL; and in PEG 400: 3.7 mg/mL; and Progesterone: Practically insoluble in mineral oil (<0.001%); soluble in PEG 400: 15.3 mg/mL.

A non-limiting exemplary list of solvents that can be considered as potent solvents includes polyethylene glycol, propylene glycol, hexylene glycol, butanediols and isomers thereof, glycerol, benzyl alcohol, DMSO, ethyl oleate, ethyl caprylate, diisopropyl adipate, dimethylacetamide, N-methylpyrrolidone, N-hydroxyethylpyrrolidone, polyvinylpyrrolidone, isosorbide derivatives, such as dimethyl isosorbide, glycofurol and ethoxydiglycol (transcutol) and laurocapram.

The use of a potent solvent in a foam composition provides an improved method of delivering poorly soluble therapeutic agents to a target area. It is known that low drug solubility results in poor bioavailability, leading to decreased effectiveness of treatment. Foam compositions, for which the solvent includes a potent solvent, increase the levels of the active agent in solution and thus, provide high delivery and improved therapy.

Potent solvents, as defined herein, are usually liquid. Formulations comprising potent solvents and active agents are generally disadvantageous as therapeutics, since their usage involves unwanted dripping and inconvenient method of application; resulting in inadequate dosing. Surprisingly, the foams, which are drip-free, provide a superior vehicle for such active agents, enabling convenient usage and accurate effective dosing.

In one or more embodiments the present invention the foamable pharmaceutical composition may additionally include a mixture of two or more of the solvents selected from the group of hydrophobic solvents, silicone oils, emollients, polar solvents and potent solvents in an appropriate proportion as would be appreciated to a person skilled in the art.

In one or more embodiments, the PPG alkyl ether may act as a potent solvent

Additional Components

In an embodiment, a composition includes one or more additional components. Such additional components include but are not limited to anti perspirants, anti-static agents, buffering agents, bulking agents, chelating agents, cleansers, colorants, conditioners, deodorants, diluents, dyes, emollients, fragrances, hair conditioners, humectants, pearlescent aids, perfuming agents, permeation enhancers, pH-adjusting agents, preservatives, protectants, skin penetration enhancers, softeners, solubilizers, sunscreens, sun blocking agents, sunless tanning agents, viscosity modifiers and vitamins. As is known to one skilled in the art, in some instances a specific additional component may have more than one activity, function or effect.

Propellants

Suitable propellants include volatile hydrocarbons such as butane, propane, isobutane and fluorocarbon gases, or mixtures thereof.

In an embodiment the propellant is AP 70 which is a mixture of propane, isobutene and butane.

The propellant makes up about 5-25 wt % of the foamable composition (i.e., the ratio of the propellant to components that make up the foamable vehicle range from about 5:100 to about 25:100). In some circumstances the propellant may be up to about 35% or as low as about 3% (i.e., the ratio of the propellant to components that make up the foamable vehicle is from about 3:100 to about 35:100). The propellants are used to generate and administer the foamable composition as a foam. The total composition including propellant, foamable compositions and optional ingredients is referred to as the foamable composition.

Alcohol and organic solvents render foams inflammable. It has been surprisingly discovered that fluorohydrocarbon propellants, other than chloro-fluoro carbons (CMOs), which are non-ozone-depleting propellants, are particularly useful in the production of a non-flammable foamable composition. A test according to European Standard prEN 14851, titled "Aerosol containers—Aerosol foam flammability test" revealed that compositions containing an organic carrier that contains a hydrophobic organic carrier and/or a polar solvent, which are detected as inflammable when a hydrocarbon propellant is used, become non-flammable, while the propellant is an HFC propellant.

Such propellants include, but are not limited to, hydrofluorocarbon (HFC) propellants, which contain no chlorine atoms, and as such, fall completely outside concerns about stratospheric ozone destruction by chlorofluorocarbons or other chlorinated hydrocarbons. Exemplary non-flammable propellants according to this aspect of the invention include propellants made by DuPont under the registered trademark Dymel, such as 1,1,1,2 tetrafluoroethane (Dymel 134), and 1,1,1,2,3,3,3 heptafluoropropane (Dymel 227). HFCs possess Ozone Depletion Potential of 0.00 and thus, they are allowed for use as propellant in aerosol products.

Notably, the stability of foamable emulsions including HFC as the propellant can be improved in comparison with the same composition made with a hydrocarbon propellant.

In one or more embodiments foamable compositions comprise a combination of a HFC and a hydrocarbon propellant such as n-butane or mixtures of hydrocarbom propellants such as propane, isobutane and butane. In one or more embodiments the hydrocarbon mixture of propane, isobutane and butane is AP70.

In one or more embodiments the foamable compositions are not self foaming.

Microemulsions and Nanoemulsions

In some embodiments, the compositions described herein are microemulsions or nanoemulsions. Microemulsions and nanoemulsion are monophasic, transparent (or slightly translucent) dispersions of oil and water. Unlike conventional emulsions, microemulsions and nanoemulsion are thermodynamically stable, making them a favorable vehicle for pharmaceutical compositions, which have to maintain stability for long periods of time. They and a method of manufacture are more particularly described in US2006/0233721 which is incorporated herein by way of reference. As will be appreciated by a person of skill in the art the methodology may be adapted according to the type of carrier composition.

Aging

In order to project the potential shelf life and stability of the compositions and their ingredients particularly active or benefit agents the compositions can subjected to a number of tests, including centrifugation to look for resistance to creaming, phase separation; one or more freeze thaw cycles, standing at room and higher temperatures as an indicator of resistance to aging.

Composition and Foam Physical Characteristics and Advantages

A pharmaceutical or cosmetic composition manufactured using the foamable carrier is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable composition is stable, having an acceptable shelf-life of at least one year, or preferably, at least two years at ambient temperature, as revealed in accelerated stability tests. The foamable compositions according to the present invention are stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

As further aspect of the foam is breakability. The breakable foam is thermally stable, yet breaks under sheer force. Sheer-force breakability of the foam is clearly advantageous over thermally induced breakability. Thermally sensitive foams immediately collapse upon exposure to skin temperature and, therefore, cannot be applied on the hand and afterwards delivered to the afflicted area.

Another property of the foam is specific gravity, as measured upon release from the aerosol can. Typically, foams have specific gravity of less than 0.12 g/mL; or less than 0.10 g/mL; or less than 0.08 g/mL, depending on their composition and on the propellant concentration.

Pharmaceutical Composition

The foamable carrier is an ideal vehicle for active pharmaceutical ingredients and active cosmetic ingredients. In the context, active pharmaceutical ingredients and active cosmetic ingredients are collectively termed "active agent" or "active agents." The active agents can be used in the formulation as a suspended solid or in solution, alone or in combination with other active agents.

In one or more embodiments the active ingredient is an immune response modifier or antiviral agent selected from the group consisting of imiquimod, resiquimod, and gardiquimod.

Imiquimod (4-Amino-1-isobutyl-1H-imidazo[4,5-c]quinoline) an imidazoquinoline amine, is an immune response modifier used topically in the treatment of external genital and perianal warts, superficial basal cell carcinomas, and actinic keratoses. It is applied as a 5% cream, with the frequency and period varying depending on the disease. Imiquimod is under investigation for the treatment of Bowen's disease and of other squamous cell carcinomas. Adverse effects after topical application of imiquimod include local skin erosion, erythema, excoriation, flaking, and oedema. There have been reports of localised hypopigmentation and hyperpigmentation. Skin reactions away from the site of application have been reported. Imiquimod is used topically for the treatment of external genital and perianal exophytic warts (condylomata acuminata) caused by human papillomavirus (HPV). Potentially it may have application for treating body cavity warts urethral, intravaginal, cervical, rectal, intra-anal, or oral HPV warts. Imiquimod has been used topically for the treatment of molluscum contagiosum and for the treatment of actinic keratoses. It may also have potential for the topical treatment of verruca vulgaris (common warts). Alternative regimens include intralesional interferon alfa and laser surgery. There is some evidence that warts located on moist surfaces and/or in intertriginous areas appear to respond better to topical treatments. On this basis in one or more embodiments, the imiquimod formulation further comprises a moisturizer and or a humectant.

Other members of the imiquimod family are resiquimod (used against herpes simplex virus infections, including genital herpes and is a potential treatment of various other diseases, including other viral infections and eczema and as a vaccine adjuvant) and gardiquimod (a potential antiviral).

In one or more embodiments, imiquimod is the active ingredient. It can be used in the formulation as a suspended solid or in solution, alone or in combination with other active agents. As is known to one skilled in the art, in some instances a specific active agent may have more than one activity, function or effect.

Suitable active agents for use in the vehicles and formulations described herein alone or in conjunction with imiquimod include, but are not limited to, active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antpsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, interferons, immunosuppressants, immunoregulating agents, insecticides, insect repellents, keratolytic agents, lactams, metals, metal oxides, mitocides, neuropeptides, steroids, non-steroidal anti-inflammatory agents, oxidizing agents, pediculicides, photodynamic therapy agents, retinoids, sanatives, scabicides, self tanning agents, skin whitening agents, vasoconstrictors, vasodilators, vitamins, vitamin D derivatives, wound healing agents and wart removers as well as agents having activity against superficial basal cell carcinomas, actinic keratoses, Bowen's disease and or other squamous cell carcinomas and molluscum contagiosum. As is known to one skilled in the art, in some instances a specific active agent may have more than one activity, function or effect.

In one or more embodiments, the formulation includes a steroidal anti-inflammatory agent. In an embodiment the wax, waxy substance, counterpart or derivative thereof is present in the composition in an amount sufficient to solubilize the steroid. Exemplary steroidal anti-inflammatory agents include, but are not limited to, corticosteroids such as hydrocortisone, hydroxyltriamcinolone, alpha-methyl dexamethasone, dexamethasone-phosphate, beclomethasone dipropionate, clobetasol valemate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortmate, mepreddisone, paramethasone, prednisolone, prednisone, beclomethasone dipropionate, triamcinolone, and mixtures thereof.

In one embodiment, the formulation includes an immunomodulator. In an embodiment the wax, waxy substance, counterpart or derivative thereof is present in the composition in an amount sufficient to solubilize the immunomodulator. Immunomodulators are chemically or biologically-derived agents that modify the immune response or the functioning of the immune system (as by the stimulation of antibody formation or the inhibition of white blood cell activity). Immunomodulators include, among other options, cyclic peptides, such as cyclosporine, tacrolimus, tresperimus, pimecrolimus, sirolimus (rapamycin), verolimus, laflunimus, laquinimod and imiquimod. Such compounds, delivered in the foam, are especially advantageous in skin disorders such as psoriasis, eczema and atopic dermatitis, where the large skin areas are to be treated.

In one embodiment, the formulation includes an interferon. In an embodiment the wax, waxy substance, counterpart or derivative thereof is present in the composition in an amount sufficient to solubilize the interferon.

In one embodiment, the formulation includes an podophyllin (anti-mitotic), In an embodiment the wax, waxy substance, counterpart or derivative thereof is present in the composition in an amount sufficient to solubilize the podophyllin (anti-mitotic).

In one embodiment, the formulation includes a podofilox. In an embodiment the wax, waxy substance, counterpart or derivative thereof is present in the composition in an amount sufficient to solubilize the podofilox.

In one embodiment, the formulation includes a 5-fluorouracil (5-FU). In an embodiment the wax, waxy substance, counterpart or derivative thereof is present in the composition in an amount sufficient to solubilize the 5-fluorouracil (5-FU).

In an embodiment, the active agent is selected from at least one of imiquimod, an interferon, an immunomodulator, podophyllin (anti-mitotic), podofilox, 5-fluorouracil (5-FU), and trichloroacetic acid (TCA).

In an embodiment, the active agent is selected from at least one of Fluorouracil, afovirsen, inosine pranobex, podophyllum, trichloroacetic acid, thiotep, diclofenac, 5-aminolevulinic acid and derivatives, and tretinoin.

In one or more embodiments imiquimod is used in combination with meglumine antimoniate (for cutaneous leishmaniasis); cryotherapy [liquid nitrogen] (for plantal and periungual warts/actinic keratoses); acyclovir (genital hsv-2 infection); 5-aminolevulinic acid (for genital bowenoid papulosis); fluorouracil (anal and perianal squamous cell carcinoma; salicylic acid (anal and genital warts); a COX inhibitor sulindac (for squamous cell carcinoma).

In one or more embodiments the composition does not contain a basic active agent. In one or more embodiments the composition does not contain an acidic active agent. In other embodiments the composition does not contain a neutralizing active agent. In further embodiments the composition is not partially neutralized by the active agent. In alternative embodiments the active agent may be basic. In still further alternative embodiments the active agent may be acidic. In one or more embodiments the active agent is dissolved in the liquid wax. In one or more preferred embodiments the liquid wax is a fatty acid. In one or more further embodiments the solubilizing power of the liquid wax is boosted by the addition of an organic acid in combination with fatty acid. In other embodiments the solubilizing power of the liquid wax is boosted by the addition of an organic acid in combination with fatty acid and fatty alcohol. Solubilization may also be helped by the presence of an organic hydrophobic solvent such as capric/caprylic triglycerides. In a preferred embodiment the organic acid is a hydroxy acid. Non limiting examples of alpha hydroxy acids are glycolic, lactic, citric, malic and tartaric acid. Beta hydroxy acids include salicylic acid, beta-hydroxybutyric acid, beta-hydroxy beta-methylbutyrate, carnitine, tropic acid trethocanic acid and 3-Hydroxypropionic acid. In a preferred embodiment the hydroxy acids are liquid. In another embodiment the organic acid is a sugar acid including aldonic, uronic and aldaric acids. Particular examples of sugar acids are ascorbic and glucoronic acids. Included are the corresponding salts and pharmaceutically-acceptable derivatives; or any combination of any of the foregoing.

Because of the multiple therapeutic properties of waxes, waxy substances, counterparts and derivatives thereof the combination of such waxes, waxy substances, counterparts and derivatives thereof with imiquimod or another active agents can result in a synergistic therapeutic benefit.

Encapsulation of an Active Agent

In one or more embodiments, the active agent is encapsulated in particles, microparticles, nanoparticles, microcapsules, microspheres, nanocapsules, nanospheres, liposomes, niosomes, polymer matrix, silica-gel, graphite, nanocrystals or microsponges. Such particles can have various functions, such as (1) protection of the active agent from degradation; (2) modification of the active agent release rate from the composition; (3) control of skin penetration profile; and (4) mitigation of adverse effects, due to the controlled release of the active agent from the encapsulation particles.

For example, in one embodiment, the active agent is imiquimod. Imiquimod is difficult to solubilize. For example large amounts of liquid fatty acid isostearic acid are required to solubilize the active agent. Therefore in certain embodiments imiquimod is encapsulated in particles, microparticles, nanoparticles, microcapsules, microspheres, nanocapsules, nanospheres, liposomes, niosomes, polymer matrix, silica-gel, graphite, nanocrystals or microsponges. Such particles can have various functions, such as (1) protection of the imiquimod from degradation; (2) modification of the imiquimod release rate from the composition; (3) control of skin penetration profile; and (4) mitigation of adverse effects, due to the controlled release of the imiquimod from the encapsulation particles.

"Microsponges" are rigid, porous and spongelike round microscopic particles of cross-linked polymer macroporous beads (e.g., polystyrene, copolymers thereof; methyl methacrylate/glycol dimethacrylate crosspolymer), each defining a substantially noncollapsible pore network. Microsponges have a size range in between 5 to 300 μm (typically 10-25 microns) in diameter. The Microsponges can be loaded with an active ingredient and can provide enhanced control, spreadability, safety, stability and improved aesthetic properties including controlled time release of the active ingredient to skin or to a mucosal membrane upon application of the formulation. Release is triggered, for example, by application to the skin surface such as through rubbing and or higher than-ambient skin temperature. The slow release is intended to reduce irritation by the active. Microsponge® delivery technology was developed by Advanced Polymer Systems. Examples of drugs that have been incorporated in microsponges include ibuprofen ketoprofen (non-steroidal anti-inflammatory agent), benzyl peroxide (an anti-acne agent), retinoids, such as retinoic acid and retinol, fluconazole (an antifungal agent). They can also reduce perceived oiliness. Microsponges, when applied to the skin, release the active agent on a time mode and also in response to other stimuli (rubbing, temperature, pH, etc). By delivering the active gradually to the skin, microsponge-benzoyl peroxide formulations, for example, have excellent efficacy with minimal irritation. Microsponges collect on the skin or mucosal surface and slowly release the entrapped agent. The empty spheres are washed away with cleansing.

Microsponges may be incorporated in wide ranges of foam formulations. In one or more embodiments microsponges may be incorporated into the formulations exemplified and described herein. In an embodiment the amount of microsponges may be varied from about 1% to about 25% of the formulation. In some embodiments they are from about 3% to about 15%. In other embodiments they are from about 5% to about 15%. In an embodiment any active agent suitable for loading in microsponges may be used. In specific embodiments active agents such as benzyl peroxide (BPO), tretinoin, hydroquinone, ketoprofen, retinol, fluconazole, ibuprofen, trolamine, a vitamin, imiquimod and the like may be used. As can be noted from above and herein different types of active agents may be loaded into the microsponges. Accordingly, the foam formulation selected in which to disperse the microsponges should be adapted so that the active agent remains substantially entrapped in the microsponges. In certain embodiments the active agent is present both in the foam formulation and in the microsponges so that some of the active agent is available for immediate penetration on application of the foam and that other amounts of active agent are provided by slow or controlled release from the microsponges now sitting on the topical surface. In an embodiment where the active ingredient is insoluble in water and is entrapped in the microsponges there is provided true wax in water emulsion, where the active ingredient is only exposed to the external water phase and does not access the internal wax phase. In an embodiment the foam formulation includes a large amount of hydrophobic surfactant which can form a tight close surfactant layer surrounding the wax droplets sitting in the water phase to separate but still holding the water and wax phases together as an emulsion, thereby preventing or at least substantially reducing any leakage of active agent into the wax phase.

Fields of Applications

The foamable carrier is suitable for treating any inflicted surface. In one or more embodiments, foamable carrier is suitable for administration to the skin, a body surface, a body cavity or mucosal surface, e.g., the cavity and/or the mucosa of the nose, mouth, eye, ear, respiratory system, vagina or rectum (severally and interchangeably termed herein "target site").

In one embodiment, the disorder is a dermatological disorder, which can be treated by an active agent or can prevent or ameliorate the disorder. In another embodiment the disorder is a mucosal disorder.

In another embodiment, the disorder is a dermatological disorder that benefits from the use of imiquimod in conjunction with another active agent. The wax, waxy substance, counterpart or derivative thereof may be of benefit by improving the solubility of the active agent or increasing the penetration of the active agent. The wax, waxy substance, counterpart or derivative thereof may also provide a synergistic therapeutic effect in combination with the active agent.

By selecting a suitable active agent, or a combination of two or more active agents, the foamable composition is useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, eethyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Likewise, the foamable composition is suitable for treating a disorder of a body cavity or mucosal surface, e.g., the mucosa of the nose, mouth, eye, ear, respiratory system, vagina or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranuloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment, the disorder is a dermatological disorder, which can be treated, ameliorated or prevented by a wax, waxy substance, counterpart, or derivative thereof.

In an embodiment, the disorder is a dermatological disorder, which can be treated, ameliorated or prevented by at least one of imiquimod, an interferon, an immunomodulator, podophyllin (anti-mitotic), podofilox, 5-fluorouracil (5-FU), and trichloroacetic acid (TCA).

In an embodiment, the disorder is a dermatological disorder, which can be treated by a topical steroid.

In an embodiment, the disorder is a dermatological disorder, which can be treated by an immunomodulator.

In an embodiment, the disorder is a dermatological disorder, which can be treated by an anti-infective agent, such as an antibacterial agent, and antibiotic, an antifungal agent and an antiviral agent.

In an embodiment, the disorder is a dermatological disorder, which is common in children. Foam is advantageous in the topical treatment of children, who are sensitive to treatment with a cream or ointment.

In an embodiment, the disorder is atopic dermatitis and the active agent is a steroid.

In an embodiment, the disorder is psoriasis and the active agent is a steroid, optionally further including a DCA or DCA ester to stabilize or solubilize the topical steroid.

In an embodiment, the disorder is selected from psoriasis and atopic dermatitis and the active agent comprises a steroid and an additional non-steroidal active agent, such as a vitamin D derivative, optionally further including a DCA or DCA ester to stabilize or solubilize the topical steroid and/or non-steroidal active agent.

In an embodiment, the disorder is selected from psoriasis and atopic dermatitis and the active agent comprises an immunomodulator, optionally further including a DCA or DCA ester to stabilize or solubilize the immunomodulator.

In an embodiment, the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment, the composition is useful for the treatment of wound, ulcer and burn.

The composition is also suitable for administering a hormone to the skin or to a mucosal membrane or to a body cavity, in order to deliver the hormone into the tissue of the target organ, in any disorder that responds to treatment with a hormone.

Other foamable compositions and components for foamable compositions are described in: U.S. Publication No. 05-0232869, published on Oct. 20, 2005, entitled NON-STEROIDAL IMMUNOMODULATING KIT AND COMPOSITION AND USES THEREOF; U.S. Publication No. 05-0205086, published on Sep. 22, 2005, entitled RETINOID IMMUNOMODULATING KIT AND COMPOSITION AND USES THEREOF; U.S. Publication No. 06-0018937, published on Jan. 26, 2006, entitled STEROID KIT AND FOAMABLE COMPOSITION AND USES THEREOF; U.S. Publication No. 05-0271596, published on Dec. 8, 2005, entitled VASOACTIVE KIT AND COMPOSITION AND USES THEREOF; U.S. Publication No. 06-0269485, published on Nov. 30, 2006, entitled ANTIBIOTIC KIT AND COMPOSITION AND USES THEREOF; U.S. Publication No. 07-0020304, published on Jan. 25, 2007, entitled NON-FLAMMABLE INSECTICIDE COMPOSITION AND USES THEREOF; U.S. Publication No. 06-0193789, published on Aug. 31, 2006, entitled FILM FORMING FOAMABLE COMPOSITION; U.S. patent application Ser. No. 11/732,547, filed on Apr. 4, 2007, entitled ANTI-INFECTION AUGMENTATION OF FOAMABLE COMPOSITIONS AND KIT AND USES THEREOF; U.S. Provisional Patent Application No. 60/789,186, filed on Apr. 4, 2006, KERATOLYTIC ANTIFUNGAL FOAM; U.S. Provisional Patent Application No. 0/815,948, filed on Jun. 23, 2006, entitled FOAMABLE COMPOSITIONS COMPRISING A CALCIUM CHANNEL BLOCKER, A CHOLINERGIC AGENT AND A NITRIC OXIDE DONOR; U.S. Provisional Patent Application No. 60/818,634, filed on Jul. 5, 2006, entitled DICARBOXYLIC ACID FOAMABLE VEHICLE AND PHARMACEUTICAL COMPOSITIONS THEREOF; U.S. Provisional Patent Application No. 60/843,140, filed on Sep. 8, 2006, entitled FOAMABLE VEHICLE AND VITAMIN PHARMACEUTICAL COMPOSITIONS THEREOF, all of which are incorporated herein by reference in their entirety. More particularly any of the active ingredients; the solvents; the surfactants; foam adjuvants; penetration enhancers; humectants; moisturizers; and other excipients as well as the propellants listed therein can be applied herein and are incorporated by reference.

The following examples further exemplify the benefits provided by foamable pharmaceutical carriers described in the present application, as well as the benefits of pharmaceutical compositions thereof, methods for preparing the same, and therapeutic uses of the compositions. The examples are for the purposes of illustration only and are not intended to be limiting. Many variations may be carried out by one of ordinary skill in the art and are contemplated within the full scope.

Methodology

A general procedure for preparing foamable compositions is set out in WO 2004/037225, which is incorporated herein by reference.

Emulsion Foam
1. Mix oily phase ingredients and heat to 75° C. to melt all ingredients and obtain homogeneous mixture.
2. Mix polymers, if any, in water with heating or cooling as appropriate for specific polymer. Whilst the polymers may be added instead into the oily phase it was found to be advantageous to prepare them in the water phase.
3. Add all other water soluble ingredients to water-polymer solution and heat to 75° C.
4. Add slowly internal phase to external phase at 75° C. under vigorous mixing and homogenize to obtain fine emulsion. Alternatively the external phase is added slowly to the internal phase.
5. Cool to below 40° C. and add sensitive ingredients with mild mixing.
6. Cool to room temperature.

The above methodology may be used for the wax emulsion formulations. Reasonable changes or variations to the methodology may be introduced as will be appreciated by someone of the art to fit a specific formulation. Specific non limiting examples appear in the Examples section below.

The methodology of loading microsponges with active agent and amounts that can be loaded are described in WO 01/85102, which is incorporated herein by way of reference.

Canisters, Filling and Crimping

The canisters are then filled with the formula prior to addition of propellant, sealed and crimped with a valve and pressurized with the propellant. A nonlimiting exemplary procedure includes the following steps:
1. Each aerosol canister 35×70 mm is filled with 30±5% g of the composition;
2. Each canister is closed with an aerosol valve, using a vacuum crimping machine;
3. Propellant (e.g., mix of propane, butane and isobutane) is added to each of the canisters. Canisters are then warmed for about 30 sec in a warm bath at about 50° C. and well shaken immediately thereafter.

Closure Integrity Test.

Each pressurized canister can be subjected to bubble and crimping integrity testing by immersing the canister in a 60° C. water bath for 2 minutes. Canisters are observed for leakage as determined by the generation of bubbles. Canisters releasing bubbles are rejected.

Production Under Vacuum

Optionally, the foamable formulation may be produced under nitrogen and under vacuum. Whilst the whole process can be carried out under an oxygen free environment, it can be sufficient to apply a vacuum after heating and mixing all the ingredients to obtain an emulsion or homogenous liquid. Preferably the production chamber is equipped to apply a vacuum but if not the formulation can be for example placed in a dessicator to remove oxygen prior to filing and crimping.

Tests

By way of non limiting example the objectives of hardness, collapse time and FTC stability tests are briefly set out below as would be appreciated by a person of the art.

Hardness

LFRA100 instrument is used to characterize hardness. A probe is inserted into the test material. The resistance of the material to compression is measured by a calibrated load cell and reported in units of grams on the texture analyzer instrument display. Preferably at least three repeat tests are made. The textural characteristics of a dispensed foam can effect the degree of dermal penetration, efficacy, spreadability and acceptability to the user. The results can also be looked at as an indicator of softness. Note: the foam sample is dispensed into an aluminum sample holder and filled to the top of the holder.

Collapse Time

Collapse time (CT) is examined by dispensing a given quantity of foam and photographing sequentially its appearance with time during incubation at 36° C. It is useful for evaluating foam products, which maintain structural stability at skin temperature for at least 1 min. Foams which are structurally stable on the skin for at least one minute are termed "short term stable" compositions or foams.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000 CP, the viscosity at 1 RPM may be measured, although the figures are of a higher magnitude.

FTC (Freeze Thaw Cycles)

To check the foam appearance under extreme conditions of repeated cycles of cooling, heating, (first cycle) cooling, heating (second cycle) etc., commencing with −10° C. (24 hours) followed by +40° C. (24 hours) measuring the appearance and again repeating the cycle for up to three times.

Microscopic Examination

The procedure used for evaluating the compositions by microscope examination is as follows:
1) A homogenous formulation or foam produced from a homogenous formulation is taken and a representative sample drop of foam or pre foamed formulation as appropriate is taken and placed on a glass slide using a capillary tube.
2) The drop is carefully covered with a deck glass cover slide
3) The sample is placed under a light microscope (Nikon eclipse 50i) for observation, using a polarizer at a magnification of ×200. Multiple points over the area of the sample are checked.
4) The presence or absence of crystals is noted.
5) If no crystals are observed visually in the sample the formulation is considered to be substantially free of crystals. However, this term does not exclude the possibility of crystals being observed at a higher magnification or occasionally in other samples Sensation Healthy volunteers selected at random were give a sample of foam formulation and applied it to the skin on their hand or forearm and were asked for their observations.

Bubble Size

Foams are made of gas bubbles entrapped in liquid. The bubble size and distribution reflects in the visual texture and smoothness of the foam. Foam bubble size is determined by dispensing a foam sample on a glass slide, taking a picture of the foam surface with a digital camera equipped with a macro lens. The diameter of about 30 bubbles is measured manually relatively to calibration standard template. Statistical parameters such as mean bubble diameter, standard deviation and quartiles are then determined. Measuring diameter may also be undertaken with image analysis software. The camera used was a Nikon D40X Camera (resolution 10 MP) equipped with Sigma Macro Lens (ref: APO MACRO 150 mm F2.8 EX DG HSM). Pictures obtained are cropped to keep a squared region of 400 pixels×400 pixels. The light microscope enables observing and measuring particles from about a few millimeters down to about one micron. Light microscope is limited by the visible light wavelength and therefore is useful to measuring size of particles above 800 nanometers and practically from 1 micron (1,000 nanometers).

Shakability

"Shakability" represents the degree to which the user is able to feel/hear the presence of the liquid contents when the filled pressurized canister is shaken. Shaking is with normal mild force without vigorous shaking or excessive force. When the user cannot sense the motion of the contents during shaking the product may be considered to be non shakable. This property may be of particular importance in cases where shaking is required for affecting proper dispersion of the contents.

Shakability Scoring:

| | |
|---|---|
| Good shakability (conforms to required quality specification) | 2 |
| Moderate shakability (conforms to required quality specification) | 1 |
| Not or hardly shakable but may still be flowable and allow foam formation of quality | 0 |
| Is substantially not able to pass through valve | Block |

Aging or Creaming by Centrifugation

Aging or creaming was evaluated by centrifugation, as described below:
1. Principle of Test The centrifugation used in this procedure serves as a stress condition simulating the aging of the liquid dispersion under investigation. Under these conditions, the centrifugal force applied facilitates the coalescence of dispersed globules or sedimentation of dispersed solids, resulting in loss of the desired properties of the formulated dispersion. The presence of some creaming at the enormous centrifugal forces imposed on the formulations does not derogate from the fact that the compositions have not phase separated and can still be understood as being resistant to creaming and provides a good indication of the long term stability of the formulations. To the extent that good quality stable formulations are achieved, which are resistant to creaming or such that no creaming is observed, the formulations are considered as exceptionally stable. The procedure is as follows:

1.1. Following preparation of the experimental formulation/s, allow to stand at room temperature for ≥24 h.
1.2. Handle pentane in the chemical hood. Add to each experimental formulation in a 20-mL glass vial a quantity of pentane equivalent to the specified quantity of propellant for that formulation, mix and allow formulation to stand for at least 1 h and not more than 24 h.
1.3. Transfer each mixture to 1.5 mL microtubes. Tap each microtube on the table surface to remove entrapped air bubbles.

1.4. Place visually balanced microtubes in the centrifuge rotor and operate the centrifuge at about 300 rpm for 10 min. about 1,000 rpm for 10 min. or at about 3,000 rpm for 10 min or at about 10,000 rpm for 10 min. The centrifuge can be a BHG HEMLE Z 231 M.

1.5. Centrifugation can also be executed at a higher rpm for a shorter period or a lower rpm for a longer period bearing in mind the G force experienced by the formulations is many fold greater than the one G to which a formulation would be exposed to during its shelf life.

Intra-Canister Uniformity

Representative product containers are collected, sample test solutions are prepared and the content of the analyte is determined according to standard methods in the art. Variability of content is characterized as percent difference or relative standard deviation, as appropriate, according to the number of samples evaluated.

The results ascertain variability or uniformity within a given container in content of analytes (primarily active pharmaceutical ingredients, but also preservatives) taken from different parts of a pressurized canister drug products Two full canisters were shaken according to product instructions. About 1-3 g of Foam was dispensed from each canister and discarded. Foam sufficient for two replicate sample solution preparations was then dispensed into a glass beaker. This represents the initial sample. A middle portion is then dispensed from each canister being about half the canister contents. This middle dispensed portion may be discarded or collected for testing purposes, as necessary. Foam sufficient for two replicate sample solution preparations was then dispensed into a glass beaker. This represents the final sample. A small amount of formulation remains in the canister. The foam samples were stirred to remove gas/air bubbles. From both the initial and final foam portions from each canister 4 separate sample solutions are prepared and analyzed, 2 from the initial portion and 2 from the final portion. The percent difference is calculated as follows:

$$\frac{\text{Difference between content determined in initial \& final portions}}{\text{Mean of content of initial \& final portions}} \times 100$$

and the intra canister uniformity evaluated from the results.

Stock Compositions

Non-limiting examples of how stock solutions are made up with and without API. Other stock solutions may be made using the same methodology by simply varying adding or omitting ingredients as would be appreciated by one of the ordinary skills in the art.

EXAMPLES

The invention is described with reference to the following examples. This invention is not limited to these examples and experiments. Many variations will suggest themselves and are within the full intended scope of the appended claims.

Section A—Aqueous Liquid Wax Formulations

A1—Example 1—Vehicle Composition Containing Isostearic Acid

The following foamable vehicles were prepared and the quality of the resultant foam was ascertained.

| | 036 | 007 | 010 | 032 | 040 |
|---|---|---|---|---|---|
| Ingredients | | | | | |
| Isostearic acid | 20 | 30 | 50 | 60 | 60 |
| Pemulen TR-2 | 0.62 | 0.4 | 0.4 | 0.3 | — |
| Polysorbate 80 | 3 | 3 | 3 | 3 | 3 |
| Purified water | 76.38 | 66.6 | 46.6 | 36.7 | 37 |
| Total: | 100 | 100 | 100 | 100 | 100 |
| Propellant AP70 | 8 | 8 | 8 | 8 | 8 |
| Results PFF (pre foam formulation) | | | | | |
| Centrifugation 3K | 30% cr. 10% sep. | 80% cr | 90% cr | stable | 60% cr. |
| Centrifugation 10K | | | | 50% cr. | |
| Microscopic Observation | No Crystals | No Crystals | No Crystals | No Crystals | Yes Crystals |
| Foam | | | | | |
| Appearance | E | E | E– | G | E |
| Color | White | White | White | White | white |
| Odor | 1 | very faint odor | very faint odor | 1 | 1 |
| Shakability | G = Good | Good | Good | Good | Good |
| Density (g/mL) | 0.045 | n/a | n/a | 0.063 | 0.045 |
| Microscopic Observation | No Crystals | No Crystals | No Crystals | No Crystals | Yes Crystals |
| Collapse time 36° C. (sec) | >300/FG | >300/G | >300/FG | >300/FG | |
| Foam pH (diluted 1:5) | 3.93 | n/a | n/a | 4.08 | |

Compositions contain 20%, 30%, 50%, 60%, isostearic acid to provide; (1) solubilizing capacity; and (2) potentially enhanced skin delivery of an active agent and (3) some emolliency and or (4) some substantially organized chaos by virtue of its non linear shape enabling both shakability and flowability of the wax formulation and potentially enhanced skin penetration.

The compositions contain from about 66% to about 37% water. Therefore, they can provide a good skin feeling effect even at high concentrations.

Up to about 60% isostearic acid the compositions are believed to be wax in water emulsions. The 60% formulation was examined by water addition test was found to be liquid wax in water emulsion despite the fact that the amount of liquid wax phase was approximately double that of the aqueous phase. Liquid wax in water emulsion is maintained and stabilized by selecting a surfactant that favors liquid wax in water emulsions over water in liquid wax emulsions. Hence, the skin feeling of the composition is favorable.

At about 70% isostearic acid there is significant tension to form a water in liquid wax emulsion. Using 0.4% permulen with 3% polysorbate 80, which favours a liquid wax in water emulsion, did not release foam at these levels of isostearic acid. Reducing the permulen to half resulted in a poor foam. By using PEG 30 dipolyhydroxysearate (Arlacel P-135) it is possible to form a water in liquid wax emulsion, however it produced a poor foam with or without polymer. It is predicted though, (based on 70% oleyl alcohol foam exemplified below in Example 3), that at about 70% isostearic acid with polysorbate 80 as surfactant and no polymer, a foam of quality can still be produced.

Without being bound to any particular theory the physical change in the formulation may be due to isostearic acid reaching a concentration where phase reversal from wax in water to water in wax emulsion is possible. Also at this concentration range of isostearic acid removal of the polymeric agent, which itself can absorb water may—without being bound by any theory—perhaps reduce internal emulsion tensions resulting from the presence of the thickening polymeric agent and thereby unexpectedly resulting in improved foam quality even though polymeric agents are normally added to strengthen foam quality. Also as the concentration of isostearic acid increased and consequently the amount of water decreased it may be that the amount of surfactant required can be reduced as the external water phase is thinner.

It further appears to be the case that—without being limited by any theory—for any given emulsion system as the liquid wax phase is increased with a corresponding decrease in the water phase the internal tension or pressure for phase reversal will increase and the point at which the phase reversal can occur can be retarded by selective use of non traditional derivatized polymeric agents with emulsifying properties, such as permulen that can stabilize the formulation and help improve resistance to creaming they may in small amounts be able to push back the point at which pressure for phase reversal might otherwise occur but subject to the caveat that whilst removal of polymer may improve visual foam appearance it can result in a lesser resistance to creaming. By fine tuning of the formulations and or addition of other stabilising substances as can be seen in Examples 2, 3, 4 and Example 8 the resistance to creaming can be improved.

A foam of quality was not achieved with only permulen and isostearic acid.

These compositions can be used as a vehicle for pharmaceutical and cosmetic agents especially those soluble in liquid waxes or water. For example imiquimod is soluble in isostearic acid.

In order to create a foamable composition, the composition is filled into an aerosol canister and pressurized using a liquefied or gas propellant can be added at a concentration of about 3% to about 25%.

A1—Example 2—Vehicle Composition Containing Isostearic Acid, Oleyl Alcohol and Active Agent The following foamable pharmaceutical compositions were prepared and the quality of the resultant foam was ascertained.

| Ingredients | 002 | 003 |
|---|---|---|
| Isostearic acid | 30 | 30 |
| Caprilic/capric triglycerides | 2.5 | 2.5 |
| Oleyl alcohol | 7.5 | 7.5 |
| Sorbitan Stearate | 0.65 | 0.65 |
| Imiquimod | 5 | 5 |
| Benzyl alcohol | 2 | 2 |
| Xanthan gum | 0.35 | — |
| Hydroxypropyl methylcellulose | 0.35 | — |
| Glycerin | 2 | 2 |
| Polysorbate 60 | 2.5 | 2.5 |
| Methyl hydroxybenzoate | 0.2 | 0.2 |
| Propyl hydroxybenzoate | 0.02 | 0.02 |
| Purified water | 46.93 | 47.63 |
| Total: | 100 | 100 |
| Propellant AP70 | 8 | 8 |
| Results PFF (pre foam formulation) | | |
| Centrifugation 3K | stable | 55 |
| Viscosity (cPs) | 12806 | 18.2 |
| Microscopic Observation | No Crystals | No Crystals |
| Foam | | |
| Visual inspection (pressurized glass bottle) | Homogeneous | Homogeneous |
| Appearance | G | G |
| Color | White | White |
| Odor | very faint odor | very faint odor |
| Shakability | moderate | Good |
| Density (g/mL) | 0.051 | 0.039 |
| Microscopic Observation | No Crystals | No Crystals |
| Collapse time 36° C. (sec) | >300/FG | >300/FG |

These compositions contain 30% isostearic acid and 7.5% oleyl alcohol and 2.5% capric caprylic triglycerides to provide (1) emolliency; (2) solubilizing capacity; and (3) potentially enhanced skin delivery of an active agent and or (4) some organized chaos by virtue of the non linear shape of the liquid waxes enabling both shakability and flowability of the wax formulation and potentially enhanced skin penetration.

Formulation 02 was found to be stable to centrifugation at 3000 rpm for 10 minutes indicating that it should be substantially resistant to aging and physically shelf stable.

The compositions contain about 47% water. Therefore, they provide a good skin feeling effect.

The compositions are oil in water emulsions. Hence, the skin feeling of the composition is favorable.

The compositions can be used for topical therapy of a skin disorder treatable by imiquimod, which can include treating, containing, ameliorating or preventing actinic keratosis, superficial basal cell carcinoma and external genital warts.

These compositions can be used as a vehicle for other pharmaceutical and cosmetic agents especially those soluble in liquid waxes or water.

In order to create a foamable composition, the composition is filled into an aerosol canister and pressurized using a liquefied or gas propellant can be added at a concentration of about 3% to about 25%.

A2—Example 3—Vehicle Composition Containing Oleyl Alcohol

The following foamable vehicles were prepared and the quality of the resultant foam was ascertained.
(a) Oleyl alcohol alone from 20% to 70%

| Ingredients | 037 | 006 | 009 | 015 | 031 | 039 | 044 |
|---|---|---|---|---|---|---|---|
| Oleyl alcohol | 20 | 30 | 50 | 60 | 60 | 60 | 70 |
| Pemulen TR-2 | 0.62 | 0.4 | 0.4 | 0.4 | 0.3 | — | — |
| Polysorbate 80 | 3 | 3 | 3 | 3 | 3 | 3 | 3 |
| Purified water | 76.38 | 66.6 | 46.6 | 36.6 | 36.7 | 37 | 27 |
| Total: | 100 | 100 | 100 | 100 | 100 | 100 | 100 |

| Ingredients | 037 | 006 | 009 | 015 | 031 | 039 | 044 |
|---|---|---|---|---|---|---|---|
| Propellant AP70 | 8 | 8 | 8 | 8 | 8 | 8 | 8 |
| Results PFF (pre foam formulation) | | | | | | | |
| Centrifugation 3K | 20% cr. 20% sep. | 80% cr | 90% cr | — | stable | 60% cr. | 60% cr. |
| Centrifugation 10K | | | | — | 50% cr. | | |
| Microscopic Observation | No Crystals | No Crystals | No Crystals | — | No Crystals | No Crystals | No Crystals |
| Foam | | | | | | | |
| Appearance | E = excellent | E | E | FG = fairly good | G = Good | G | G+ |
| Color | White | White | White | — | White | white | white |
| Odor | 1 | very faint odor | very faint odor | — | 1 | 1 | 1 |
| Shakability | Good | Good | Good | — | Good | Good | Good |
| Density (g/mL) | 0.045 | n/a | n/a | — | 0.062 | 0.041 | 0.059 |
| Microscopic Observation | No Crystals | No Crystals | No Crystals | — | No Crystals | No Crystals | No Crystals |
| Collapse time 36° C. (sec) | >300/FG | >300/FG | >300/FG | — | | | |
| Foam pH (diluted 1:5) | 3.89 | | | | 4.16 | | |

The compositions contain 20%, 30%, 50%, 60%, and 70% oleyl alcohol to provide: (1) solubilizing capacity; and (2) potentially enhanced skin delivery of an active agent and (3) some emolliency and/or (4) some substantially organized chaos by virtue of its non linear shape enabling both shakability and flowability of the wax formulation and potentially enhanced skin penetration.

The compositions contain from about 66% to about 27% water. Therefore, they can provide a good skin feeling effect even at high concentrations.

Up to about 70% oleyl alcohol the compositions are believed to be wax in water emulsions, The 60% and 70% formulations were examined by water addition test and were found to be liquid wax in water emulsions despite the fact that the amount of liquid wax phase was approximately more than double that of the aqueous phase. Liquid wax in water emulsion is maintained and stabilized by selecting a surfactant that favors liquid wax in water emulsions over water in liquid wax emulsions. Preferably, the surfactant is or comprises a non ionic surfactant. More preferably the non ionic surfactant has a HLB (or average weighted HLB if more than one) reasonably close to the required HLB (or average weighted required HLB if more than one) of the liquid wax. Other factors in the selection of the surfactants are those in which the hydrophilic end is more dominant than the hydrophobic end; those containing a fatty acid chain at its hydrophobic end which is not dissimilar to the fatty chains of the liquid wax; or is a polymeric surfactant; or is a combination of surfactants each with one or more of these properties. Hence, the skin feeling of the composition is favorable.

Interestingly, the method of manufacture is significant in producing a foam of good quality. For example, at 60% isostearic acid, if the polymer is dispersed in the liquid wax phase then only fairly good foam is achieved but if instead the polymer is added the water phase to form a gel and the surfactant is then added to the gel and finally the liquid wax phase is added to the composition (as described in the methodology) then a foam of good quality is produced even though the polymer is reduced.

At about 60% there may be tension to form a water in liquid wax emulsion and at about 70% oleyl alcohol there is significant tension to form a water in liquid wax emulsion. Surprisingly, by removing the polymer at 60% and at 70% oleyl alcohol the foam quality is improved.

Using 0.4% permulen with 3% polysorbate 80, which favours a liquid wax in water emulsion, did not release foam at 70% of oleyl alcohol. Increasing the surfactant to 5% or reducing the permulen to half resulted in a poor foam.

By using PEG 30 dipolyhydroxysearate instead of polysorbate 80 it is possible to form a water in liquid wax emulsion, however it produces poor foam with polymer and without polymer. On the other hand if polysorbate 80 is used as surfactant, which favours a liquid wax in water emulsion then a foam of excellent quality is achieved without polymer at 60% and at 70%.

Without being bound to any particular theory the physical change in the formulation may be due to oleyl alcohol reaching a concentration where phase reversal from liquid wax in water to water in liquid wax emulsion is possible. Also at this concentration range of oleyl alcohol removal of the polymeric agent, which itself can absorb water may—without being bound by any theory—perhaps reduce internal emulsion tensions resulting from the presence of the thickening polymeric agent and thereby unexpectedly resulting in improved foam quality even though polymeric agents are normally added to strengthen foam quality. Also as the concentration of oleyl alcohol increased and consequently the amount of water decreased it may be that the amount of surfactant required can be reduced as the external water phase is thinner.

It further might possibly be the case that—without being limited by any theory—for a given emulsion system as the liquid wax phase is increased with a corresponding decrease in the water phase the internal tension or pressure for phase reversal will increase and the point at which the phase reversal can occur can be retarded by selective use of non traditional derivatized polymeric agents with emulsifying properties, such as permulen that can stabilize the formulation and help improve resistance to creaming, they may in small amounts be able to push back the point at which pressure for phase reversal might otherwise occur but subject to the caveat that whilst removal of polymer may improve visual foam appearance it can result in a lesser resistance to creaming. By fine tuning of the formulations and or addition of other stabilizing substances resistance to creaming can be improved.

These compositions can be used as a vehicle for pharmaceutical and cosmetic agents especially those soluble in liquid waxes or water. For example imiquimod is soluble in isostearic acid.

Formulations 06, 09, 31, 39 and 44 were found to be substantially resistant to creaming when subjected to centrifugation at 3000 rpm for 10 minutes. With adjustment these formulations could be stable to centrifugation as can be seen from formulation 31, indicating that they should be substantially resistant to aging and physically shelf stable.

Oleyl alcohol is a defoamer and is therefore harder to formulate in foam formulations than octyldodecanol or isostearyl alcohol, which are also liquid fatty alcohols. Thus, by way of prophetic example the above formulations may be made with either octyldodecanol or isostearyl alcohol alone or in combination.

In order to create a foamable composition, the composition is filled into an aerosol canister and pressurized using a liquefied or gas propellant can be added at a concentration of about 3% to about 25%.

3(b) 12% Oleyl Alcohol (Liquid) with 8% Isostearyl Acid (Liquid) or 8% Stearic Acid (Solid)

| | HLB/RHLB | 012 | 013 |
|---|---|---|---|
| Ingredients | | | |
| Isostearic acid | 13 | 8.00 | |
| Stearic acid | 15.5 | | 8.00 |
| Oleyl alcohol | 14 | 12.00 | 12.00 |
| Ceteareth-20 | 15.2 | 0.90 | |
| Polysorbate 80 | 15 | | 1.30 |
| Glyceryl stearate | 3.8 | 1.40 | 1.00 |
| PEG 100 stearate | 18.8 | 2.40 | 2.40 |
| Purified water | | 75.30 | 75.30 |
| Total | | 100.00 | 100.00 |
| Propellant (AP-70) | | 8.00 | 8.00 |
| Appearance | | | |
| Quality | | Good-Excellent | Good-Excellent |
| Color | | White | White |
| Odor | | No odor | No odor |
| Shakability | | Good | Good |
| Microscope | | No Crystals | No Crystals |
| Density | | 0.038 | 0.044 |
| Bubble size (μM) | | 144.00 | 93.00 |
| Bubble size (above 500 μM) | | 0.00 | 0.00 |

Comments: Formulations with 12% oleyl alcohol as liquid wax were able to achieve good to excellent foam in combination either a liquid fatty acid or a solid fatty acid at 8%. As oleyl alcohol can have destabilising or defoaming properties especially as the concentration increases then prophetically replacing oleyl alcohol with another liquid alcohol such as octyldodecanol or isostearyl alcohol would be expected to yield foamable formulations which are similar or perhaps even better. Formulation 12 had good spreadabiliy, good skin feeling and quick absorption without a waxy sensation. Formulation 13 also had good spreadabiliy, good skin feeling and relatively quick absorption with a delicate waxy sensation.

A1—Example 4—Vehicle Compositions Containing Jojoba Oil

The following foamable vehicles were prepared and the quality of the resultant foam was ascertained.

| | 038 | 021 | 025 | 033 |
|---|---|---|---|---|
| Ingredients | | | | |
| Jojoba Oil | 20 | 50 | 60 | 70 |
| Pemulen TR-2 | 0.62 | 0.4 | 0.3 | 0.22 |
| Polysorbate 80 | 3 | 3 | 3 | 3 |
| Purified water | 76.38 | 46.6 | 36.7 | 26.78 |
| Control: | 100 | 100 | 100 | 100 |
| Propellant AP70 | 8 | 8 | 8 | 8 |
| Results | | | | |
| PFF (pre foam formulation) | | | | |
| Centrifugation 3K | 20% cr. 20% sep | 40% cr. | 10% cr. | stable |
| Centrifugation 10K | | | | 30% cr. |
| Viscosity (cPs) | | 4025 | 6117 | |
| Microscopic Observation | No Crystals | No Crystals | No Crystals | No Crystals |
| Foam | | | | |
| Appearance | G | G- | G- | G |
| Color | Yellowish | cream | cream | Yellowish |
| Odor | 1 | 1 | 1 | 1 |
| Shakability | Good | Moderate | Moderate | Moderate |
| Density (g/mL) | 0.05 | 0.102 | 0.093 | 0.067 |
| Microscopic Observation | No Crystals | No Crystals | No Crystals | No Crystals |
| Collapse time 36° C. (sec) | >300/G | | | >300/G |
| Foam pH (diluted 1:5) | 3.79 | 3.93 | 4.08 | 4.19 |

These compositions contain 20%, 30%, 50%, 60%, and 70% of jojoba oil (otherwise is known as liquid wax), which somewhat resembles sebum in nature to provide (1) solubilizing capacity; and (2) potentially enhanced skin delivery of an active agent and (3) some emolliency and or (4) some organized chaos by virtue of its non linear shape enabling both shakability and flowability of the wax formulation and potentially enhanced skin penetration.

The compositions contain from about 66% to about 27% water. Therefore, they can provide a good skin feeling effect even at high concentrations.

Up to about 70% jojoba the compositions are believed to be wax in water emulsions, Liquid wax in water emulsion is maintained and stabilized by selecting a surfactant that favors liquid wax in water emulsions over water in liquid wax emulsions. Hence, the skin feeling of the composition is favorable.

Although at 70% oleyl alcohol and at 70% isostearic acid there is significant tension to form a water in liquid wax emulsion at 70% jojoba oil the composition can still form a liquid wax in water emulsion despite that water is only about a quarter of the composition. The extra stability of the emulsion may, without being bound to any particular theory, be ascribed to its much longer fatty chain back bone being about double of that of oleyl alcohol and of isostearic acid.

Also at this concentration range of jojoba oil removal of the polymeric agent, which itself can absorb water may—without being bound by any theory—perhaps reduce internal emulsion tensions resulting from the presence of the thickening polymeric agent and thereby unexpectedly resulting in improved foam quality even though polymeric agents are normally added to strengthen foam quality. Also as the concentration of jojoba oil increased and consequently the amount of water decreased it may be that the amount of surfactant required can be reduced as the external water phase is thinner.

It further appears to be the case that—without being limited by any theory—for any given emulsion system as the liquid wax phase is increased with a corresponding decrease in the water phase the internal tension or pressure for phase reversal will increase and the point at which the phase reversal can occur can be retarded by selective use of non traditional derivatized polymeric agents with emulsifying properties, such as permulen that can stabilize the formulation and help improve resistance to creaming, they may in small amounts be able to push back the point at which pressure for phase reversal might otherwise occur but subject to the caveat that whilst removal of polymer may improve visual foam appearance it can result in a lesser resistance to creaming. By fine tuning of the formulations and or addition of other stabilising substances resistance to creaming can be improved.

A foam of quality was not achieved with only permulen and oleyl alcohol.

These compositions can be used as a vehicle for pharmaceutical and cosmetic agents especially those soluble in liquid waxes or water. For example, imiquimod is soluble in isostearic acid.

In order to create a foamable composition, the composition is filled into an aerosol canister and pressurized using a liquefied or gas propellant can be added at a concentration of about 3% to about 25%.

Example 5

Fatty Alcohol Combination Emulsion Formulations

|  | HLB/RHLB | 002 | 004 |
| --- | --- | --- | --- |
| Ingredients |  |  |  |
| Oleyl alcohol | 14 | 19.00 | 19.00 |
| Isostearyl alcohol | ~13 | 19.00 | 19.00 |
| Octyldodecanol | ~14 | 19.00 | 19.00 |
| Cetearyl alcohol | 15.5 | 2.00 | 3.00 |
| Ceteareth-20 | 15.2 |  | 2.90 |
| Polysorbate 60 | 14.9 | 4.00 |  |
| Polysorbate 80 | 15 |  | 2.40 |
| Glyceryl stearate | 3.8 | 1.00 | 0.70 |
| PEG 100 stearate | 18.8 | 1.00 |  |
| Sorbitane stearate | 4.7 |  |  |
| PEG-30 dipolyhydroxystearate | 5.5 |  |  |
| Purified water |  | 35.00 | 34.00 |
| Total |  | 100.00 | 100.00 |
| Propellant (AP-70) |  | 8.00 | 8.00 |
| Appearance |  |  |  |
| Quality |  | Poor | Good+ |
| Color |  |  | White |
| Odor |  |  | No odor |
| Shakability |  |  | Good |
| Bubble size (μm) |  |  | 149.00 |
| Bubble size (above 500 μm) |  |  | 0.00 |
| Hardness |  |  | 13.13 |

Comments: It is possible to achieve good quality foam with high concentrations (about 60%) of fatty alcohol emulsion formulation by using only surfactants. The foam quality was greatly improved by increasing the solid fatty alcohol from 2% to 3% and changing the surfactants. The formulations may comprise a single fatty alcohol (See Example 3) or combinations of two or three or more fatty alcohols (See Example 5).

Example 6: ~57% Isostearic Acid and 5% Imiquimod Using a Polymeric Surfactant Pemulen

|  | 009 (cf 032) |
| --- | --- |
| Ingredients |  |
| Isostearic acid | 56.90 |
| Pemulen TR-2 | 0.30 |
| Polysorbate 80 | 3.00 |
| Purified water | 34.80 |
| Imiquimod | 5.00 |
| Total | 100.00 |
| Propellant AP70 | 8.00 |
| Results |  |
| Foam quality | Good |
| Color | White |
| Odor | No Odor |
| Shakability | Good |
| Microscopic Observation | No Crystals |

Comments: This formulation is based on the vehicle 32 of Example 1 which produced good quality foam. The addition of imiquimod did not destabilize the formulation and the imiquimod was fully dissolved with no crystals being microscopically observed.

Section B—Aqueous Solid Wax Formulations

B1—Example 7—Vehicle Composition Containing Stearic Acid

The following foamable vehicles were prepared and the quality of the resultant foam was ascertained.

|  | 024 |
| --- | --- |
| Ingredients |  |
| Stearic acid | 30 |
| Polysorbate 80 | 10 |
| Purified water | 60 |
| Control: | 100 |
| Propellant Butane | 20 |
| Results |  |
| PFF (pre foam formulation) |  |
| Microscopic Observation | Crystals |
| Foam |  |
| Appearance | G |
| Color | white |
| Microscopic Observation | Crystals |

Compositions contain up to about 30% stearic acid to provide (1) some emolliency; (2) body as a waxy thickener; (3) possibly some solubilizing capacity; and (4) possibly enhanced skin delivery of an active agent.

The compositions are wax in water emulsions and contain from about 60% water. Therefore, they can provide a good skin feeling effect even at high stearic acid concentrations.

As a foam adjuvant in foamable formulations stearic acid is used at concentrations of up to about 5% and preferably between about 1% and about 3%. Beyond 5% it is used as a thickening agent although usually at levels of not more than at about 8%. Its use beyond about 9% for foamable compositions was thought inappropriate since it would tend to support the formation of a solid block from which it was not possible to make a foam especially where traditional types of polymeric agents and or solid surfactants, were used in the formulations for example, CMC at levels of say up to or about 5% and or steareth 21 at levels of say up to or about 5%. Surprisingly it was discovered that is was possible to use much higher levels of stearic acid to produce foamable compositions of good quality by avoiding the use of polymeric agents, by using liquid surfactants and by use of higher levels of hydrophobic propellant. As the level of stearic acid approaches about 30% it tends towards not releasing foam. However, by selective use of liquid surfactants in higher concentrations and or higher levels of hydrophobic propellants it was possible to achieve a shakable flowable composition, which produced good quality foam. Thus, the upper limit of stearic acid that can be used in a foamable composition is determined by its shakability and more importantly its flowability.

For example, where stearic acid is 30% and only 3% Polysorbate 80 is used poor foam is obtained. However, by increasing the liquid surfactant to about 10% so it acts as both as a solvent and as a surfactant and raising the propellant to 20% then surprisingly it was possible to obtain a foam of good quality based on a wax/water/surfactant composition even at such high levels of solid wax in water. However crystals were observed. This problem was overcome by formulating liquid with solid wax. Thus as can be seen in Example 7 in the presence of liquid wax no crystals were observed in 30% stearic acid formulations.

Solid waxes form a wax in water emulsion when heated in the presence of surfactant with agitation, however unlike liquid wax or liquid waxy substances they cool to form solid lipid like suspensions having unique roundish particles that cannot be obtained from milling, which suspensions nevertheless appear to be like emulsions.

A foam of quality was not achieved with only permulen and 30% stearic acid. Addition of polysorbate 80, a liquid surfactant, did not appear to make a significant difference at a usual surfactant level of 3%.

These compositions can be used as a vehicle for pharmaceutical and cosmetic agents especially those soluble in waxes or water.

In order to create a foamable composition, the composition is filled into an aerosol canister and pressurized using a liquefied or gas propellant can be added at a concentration of about 3% to about 35%. Preferably between 12% to 25%.

Section C—Aqueous Formulation with Liquid and Solid Wax

C1—Example 8—Vehicle Composition Containing Oleyl Alcohol, Stearyl Alcohol, Cetyl Alcohol and Stearic Acid The following foamable vehicles were prepared and the quality of the resultant foam was ascertained.

|  | 001 |
| --- | --- |
| Ingredients | |
| Stearic acid | 30 |
| Cetyl alcohol | 4 |
| Stearyl alcohol | 3 |
| Caprilic/capric triglycerides | 2.5 |
| Oleyl alcohol | 7.5 |
| Sorbitan Stearate | 0.65 |
| Benzyl alcohol | 2 |
| Xanthan gum | 0.35 |
| Hydroxypropyl methylcellulose | 0.35 |
| Glycerin | 2 |
| Polysorbate 60 | 2.5 |
| Methyl hydroxybenzoate | 0.2 |
| Propyl hydroxybenzoate | 0.02 |
| Purified water | 44.93 |
| Control: | 100 |
| Propellant AP70 | 8 |
| Results | |
| PFF (pre foam formulation) | |
| Microscopic Observation | No Crystals |
| Foam | |
| Visual inspection (pressurized glass bottle) | Homogeneous |
| Appearance | G |
| Color | White |
| Odor | no odor |
| Shakability | poor |
| Density (g/mL) | 0.04 |
| Microscopic Observation | No Crystals |
| Collapse time 36° C. (sec) | >300/G |
| Foam pH (diluted 1:5) | 4.65 |

Surprisingly it was possible to make aqueous foam compositions of good quality with solid wax of up to about 37% by addition of about 7.5% liquid wax. The upper amount of solid wax that may be added is such that the formulation remains substantially flowable. Also by using (and increasing the amount of) surfactant in which the solid wax dissolves—preferably a liquid surfactant—it may be possible to increase further the amount of solid wax in the formulation.

C1—Example 9—Vehicle Composition Containing Isostearic Acid and Stearic Acid

The following foamable vehicles were prepared and the quality of the resultant foam was ascertained.

|  | 023 | 027 | 029 | 030 |
| --- | --- | --- | --- | --- |
| Ingredients | | | | |
| Isostearic acid | 40 | 45 | 55 | 50 |
| Stearic acid | 30 | 25 | 15 | 20 |
| Arlacel P-135 | 2 | 2 | 2 | 2 |
| Sodium Chloride | 0.5 | 0.5 | 0.5 | 0.5 |
| Purified water | 27.5 | 27.5 | 27.5 | 27.5 |
| Control: | 100 | 100 | 100 | 100 |
| Propellant AP70 (except in 23) | 10 butane | 8 | 8 | 8 |
| Results | | | | |
| PFF (pre foam formulation) | | | | |
| Centrifugation 3K | — | 90% cr. | — | — |
| Centrifugation 10K | — | | — | — |
| Viscosity (cPs) | — | 12407 | — | — |
| Microscopic Observation | — | No Crystals | — | — |
| Foam | | | | |
| Appearance | FG/G | G | FG | FG |
| Color | — | White | — | — |
| Odor | — | 1 | — | — |
| Shakability | — | Good | — | — |
| Microscopic Observation | — | No Crystals | — | — |

By making effective use of and combining the surprising properties of liquid waxes with the special characteristics of solid waxes it was surprisingly found possible to make formulations of about 70% waxes, which are shakable, flowable and form foams of fairly good and of good quality even where solid wax is present at a concentration of 30%.

Such compositions contain 40% to 55% isostearic alcohol to provide (1) solubilizing capacity; and (2) potentially enhanced skin delivery of an active agent and (3) some emolliency and or (4) some substantially organized chaos by virtue of its non linear shape enabling both shakability and flowability of the wax formulation and potentially enhanced skin penetration. In one particular embodiment, the ratio of isostearic acid to stearic acid is about 9:5.

It is believed that even higher concentrations of isostearic acid may be reached by reducing the water alone or in combination with a reduction of stearic acid. It is also expected that replacement of isostearic acid with oleyl alcohol would produce similar results save that—as oleyl alcohol produces formulations which are a little thicker than those with the same amount of isostearic acid—possibly the oleyl alcohol formulations might not be able to accommodate as higher level of stearic acid as can isostearic acid. Formulations with lower levels of isostearic acid are clearly possible.

The compositions in the example contain about 27% water. Therefore, they can provide a relatively good skin feeling effect even at such high wax concentrations.

Formulation 27 was examined by water addition test and was found to be water in liquid wax emulsion. By use of a surfactant favoring wax in water emulsions as seen elsewhere in the Examples it may be possible to achieve a water in liquid wax emulsion even at these high concentrations.

These compositions can be used as a vehicle for pharmaceutical and cosmetic agents especially those soluble in liquid waxes or water. For example imiquimod is soluble in isostearic acid.

In order to create a foamable composition, the composition is filled into an aerosol canister and pressurized using a liquefied or gas propellant can be added at a concentration of about 3% to about 25%.

C1—Example 10—Vehicle Composition Containing Isostearic Acid, One or More of Oleyl Alcohol, Cetyl Alcohol and Stearyl Alcohol, and Active Agent The following foamable vehicles were prepared and the quality of the resultant foam was ascertained.

|  | 003 | 005 | 006 | 007 |
|---|---|---|---|---|
| Ingredients |  |  |  |  |
| Isostearic acid | 30 | 25 | 25 | 25 |
| Cetyl alcohol | 4 | 2.2 | 2.2 | — |
| Stearyl alcohol | 3 | 3.1 | 3.1 | 3.1 |
| Caprilic/capric triglycerides | 2.5 | — | — | — |
| Oleyl alcohol | 7.5 | — | — | — |
| White soft paraffin | — | 3 | 3 | 3 |
| Sorbitan Stearate | 0.65 | 0.6 | 0.6 | 0.6 |
| PEG-40 Stearate | — | — | — | 1 |
| Imiquimod | 5 | 5 | 5 | 5 |
| Benzyl alcohol | 2 | 2 | 2 | 2 |
| Xanthan gum | 0.35 | 0.5 | 0.25 | 0.25 |
| Hydroxypropyl methylcellulose | 0.35 | 0.5 | 0.25 | 0.25 |
| Glycerin | 2 | 2 | 2 | 2 |
| Polysorbate 60 | 2.5 | 3.4 | 3.4 | 3.4 |
| Methyl hydroxybenzoate | 0.2 | 0.2 | 0.2 | 0.2 |
| Propyl hydroxybenzoate | 0.02 | 0.02 | 0.02 | 0.02 |
| Purified water | 39.93 | 52.48 | 52.98 | 54.18 |
| Control: | 100 | 100 | 100 | 100 |
| Propellant AP70 | 8 | 8 | 8 | 8 |
| Results |  |  |  |  |
| Foam Quality | G | G/block | FG | G |
| Shakability | shakable | No shakability but some flowability | shakable | shakable |
| Color | White | White | White | White |
| Odor | No odor | No odor | No odor | No odor |
| Density | 0.068 | 0.071 | 0.059 | 0.049 |
| Collapse time (sec) | >300 | — | >300 | >300 |
| Microscopic observation | No crystals | No crystals | No crystals | No crystals |
| Centrifugation 3000 rpm | homogeneous | homogeneous | homogeneous | homogeneous |

These compositions contain 30% isostearic acid and about 3% stearyl alcohol. Optionally they may also contain one or more of some cetyl alcohol, oleyl alcohol and capric caprylic triglycerides to provide (1) emolliency; (2) solubilizing capacity; and (3) potentially enhanced skin delivery of an active agent and or (4) some organized chaos by virtue of the non linear shape of the liquid waxes enabling both shakability and flowability of the wax formulation and potentially enhanced skin penetration.

The compositions contain about 40% to about 55% water. Therefore, they provide a good skin feeling effect.

The compositions are oil in water emulsions. Hence, the skin feeling of the composition is favorable.

The compositions can be used for topical therapy of a skin disorder treatable by imiquimod, which can include treating, containing, ameliorating or preventing actinic keratosis, superficial basal cell carcinoma and external genital warts.

These compositions can be used as a vehicle for other pharmaceutical and cosmetic agents especially those soluble in liquid waxes or water.

In order to create a foamable composition, the composition is filled into an aerosol canister and pressurized using a liquefied or gas propellant can be added at a concentration of about 3% to about 25%.

Example 11: Isostearic Acid and Stearic Acid Emulsion Formulations—Minimum Ingredients

| cf | HLB/RHLB | Ex. 7 (029) 001- | Ex. 7 (029) 003 |
|---|---|---|---|
| Isostearic acid | 13 | 55.00 | 55.00 |
| Stearic acid | 15.5 | 15.00 | 15.00 |
| Ceteareth-20 | 15.2 |  | 2.50 |
| Polysorbate 80 | 15 | 2.60 |  |
| Sorbitane oleate | 4.3 | 0.40 |  |

-continued

| cf | HLB/RHLB | Ex. 7 (029) 001- | Ex. 7 (029) 003 |
|---|---|---|---|
| Sorbitane stearate | 4.7 | | 0.50 |
| Purified water | | 27.00 | 27.00 |
| Total | | 100.00 | 100.00 |
| Propellant (AP-70) | | 8.00 | 8.00 |
| Appearance | | | |
| Quality | | Good− | Good+ |
| Color | | White | White |
| Odor | | No odor | No odor |
| Shakability | | Good | Good |

Comments: It is possible to achieve good quality foam with high concentrations (70%) of fatty acids by using only surfactants. In the two formulations the ratio of solid to liquid fatty acids is about 3:11.

Methodology for formulations 001-006 in Examples 5, 11, 12 and for formulations 012 and 013 in Example 3(b):
1) Heat all ingredients (other than water) to 60-70 C to complete dissolution.
2) Heat water to 60-70 C.
3) Add water to 1 while mixing. Mix for about 10 minutes.
4) Cool to RT while mixing. Add water to adjust formulation to 100% while mixing.

Methodology for formulation 007 in Example 12:
1) Heat all ingredients (other than water, xanthan gum, hydroxypropyl methylcellulose, benzyl alcohol and glycerin) to 60-70 C to complete dissolution.
2) Add Xanthan gum and Hydroxypropyl methylcellulose to water at RT to dissolve. Heat to 60-70 C.
3) Add 2 to 1 while mixing. Mix for about 10 minutes. Alternatively 1 can be added to 2.
4) Cool to RT while mixing. Add Benzyl alcohol and Glycerin. Add water to adjust formulation to 100% while mixing.

Methodology for formulation 008 in Example 13:
1) Heat Isostearic acid to 60-70 C. Add Imiquimod to complete dissolution. Add Stearic acid and PEG-30 dipolyhydroxystearate to complete dissolution.
2) Add Sodium Chloride to water at RT to dissolve. Heat to 60-70 C.
3) Add 2 to 1 while mixing. Mix for about 10 minutes. Alternatively 1 can be added to 2.
4) Cool to RT while mixing. Add water to adjust formulation to 100% while mixing.

Methodology for formulation 009 in Example 6:
1) Heat Isostearic acid to 60-70 C. Add Imiquimod to complete dissolution.
2) Add Pemulen TR-2 to water at RT to dissolve. Heat to 60-70 C. Add Polysorbate 80 to complete dissolution.
3) Add 2 to 1 while mixing. Mix for about 10 minutes. Alternatively 1 can be added to 2.
4) Cool to RT while mixing. Add water to adjust formulation to 100% while mixing.

Methodology for formulation 31 in Example 5 which can be applied to the other formulations in Example 5:
1) Heat Oleyl alcohol to 60-70 C.
2) Add Pemulen TR-2 to water at RT to dissolve. Heat to 60-70 C. Add Polysorbate 80 to complete dissolution.
3) Add 2 to 1 while mixing. Mix for about 10 minutes. Alternatively 1 can be added to 2.
4) Cool to RT while mixing. Add water to adjust formulation to 100% while mixing.

Example 12: Combination of High Fatty Acid and Fatty Alcohols Emulsion Formulations

| cf | HLB/RHLB | Ex. 6 (001) 005 | Ex. 6 (001) 006 | Ex. 6 (001) 007 |
|---|---|---|---|---|
| Caprilic/capric triglycerides | 5 | 2.50 | 2.50 | 10.00 |
| Stearic acid | 15.5 | 30.00 | 30.00 | 30.00 |
| Oleyl alcohol | 14 | 7.50 | 7.50 | |
| Cetyl alcohol | 15.5 | 4.00 | 4.00 | 4.00 |
| Stearyl alcohol | 15.5 | 3.00 | 3.00 | 3.00 |
| Polysorbate 60 | 14.9 | | | 2.70 |
| Polysorbate 80 | 15 | 3.00 | 4.00 | |
| Sorbitane oleate | 4.3 | 0.60 | 0.10 | |
| Sorbitane stearate | 4.7 | | | 0.50 |
| PEG 100 stearate | 18.8 | 1.40 | | |
| Purified water | | 48.00 | 48.90 | 45.10 |
| Benzyl alcohol | | | | 2.00 |
| Glycerin | | | | 2.00 |
| Xanthan gum | | | | 0.35 |
| Hydroxypropyl methylcellulose | | | | 0.35 |
| Total | | 100.00 | 100.00 | 100.00 |
| Propellant (AP-70) | | 8.00 | 8.00 | 8.00 |
| Appearance | | | | |
| Quality | | Good | Good | Good |
| Color | | White | White | White |
| Odor | | No odor | No odor | No odor |
| Shakability | | Poor | Poor | Poor |
| Microscope | | Not measured | Not measured | No crystals |

It is possible to achieve good foam in high concentration (47%) of fatty alcohol, fatty acid and emollient emulsion formulations by using only surfactants. Crystals are seen with 30% stearic acid without fatty alcohol. Surprisingly, the addition of fatty alcohols to a high level of fatty acid (30%) which is otherwise insoluble results in the absence of crystals on microscopic observation. The presence of liquid hydrophobic solvent may contribute to this effect.

Example 13: Emulsion Formulations with Solid and Liquid Fatty Acids

| cf | HLB/RHLB | Ex. 7 (027) 008 |
|---|---|---|
| Isostearic acid | 13 | 42.70 |
| Stearic acid | 15.5 | 23.70 |
| PEG-30 dipolyhydroxystearate | 5.5 | 2.00 |
| Purified water | | 26.10 |
| Sodium Chloride | | 0.50 |
| Imiquimod | | 5.00 |
| Total | | 100.00 |
| Propellant (AP-70) | | 8.00 |
| Appearance | | |
| Quality | | Good |
| Color | | White |
| Odor | | No odor |
| Shakability | | Poor |
| Microscope | | No crystals |

It is possible to achieve good foam with high concentrations (66.4%) of solid and liquid fatty acids combined using only one surfactant. The ratio of solid to liquid fatty acids is about 1:2. While using liquid hydrophobic solvent, no crystals of Imiquimod were observed.

Section D—Pharmaceutical and Cosmetic Formulations

D1—Example 14—Exemplary Prophetic Foams Containing Active Pharmaceutical Ingredients (API)

Exemplary concentrations of active ingredients in foamable compositions are set out in Table 2 and in the following additional prophetic examples. Each active ingredient is added into, for example, any of the carriers listed in any of the above Examples in a therapeutically effective concentration and amount. The methodology of addition is well known to those of the art. The composition is adjusted in each case so that it is made up to 100% w/w by addition or reduction of water or a wax or waxy substance, counterpart or derivative or other solvent as is appropriate to the active agents concerned.

A—Exemplary Concentration Ranges of Some APIs which are Addable to Foams

TABLE 2

| Class | Concentration | Exemplary Use |
|---|---|---|
| Hydrocortisone acetate | 1% | Steroid responsive inflammation and psoriasis or atopic dermatitis |
| Betamethasone valerate | 0.12% | |
| Clobetasol proprionate | 0.05% | |
| Acyclovir | 5% | Viral infection, herpes |
| Ciclopirox | 1% | Fungal infection, seborrhea, dandruff, |
| Clindamycin | 1-2% | Bacterial infection, acne, rosacea, |
| Azelaic acid | 15% | Acne, rosacea, pigmentation disorder and various dermatoses |
| Metronidazol | 0.25%-2% | Rosacea, bacterial infections and parasite infestations |
| Diclofenac | 1% | Osteoarthritus, joint pain |
| Tacrolimus | 0.2% | Atopic dermatitis, eczema and inflammation |
| Caffeine | 5% | anti-cellulite |
| Clotrimazole | 1% | Fungal infection |
| Lidocaine base | 2% | Local anaesthetic |
| Terbinafine HCL | 1% | Fungal infection |
| Gentamycin | 0.1% | Bacterial skin infections, burns or ulcers |
| Dexpanthenol | 5% | Wounds, ulcers, minor skin infections |
| Urea | 5-10% | Emollient and keratolytic Atopic dermatitis, eczema, ichthyosis and hyperkeratotic skin disorders |
| Ammonium lactate | 12%-17.5% | Dry scaly conditions of the skin including ichthyosis |
| Povidone-iodine | 10% | Antimicrobial - antiseptic |
| Benzoyl peroxide | 1%-10% | Acne |
| Alpha-hydroxy acids | 1%-20% | Aging, wrinkles |
| Salicylic acid | 1%-10% | Acne |
| Hydroquinone | 1%-10% | Pigmentation disorders |
| Calcipotriol | 0.005 | Psoriasis |
| Ilmiquimod | 1%-5% | Skin cancers, genital warts |

B—Prophetic Steroid Compositions

The following steroids can be included in carriers, compositions and foams: betamethasone valerate 0.12%, clobetasol propionate 0.05%, betamethasone dipropionate 0.05%, fluocinolone acetonide 0.025%, hydrocortisone acetate 0.5% and hydrocortisone butyrate 0.1%.

C—Prophetic Vitamin and Steroid Compositions

Additionally, one or more of the following vitamins can be included in the carriers, compositions and foams: vitamin C (ascorbic acid) between 0.1 and 5%; for example, 0.1% 1%, 2% 3%, 4%, or 5%; vitamin C (magnesium ascorbyl phosphate) 3%, retinol 1%, retinoic acid 0.1%, niacinamide 2% and tocopherol 1% and Vitamin K. between 0.1 and 2%, for example, 0.1% or 1% or 2%.

D—Prophetic Vitamin Compositions with or without an Additional Therapeutic Agent Foamable vitamin compositions at 0.1%, 1%, 2%, 3%, 4%, or 5%, by weight of composition are made up with or without an active agent and added to any of the vehicles or compositions illustrated in the above Examples.

E—Prophetic Microsponge Formulations.

The following microsponges can be included in any of the carriers, compositions and foams described herein or exemplified in any of the preceding examples.

| Ingredients | w/w % | w/w % | w/w % | w/w % | w/w % |
|---|---|---|---|---|---|
| Microsponge polymer | 1.00 | 3.00% | 5.00% | 10.00% | 15.00 |
| hydrophobic wax in water emulsion | 99.00 | 97.00 | 95.00 | 90.00 | 85.00 |
| Total | 100.00 | 100.00 | 100.00 | 100.00 | 100.00 |
| Propellant AP-70% | 8-00 | 8-00 | 8-00 | 8-00 | 8-00 |

Procedure to prepare formulations with microsponge polymer.

1.) Prepare a hydrophobic wax in water emulsion as described herein.

2.) When the formulation is at room temperature, the microsponge polymer encapsulating the active agent(s) is added and the formulation is mixed for about 5 to about 10 minutes until a uniform dispersion is obtained.

Note: Where Drug Microsponge X % w/w is provided it refers to the microsponges including the trapped drug and any other ingredients incorporated when loading the microsponges.

E—Different Drug Classes

All the above examples represent different drug classes and it is to be understood that other drugs belonging to each of the classes represented above or described elsewhere in the specification may be included and may be used in the compositions in a safe and effective amount.

What is claimed is:

1. A foamable composition for a pharmaceutical comprising:
   A. a carrier comprising:
      a. at least about 20% by weight of a liquid wax comprising one or more free fatty acids, wherein at least one free fatty acid is oleic acid and wherein the oleic acid is at least about 20% by weight of the carrier;
      b. a surface-active agent;
      c. a polymeric agent; and
      d. a solid wax comprising a solid paraffin wax;
   wherein the ratio of liquid wax to solid wax is about 3:1 to about 10:1, and
   B. a liquefied hydrocarbon gas propellant at a concentration of about 3% to about 35% by weight of the foamable composition;
   wherein the composition has a water content less than about 5% by weight;
   wherein the composition is not an emulsion; and wherein, upon release from a pressurized container, a breakable foam is produced.

2. The foamable composition of claim 1, wherein the solid wax further comprises a solid wax selected from the group consisting of a fatty acid, a fatty alcohol, a microcrystalline wax, a petroleum wax, a polyethylene wax, a beeswax, a candelilla wax, a castor wax, a Chinese wax, a Fischer-Tropsch wax, a rice bran wax, a tallow, a wool wax, and a mixture of any two or more thereof.

3. The foamable composition of claim 2, wherein the solid wax further comprises a solid wax selected from the group consisting of stearic acid, cetyl alcohol, behenyl alcohol, stearyl alcohol, and a mixture of any two or more thereof.

4. The foamable composition of claim 1, wherein the liquid wax enables the solid wax to solubilize.

5. The foamable composition of claim 1, wherein solid wax crystals are not visible and the composition is flowable through an aerosol valve.

6. The foamable composition of claim 1, wherein the polymeric agent is present in the composition at a concentration of about 0.01% to about 5% by weight of the carrier and is selected from the group consisting of a bioadhesive agent, a gelling agent, a film forming agent, and a phase change agent.

7. The foamable composition of claim 1, wherein the surface-active agent is selected from the group consisting of a polysorbate, polyoxyethylene (20) sorbitan monostearate, polyoxyethylene (20) sorbitan monooleate, a polyoxyethylene fatty acid ester, polyoxyethylene (8) stearate, polyoxyethylene (20) stearate, polyoxyethylene (40) stearate, polyoxyethylene (100) stearate, a polyoxyethylene alkyl ether, a polyoxyethylene cetyl ether, polyoxyethylene (23) cetyl ether, polyoxyethylene (2) cetyl ether, polyoxyethylene (10) cetyl ether, a sucrose ester, a partial ester of sorbitol, sorbitan monolaurate, a monoglyceride, a diglyceride, isoceteth-20, steareth 2, glyceryl stearate, steareth-21, sorbitan stearate, laureth 4, sorbitan monooleate, ceteareth 20, steareth 20, ceteth 20, macrogol cetostearyl ether, PEG-30 dipolyhydroxystearate, sucrose distearate, cetomacrogol ether, cetearyl glucoside, polysorbate 20; methyl glucose sesquistearate, a sucrose stearic acid ester, a phospholipid, and a mixture of any two or more thereof.

8. The foamable composition of claim 7, wherein the surface-active agent is selected from the group consisting of sorbitan stearate, glyceryl monostearate, and a mixture thereof.

9. The foamable composition of claim 1, wherein the surface active agent also functions as a solvent.

10. The foamable composition of claim 1, wherein the polymeric agent is selected from the group consisting of a cross-linked polyacrylate polymer, acrylates/C10-30 alkyl acrylate crosspolymers, a locust bean gum, sodium alginate, sodium caseinate, an egg albumin, a gelatin agar, a carrageenin gum, a xanthan gum, a quince seed extract, a tragacanth gum, a guar gum, a cationic guar, a hydroxypropyl guar gum, a starch, an amine-bearing polymer, a chitosan, an alginic acid, a hyaluronic acid, a chemically modified starch, a carboxyvinyl polymer, a polyvinylpyrrolidone, a polyvinyl alcohol, a polyacrylic acid polymer, a polymethacrylic acid polymer, a polyvinyl acetate, a polyvinyl chloride polymer, a polyvinylidene chloride polymer, a methylcellulose, a hydroxypropyl cellulose, a hydroxypropyl methylcellulose, a hydroxyethyl cellulose, a methylhydroxyethylcellulose, a carboxymethylcellulose, a hydroxyethylcarboxymethylcellulose, a cationic cellulose, an aluminum starch octenylsuccinate, a sodium starch octenylsuccinate, and a mixture of any two or more thereof.

11. The foamable composition of claim 1, wherein the composition further comprises a solvent selected from the group consisting of an organic carrier, a hydrophilic solvent, a hydrophobic solvent, a potent solvent, a polar solvent, a silicone, an emollient, and a mixture thereof.

12. The foamable composition of claim 11, wherein the solvent comprises dimethyl sulfoxide.

13. The foamable composition of claim 11, wherein the solvent comprises a polyethylene glycol.

14. The foamable composition of claim 1, wherein the surface active agent is between about 0.2% to about 8% by weight.

15. The foamable composition of claim 1, further comprising an additional component selected from the group consisting of a modulating agent, a polar solvent, an anti perspirant, an anti-static agent, a buffering agent, a bulking agent, a chelating agent, a colorant, a conditioner, a deodorant, a diluent, a dye, an emollient, fragrance, a humectant, an occlusive agent, a penetration enhancer, a perfuming agent, a permeation enhancer, a pH-adjusting agent, a preservative, a skin penetration enhancer, a sunscreen, a sun blocking agent, a sunless tanning agent, a vitamin, and a mixture of any two or more thereof.

16. The foamable composition of claim 1, further comprising an active agent.

17. The foamable composition of claim 16, wherein at least 95% of the active ingredient has been solubilized.

18. The foamable composition of claim 16, wherein the active agent is selected from the group consisting of an active herbal extract, an acaricide, an age spot and keratose removing agent, an allergen, an analgesic, a local anesthetic, an antiacne agent, an antiallergic agent, an antiaging agent, an antibacterial, an antibiotic, an antiburn agent, an anticancer agent, an antidandruff agent, an antidepressant, an anti-dermatitis agent, an antiedemic, an antihistamine, an antihelminth, an antihyperkeratolyte agent, an antiinflammatory agent, an antiirritant, an antilipemic, an antimicrobial, an antimycotic, an antiproliferative agent, an antioxidant, an anti-wrinkle agent, an antipruritic, an antipsoriatic agent, an antirosacea agent, an antiseborrheic agent, an antiseptic agent, an antiswelling agent, an antiviral agent, an antiyeast agent, an astringent, a topical cardiovascular agent, a chemotherapeutic agent, a corticosteroid, a dicarboxylic acid, a disinfectant, a fungicide, a hair growth regulator, a hormone, a hydroxy acid, an immunosuppressant, an immunoregulating agent, an immunomodulatory, an insecticide, an insect repellent, a keratolytic agent, a lactam, a metal oxide, a mitocide, a neuropeptide, a steroid, a non-steroidal anti-inflammatory agent, an oxidizing agent, a pediculicide, a photodynamic therapy agent, a retinoid, a sanative, a scabicide, a vasoconstrictor, a vasodilator, a vitamin, a vitamin D derivative, a wound healing agent, a wart remover; an agent having activity against superficial basal cell carcinomas, actinic keratoses, Bowen's disease, or other squamous cell carcinomas and molluscum contagiosum; an agent having activity against herpes simplex virus infections, other viral infections, or eczema; a vaccine adjuvant, and a mixture of any two or more thereof.

19. The foamable composition of claim 18, wherein the active agent is an anti-cancer agent.

20. A method of treating or ameliorating a skin, mucosal or body cavity cancer disorder of a mammalian subject, comprising administering the foamable composition of claim 19 to the skin, a mucosal surface, or a body cavity of said mammalian subject.

21. The method of claim 20, wherein the cancer disorder is selected from the group consisting of skin neoplasia, skin neoplasms, skin cancer, ischemic necrosis, moles, Kaposi's sarcoma, melanoma, basal cell carcinoma, squamous cell carcinoma, scleroderma, vulvar intraepithelial neoplasia, genital cancer, cancer of the cervix, cancer of the vulva, cancer of the vagina, anal cancer, polyps of the colon and rectum, superficial basal cell carcinomas, and Bowen's disease.

22. A foamable composition for a pharmaceutical comprising:
A. a carrier comprising:
  a. a solvent comprising:
    i. at least about 20% by weight of a liquid wax comprising one or more free fatty acids, wherein at least one free fatty acid is oleic acid and wherein the oleic acid is at least about 20% by weight of the carrier; and
    ii. at least one potent solvent, wherein the concentration of the potent solvent is more than about 60% by weight of the solvent;
  b. a surface-active agent;
  c. a polymeric agent; and
  d. a solid wax comprising a solid paraffin wax;
wherein the ratio of liquid wax to solid wax is about 3:1 to about 10:1, and
B. a liquefied hydrocarbon gas propellant at a concentration of about 3% to about 35% by weight of the foamable composition;
wherein,
the foamable composition a water content less than about 5% by weight;
wherein the foamable composition is not an emulsion; and
upon release from a pressurized container, a breakable foam is produced.

23. The foamable composition of claim 1, wherein the solid wax comprises a paraffin wax, stearyl alcohol, behenyl alcohol, or a mixture of any two or more thereof; wherein the surface-active agent comprises glyceryl monostearate, sorbitan monostearate, or a mixture thereof; wherein the polymeric agent comprises a methylcellulose; wherein the composition further comprises a polar solvent comprising dimethyl sulfoxide, polyethylene glycol, or a mixture thereof; and wherein the composition further comprises an anti-cancer agent.

24. The foamable composition of claim 1, wherein the surface active agent is between about 0.2% to about 8% by weight; wherein the polymeric agent is present in the composition at a concentration of about 0.01% to about 5% by weight, and wherein the composition further comprises a polar solvent at a concentration of about 40% to about 80% by weight.

25. The foamable composition of claim 22, wherein the solid wax further comprises stearyl alcohol, behenyl alcohol, or a mixture thereof; wherein the surface-active agent comprises glyceryl monostearate, sorbitan monostearate, or a mixture thereof; wherein the polymeric agent comprises a methylcellulose; wherein the potent solvent comprises dimethyl sulfoxide, polyethylene glycol, or a mixture thereof; and wherein the composition further comprises an anti-cancer agent.

26. The foamable composition of claim 22, wherein the surface active agent is between about 0.2% to about 8% by weight; wherein the polymeric agent is present in the composition at a concentration of about 0.01% to about 5% by weight.

27. The foamable composition of claim 22, wherein the composition is waterless.

28. The foamable composition of claim 1, wherein the composition has a water content of less than about 2%.

29. The foamable composition of claim 1, wherein the composition has a water content of less than about 1.5%.

30. The foamable composition of claim 22, wherein the composition has a water content of less than about 2%.

31. The foamable composition of claim 22, wherein the composition has a water content of less than about 1.5%.

\* \* \* \* \*